(12) United States Patent
Yang et al.

(10) Patent No.: US 9,956,304 B2
(45) Date of Patent: *May 1, 2018

(54) CONTRAST AGENTS, METHODS FOR PREPARING CONTRAST AGENTS, AND METHODS OF IMAGING

(71) Applicant: GEORGIA STATE UNIVERSITY RESEARCH FOUNDATION, INC., Atlanta, GA (US)

(72) Inventors: Jenny Jie Yang, Marietta, GA (US); Zhiren Liu, Atlanta, GA (US); Shunyi Li, Wuhan (CN); Yubin Zhou, Houston, TX (US); Jie Jiang, Atlanta, GA (US); Shenghui Xue, Atlanta, GA (US); Jingjuan Qiao, Atlanta, GA (US); Lixia Wei, Duluth, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 377 days.

This patent is subject to a terminal disclaimer.

(21) Appl. No.: 14/405,623

(22) PCT Filed: Jun. 5, 2013

(86) PCT No.: PCT/US2013/044292
§ 371 (c)(1),
(2) Date: Dec. 4, 2014

(87) PCT Pub. No.: WO2013/184786
PCT Pub. Date: Dec. 12, 2013

(65) Prior Publication Data
US 2015/0202330 A1    Jul. 23, 2015

Related U.S. Application Data

(60) Provisional application No. 61/655,575, filed on Jun. 5, 2012, provisional application No. 61/818,516, filed on May 2, 2013.

(51) Int. Cl.
*A61K 49/14*    (2006.01)
(52) U.S. Cl.
CPC .................................... *A61K 49/14* (2013.01)
(58) Field of Classification Search
CPC .. A61K 47/00; A61K 47/48246; A61K 49/00; A61K 49/0032; A61K 49/0056; A61K 49/0058; A61K 49/14; A61K 49/1866; A61K 31/00; A61K 31/337; A61K 39/00; A61K 39/0005; A61K 45/00; A61K 45/06; A61K 47/48384; A61K 49/16; A61K 51/00; A61K 51/1093; A61K 33/00; A61K 33/24; C07K 16/28; G01N 33/57415; G01N 33/574343; G01N 33/57449; G01N 33/6872; G01N 33/57492; G01N 2333/705
USPC ......... 424/1.11, 1.64, 1.79, 9.1, 9.34, 134.1; 435/7.1, 325; 436/501; 514/19.3, 21.3, 514/1.1, 21.4, 21.5, 21.6; 530/300, 324, 530/325, 326, 327, 328
See application file for complete search history.

(56) References Cited

U.S. PATENT DOCUMENTS 8,200,312 B2* 6/2012 Degani .................... A61B 5/03
600/420

FOREIGN PATENT DOCUMENTS

| WO | 2001030398 A2 | 5/2001 |
| WO | 2003057829 A2 | 7/2003 |
| WO | 2007030802 A2 | 3/2007 |

OTHER PUBLICATIONS

Yang et al, J. Am. Chem. Soc., Jul. 23, 2008, vol. 130, No. 29, pp. 9260-9267.*
Li, S. et al., "PEGylation of protein-based MRI contrast agents improves relaxivities and biocompatibilities"; Journal of Inorganic Biochemistry; Nov. 19, 2011 (e-pub.); vol. 107, pp. 111-118.
NCBI GenBank Accession No. AAH88164; Jul. 10, 2008.

* cited by examiner

*Primary Examiner* — D L Jones
(74) *Attorney, Agent, or Firm* — Thomas | Horstemeyer, LLP

(57) ABSTRACT

Provided is a protein contrast agent for enhancing an MRI image and comprising a polypeptide having a conformation presenting at least five oxygen atoms positioned to chelate at least one paramagnetic metal ion such as $Gd^{3+}$, each oxygen atom being between about 2 angstrom units and about 5 angstrom units from the metal ion; the metal ion has at least one water molecule electrostatically interacting a distance of less than about 10 angstrom units a target-specific moiety conjugated thereto, at least one polyethylene glycol molecule, and a paramagnetic metal ion. Also provided is a method of obtaining an enhanced MRI image using the protein contrast agent to a T2/T1 or T1/T2 intensity ratio of the MRI image; and (d) obtaining an image of the T2/T1 or T1/T2 intensity ratio.

12 Claims, 13 Drawing Sheets

ProCA1 sequences:

```
                              ↓
SEQ ID No.:1   RDSGTVWGALGHGIELNIPNFQMTDDIDEVRWERGSTLVAEFKRKMKPFLKSGGSGG
SEQ ID No.:2   RDSGTVWGALGHGIELNIPNFQMTDDIDEVRWERGSTLVAEFKRKMKPFLKSGGSGG AP
SEQ ID No.:3   RDSGTVWGALGHGIELNIPNFQMTDDIDEVRWERGSTLVAEFKRKMKPFLKSGGSGG
SEQ ID No.:4   RDSGTVWGALGHGIELNIPNFQMTDDIDEVRWERGSTLVAEFKRKMKPFLKSGGSGGG
SEQ ID No.:5   RDSGTVWGALGHGIELNIPNFQMTDDIDEVRWERGSTLVAEFKRKMKPFLKSGGSGGG
SEQ ID No.:6   RDSGTVWGALGHGIELNIPNFQMTDDIDEVRWERGSTLVAEFKRKMKPFLKSGGSGGG
SEQ ID No.:7   RDSGTVWGALGHGIELNIPNFQMTDDIDEVRWERGSTLVAEFKRKMKPFLKSGGSGGG
SEQ ID No.:8   RDSGTVWGALGHGIELNIPNFQMTDDIDEVRWERGSTLVAEFKRKMKPFLKSGGSGGG
SEQ ID No.:9   RDSGTVWGALGHGIELNIPNFQMTDDIDEVRWERGSTLVAEFKRKMKPFLKSGGSGGG
SEQ ID No.:10  RDSGTVWGALGHGIELNIPNFQMTDDIDEVRWERGSTLVAEFKRKMKPFLKSGGG
SEQ ID No.:11  RDSGTVWGALGHGIELNIPNFQMTDDIDEVRWERGSTLVAEFKRKMKPFLKSGG G
SEQ ID No.:12  RDSGTVWGALGHGIELNIPNFQMTDDIDEVRWERGSTLVAEFKRKMKPFLKSGG G

↓   ↓ ↓
SEQ ID No.:1                      GNHWAVGHLMGGSGGAFEIDANGDLDIKNLTRDDSGTYNVTVYST
SEQ ID No.:2   VSVGGGTVLAKMYPRGNHWAVGHLMGGSGGAFEIDANGDLDIKNLTRDDSGTYNVTVYST
SEQ ID No.:3               EQRLGNQWAVGHLMGGSGGAFEIDANGDLDIKNLTRDDSGTYNVTVYST
SEQ ID No.:4                    NQWAVGHLMGGSGGAFEIDANGDLDIKNLTRDDSGTYNVTVYST
SEQ ID No.:5                    STEWAEENSRGGSGGAFEIDANGDLDIKNLTRDDSGTYNVTVYST
SEQ ID No.:6                      KVFRGNKVKGGSGGAFEIDANGDLDIKNLTRDDSGTYNVTVYST
SEQ ID No.:7                      KIVIARYGKGGSGGAFEIDANGDLDIKNLTRDDSGTYNVTVYST
SEQ ID No.:8            WQPDTAHHWATL     GGSGGAFEIDANGDLDIKNLTRDDSGTYNVTVYST
SEQ ID No.:9         MAEWQPDTAHHWATLPDPLGGSGGAFEIDANGDLDIKNLTRDDSGTYNVTVYST
SEQ ID No.:10      RGDRGDRGDRGDRGDRGDGGG   AFEIDANGDLDIKNLTRDDSGTYNVTVYST
SEQ ID No.:11      LGASWHRPDKFCLGYQKRPLPGGSGGAFEIDANGDLDIKNLTRDDSGTYNVTVYST
SEQ ID No.:12      AGPTWCEDDWYYCWLFGTGGGKGGSGGAFEIDANGDLDIKNLTRDDSGTYNVTVYST

SEQ ID No.:1   NGTRILNKALDLRILE
SEQ ID No.:2   NGTRILNKALDLRILE
SEQ ID No.:3   NGTRILNKALDLRILE
SEQ ID No.:4   NGTRILNKALDLRILE
SEQ ID No.:5   NGTRILNKALDLRILE
SEQ ID No.:6   NGTRILNKALDLRILE
SEQ ID No.:7   NGTRILNKALDLRILE
SEQ ID No.:8   NGTRILNKALDLRILE
SEQ ID No.:9   NGTRILNKALDLRILE
SEQ ID No.:10  NGTRILNKALDLRILE
SEQ ID No.:11  NGTRILNKALDLRILE
SEQ ID No.:12  NGTRILNKALDLRILE
```

*Fig. 1A*

Human CD2 sequences

SEQ ID No.:13 TNALETWGALGQDIELNIPSFQMSDDIDDIKWEKTSDKKKIAQFRKEKETFKEKDGGSGGLG
SEQ ID No.:14 TNALETWGALGQDIELNIPSFQMSDDIDDIKWEKTSDKKKIAQFRKEKETFKEKDGGSGGAG

SEQ ID No.:13 ASWHRPDKFCLGYQKRPLP GGSGGTYELDKNGDLDIKHLKTDDQDIYKVSIYDTKGKNVLE
SEQ ID No.:14 PTWCEDDWYYCWLFGTGGGKGGSGGTYELDKNGDLDIKHLKTDDQDIYKVSIYDTKGKNVLE

SEQ ID No.:13 KIFDLKIQE
SEQ ID No.:14 KIFDLKIQE

*Fig. 1B*

ProCA1. affibody for EGFR targeting

SEQ ID No.:15 GSRDSGTVWGALGHGIELNIPNFQMTDDIDEVRWERGSTLVAEFKRKMKPFLKSGAFEID
SEQ ID No.:15 ANGDLDIKNLTRDDSGTYNVTVYSTNGTRILNKALDLRILEGGSGGVDNKFNKEMWAWEE
SEQ ID No.:15 IRNLPNLNGWQMTAFIASLVDDPSQSANLLAEAKKLNDAQAPK

Humanized ProCA1.affibody for HER-2 targeting

SEQ ID No.:16 TNALETWGALGQDIELNIPSFQMSDDIDDIKWEKTSDKKKIAQFRKEKETFKEKDTYELD
SEQ ID No.:16 KNGDLDIKHLKTDDQDIYKVSIYDTKGKNVLEKIFDLKIQEGGSGGVDNKFNKEMRNAYW
SEQ ID No.:16 EIALLPNLNNQQKRAFIRSLYDDPSQSANLLAEAKKLNDAQAPK

Humanized ProCA1.affibody for EGFR targeting

SEQ ID No.:17 TNALETWGALGQDIELNIPSFQMSDDIDDIKWEKTSDKKKIAQFRKEKETFKEKDTYELD
SEQ ID No.:17 KNGDLDIKHLKTDDQDIYKVSIYDTKGKNVLEKIFDLKIQEGGSGGVDNKFNKEMWAWEE
SEQ ID No.:17 IRNLPNLNGWQMTAFIASLVDDPSQSANLLAEAKKLNDAQAPK

*Fig. 1C*

ProCA3 sequences:

```
                                                          ↓  ↓  ↓      ↓
SEQ ID No.:18  MSMTDLLNAEDIKKAVGAFSATDSFDHKKFFQMVGLKKKSADDVKKVFHMLDKDKDGFIE
SEQ ID No.:19  MSMTDLLNAEDIKKAVGAFSATDSFDHKKFFQMVGLKKKSADDVKKVFHMLDKDKDGFIE
SEQ ID No.:20  MSMTDLLNAEDIKKAVGAFSATDSFDHKKFFQMVGLKKKSADDVKKVFHMLDKDKDGFIE
SEQ ID No.:21  MSMTDLLSAEDIKKAIGAFTAADSFDHKKFFQMVGLKKKSADDVKKVFHILDKDKDGFIE
SEQ ID No.:22  MSMTDLLSAEDIKKAIGAFTAADSFDHKKFFQMVGLKKKSADDVKKVFHILDKDKDGFIE

↓                          ↓  ↓  ↓     ↓   ↓
SEQ ID No.:18  EDELGFILKGFSPDARDLSAKETKMLMAAGDKDGDGKIGVEEWSTLVAES
SEQ ID No.:19  EDELGFILKGFSPDARDLSAKETKMLMAAGDKDGDGKIGVEEWSTLVAESC
SEQ ID No.:20  EDELGFILKGFSPDARDLSAKETKMLMAAGDKDGDGKIEVEEWSTLVAES
SEQ ID No.:21  EDELGSILKGFSSDARDLSAKETKTLMAAGDKDGDGKIEVEEWSTLVAESGGGLGAGGGL
SEQ ID No.:21  EDELGSILKGFSSDARDLSAKETKTLMAAGDKDGDGKIEVEEWSTLVAESGGGAGPTWCE

SEQ ID No.:21  GASWHRPDKFCLGYQKRPLP
SEQ ID No.:22  DDWYYCWLFGTGGGKGGG
```

Fig. 1D

SEQ ID No.: 23
Rat Calmodulin-affibody
ADQLTEEQIAEFKEAFSLFDKDGDGTITTKELGTVMRSLGQNPTEAELQDMINEVDADGDGTIDFPEFLTM
MARKMKDTGGSGGVDNKFNKEMRNAYWEIALLPNLNNQQKRAFIRSLYDDPSQSANLLAEAKKLNDAQAPK
GGSGGDSEEEIREAFRVFDKDGDGYISAAELRHVMTNLGEKLTDEEVDEMIREADIDGDGQVNYEEFVQMM
TAK SEQ ID No.: 24
Rat CaM-Bombesin
ADQLTEEQIAEFKEAFSLFDKDGDGTITTKELGTVMRSLGQNPTEAELQDMINEVDADGDGTIDFPEFLTM
MARKMKDTGGNQWAVGHLMGGDSEEEIREAFRVFDKDGDGYISAAELRHVMTNLGEKLTDEEVDEMIREAD
IDGDGQVNYEEFVQMMTAK SEQ ID No.: 25
Rat CA1-CD2-Affibody CA1-WT
GSRDSGTVWGALGHGIELNIPNFQMTDDIDEVRWERGSTLVAEFKRKMKPFLKSGAFEIDANGDLDIKNLT
RDDSGTYNVTVYSTNGTRILNKALDLRILEGGSGGVDNKFNKEQQNAFYEILHLPNLNEEQRNAFIQSLKD
DPSQSANLLAEAKKLNDAQAPK SEQ ID No.: 26
Rat CA1-CD2-Affibody CA1-$Z_{HER2-4}$
GSRDSGTVWGALGHGIELNIPNFQMTDDIDEVRWERGSTLVAEFKRKMKPFLKSGAFEIDANGDLDIKNLT
RDDSGTYNVTVYSTNGTRILNKALDLRILEGGSGGVDNKFNKELRQAYWEIQALPNLNWTQSRAFIRSLYD
DPSQSANLLAEAKKLNDAQAPK SEQ ID No.: 27
Rat CA1-CD2-Affibody CA1-$Z_{HER342}$
GSRDSGTVWGALGHGIELNIPNFQMTDDIDEVRWERGSTLVAEFKRKMKPFLKSGAFEIDANGDLDIKNLT
RDDSGTYNVTVYSTNGTRILNKALDLRILEGGSGGVDNKFNKEMRNAYWEIALLPNLNNQQKRAFIRSLYD
DPSQSANLLAEAKKLNDAQAPK SEQ ID No.: 28
Rat CA1-CD2-Bombesin (C-terminal)
RDSGTVWGALGHGIELNIPNFQMTDDIDEVRWERGSTLVAEFKRKMKPFLKSGAFEIDANGDLDIKNLTRD
DSGTYNVTVYSTNGTRILNKALDLRILEGGSGGSGNQWAVGHLM SEQ ID No.: 29
Rat CA1-CD2-Bombesin (52I)
RDSGTVWGALGHGIELNIPNFQMTDDIDEVRWERGSTLVAEFKRKMKPFLKSGGSGGGNQWAVGHLMGGSG
GGAFEIDANGDLDIKNLTRDDSGTYNVTVYSTNGTRILNKALDLRILE SEQ ID No.: 30
Rat Parvalbumin
WT
MSMTDLLSAEDIKKAIGAFTAADSFDHKKFFQMVGLKKKSADDVKKVFHILDKDKSGFIEEDELGSILKGF
SSDARDLSAKETKTLMAAGDKDGDGKIGVEEFSTLVAES 60

*Fig. 1E*

SEQ ID No.: 31
S56D
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEFSTLVAES 60

SEQ ID No.: 32
S56D-F103W
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEWSTLVAES 60

SEQ ID No.: 33
E60D
MSMTDLLSAEDIKKAIGAFTAADSFDHKKFFQMVGLKKKSADDVKKVFHILDKDKSGFIDEDELGSILKGF
SSDARDLSAKETKTLMAAGDKDGDGKIGVEEFSTLVAES 60

SEQ ID No.: 34
E60D-F103W
MSMTDLLSAEDIKKAIGAFTAADSFDHKKFFQMVGLKKKSADDVKKVFHILDKDKSGFIDEDELGSILKGF
SSDARDLSAKETKTLMAAGDKDGDGKIGVEEWSTLVAES 60

SEQ ID No.: 35
G99D
MSMTDLLSAEDIKKAIGAFTAADSFDHKKFFQMVGLKKKSADDVKKVFHILDKDKSGFIEEDELGSILKGF
SSDARDLSAKETKTLMAAGDKDGDGKIDVEEFSTLVAES 60

SEQ ID No.: 36
G99D-F103W
MSMTDLLSAEDIKKAIGAFTAADSFDHKKFFQMVGLKKKSADDVKKVFHILDKDKSGFIEEDELGSILKGF
SSDARDLSAKETKTLMAAGDKDGDGKIDVEEWSTLVAES 60

SEQ ID No.: 37
D53S-F103W
MSMTDLLSAEDIKKAIGAFTAADSFDHKKFFQMVGLKKKSADDVKKVFHILSKDKSGFIEEDELGSILKGF
SSDARDLSAKETKTLMAAGDKDGDGKIDVEEWSTLVAES 60

SEQ ID No.: 38
D53E-F103W
MSMTDLLSAEDIKKAIGAFTAADSFDHKKFFQMVGLKKKSADDVKKVFHILEKDKSGFIEEDELGSILKGF
SSDARDLSAKETKTLMAAGDKDGDGKIDVEEWSTLVAES 60

SEQ ID No.: 39
F103WC104
MSMTDLLSAEDIKKAIGAFTAADSFDHKKFFQMVGLKKKSADDVKKVFHILDKDKSGFIEEDELGSILKGF
SSDARDLSAKETKTLMAAGDKDGDGKIGVEEWSTLVAESC 60

*Fig. 1E-continued*

SEQ ID No.: 40
F103W
MSMTDLLSAEDIKKAIGAFTAADSFDHKKFFQMVGLKKKSADDVKKVFHILDKDKSGFIEEDELGSILKGF
SSDARDLSAKETKTLMAAGDKDGDGKIGVEEWSTLVAES 60

SEQ ID No.: 41
Human
MSMTDLLNAEDIKKAVGAFSATDSFDHKKFFQMVGLKKKSADDVKKVFHMLDKDKSGFIEEDELGFILKGF
SPDARDLSAKETKMLMAAGDKDGDGKIGVDEFSTLVAES 60

Rat-Parvalbumin Insertion variants
SEQ ID No.: 42
PV_Collagen
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEWSTLVAESGGGKKWHCYTYFPHHYCVYG SEQ ID No.: 43
PV_Bombsin
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEWSTLVAESGGGAQWAVGHLM SEQ ID No.: 44
PV_Selectin
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEWSTLVAESGGGKYDGDITWDQLWDLMK SEQ ID No.: 45
PV_RGD
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEWSTLVAESGGGRGDRGDRGDRGD SEQ ID No.: 46
PV_Cys
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEWSTLVAESC SEQ ID No.: 47
PV_AFFIBODY
MSMTDLLSAEDIKKAIGAFTAADSFDHKKFFQMVGLKKKSADDVKKVFHILDKDKDGFIEEDELGSILKGF
SSDARDLSAKETKTLMAAGDKDGDGKIGVEEWSTLVAESGGSGGVDNKFNKEMRNAYWEIALLPNLNNQQK
RAFIRSLYDDPSQSANLLAEAKKLNDAQAPK SEQ ID No.: 48
Human-Calbindin D9k
CalbindinD9k
MSTKKSPEELKRIFEKYAAKEGDPDQLSKDELKLLIQAEFPSLLKGPNTLDDLFQELDKNGDGEVSFEEFQ
VLVKKISQ

*Fig. 1E continued*

SEQ ID No.: 49
CalbindinD9kF67W
MSTKKSPEELKRIFEKYAAKEGDPDQLSKDELKLLIQAEFPSLLKGPNTLDDLFQELDKNGDGEVSFEEWQ
VLVKKISQ SEQ ID No.: 50
CalbindinD9kP43M
MSTKKSPEELKRIFEKYAAKEGDPDQLSKDELKLLIQAEFPSLLKGMNTLDDLFQELDKNGDGEVSFEEWQ
VLVKKISQ SEQ ID No.: 51
CalbindinD9kCys
MSTKKSPEELKRIFEKYAAKEGDPDQLSKDELKLLIQAEFPSLLKGPNTLDDLFQELDKNGDGEVSFEEFQ
VLVKKISQC SEQ ID No.: 52
Human-Troponin
MTDQQAEARSYLSEEMIAEFKAAFDMFDADGGGDISVKELGTVMRMLGQTPTKEELDAIIEEVDEDGSGTI
DFEEFLVMMVRQMKEDAKGKSEEELAECFRIFDRNADGYIDPGELAEIFRASGEHVTDEEIESLMKDGDKN
NDGRIDFDEFLKMMEGVQ SEQ ID No.: 53
Rat CA1-CD2-Bombesin-RGD (52I)-Cend
RDSGTVWGALGHGIELNIPNFQMTDDIDEVRWERGSTLVAEFKRKMKPFLKSGGSGGGNQWAVGHLMGGSG
GGAFEIDANGDLDIKNLTRDDSGTYNVTVYSTNGTRILNKALDLRILE-RGD SEQ ID No.: 54
Rat CA1-CD2-Bombesin-RGD (52I)-Nend RGDRDSGTVWGALGHGIELNIPNFQMTDDIDEVRWERGSTLVAEFKRKMKPFLKSGGSGGGNQWAVGHLMG
GSGGGAFEIDANGDLDIKNLTRDDSGTYNVTVYSTNGTRILNKALDLRILE SEQ ID No.: 55
Rat CA1-CD2-RGD-83I
RDSGTVWGALGHGIELNIPNFQMTDDIDEVRWERGSTLVAEFKRKMKPFLKSGAFEIDANGDLDIKNLTRD
DSGTYNVTVYSTGGSGGRGDGGSGGNGTRILNKALDLRILEG SEQ ID No.: 56
Rat CA1-CD2-Bom-52I-RGD-83I
RGDRDSGTVWGALGHGIELNIPNFQMTDDIDEVRWERGSTLVAEFKRKMKPFLKSGGSGGGNQWAVGHLMG
GSGGGAFEIDANGDLDIKNLTRDDSGTYNVTVYSTGGSGGRGDGGSGGNGTRILNKALDLRILE

*Fig. 1E continued*

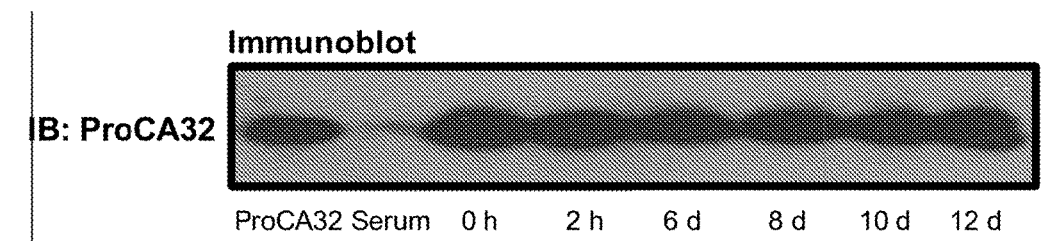

*Fig. 2*

Binding affinity and metal selectivity of ProCA3 variants and Gd-DTPA

| $K_d$ (M) | Gd-DTPA* | ProCA30 | ProCA31 | ProCA32 |
|---|---|---|---|---|
| $Tb^{3+}$ | $9.55 \times 10^{-22}$ | $6.29 \pm 0.13 \times 10^{-18}$ | $1.79 \pm 0.33 \times 10^{-12}$ | $1.21 \pm 0.33 \times 10^{-21}$ |
| $Gd^{3+}$ | $1.86 \times 10^{-21}$ | $6.37 \pm 0.50 \times 10^{-13}$ | $2.55 \pm 0.09 \times 10^{-11}$ | $2.79 \pm 0.36 \times 10^{-22}$ |
| $Ca^{2+}$ | $1.51 \times 10^{-10}$ | $8.35 \pm 0.29 \times 10^{-6}$ | $3.91 \pm 0.96 \times 10^{-6}$ | $3.57 \pm 0.01 \times 10^{-6}$ |
| $Mg^{2+}$ | $2.75 \times 10^{-6}$ | $1.96 \pm 0.12 \times 10^{-4}$ | $2.49 \pm 0.22 \times 10^{-6}$ | $1.72 \pm 0.35 \times 10^{-6}$ |
| $Zn^{2+}$ | $6.31 \times 10^{-19}$ | $2.05 \pm 0.31 \times 10^{-6}$ | $1.30 \pm 0.50 \times 10^{-7}$ | $6.00 \pm 2.00 \times 10^{-8}$ |
| $Log(K_{Gd}/K_{Ca})$ | 10.9 | 2.1 | 2.2 | 13.1 |
| $Log(K_{Gd}/K_{Mg})$ | 13.1 | 6.4 | 4.0 | 15.8 |
| $Log(K_{Gd}/K_{Zn})$ | 2.5 | 4.5 | 3.7 | 14.3 |

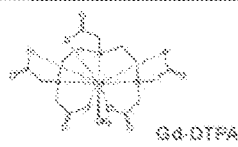
Gd-DTPA

ProCA30
ProCA31

ProCA32

ProCA32 has much higher metal selectivity than that of clinical MRI contrast agents and wild type CaBP (ProCA20).

*Fig. 3*

Simulation shows that ratiometric imaging improve the dynamic range MRI signal in liver

SEQUENCE LISTING

<160> NUMBER OF SEQ ID NOS: 56

<210> SEQ ID NO 1
<211> LENGTH: 118
<212> TYPE: PRT
<213> ORGANISM: Artificial sequence
<220> FEATURE:
<223> OTHER INFORMATION: ProCA1 sequence 1

<400> SEQUENCE: 1

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Gly Asn His Trp Ala Val Gly
    50                  55                  60

His Leu Met Gly Gly Ser Gly Gly Ala Phe Glu Ile Asp Ala Asn Gly
65                  70                  75                  80

Asp Leu Asp Ile Lys Asn Leu Thr Arg Asp Asp Ser Gly Thr Tyr Asn
                85                  90                  95

Val Thr Val Tyr Ser Thr Asn Gly Thr Arg Ile Leu Asn Lys Ala Leu
            100                 105                 110

Asp Leu Arg Ile Leu Glu
        115

<210> SEQ ID NO 2
<211> LENGTH: 135
<212> TYPE: PRT
<213> ORGANISM: Artificial sequence
<220> FEATURE:
<223> OTHER INFORMATION: ProCA1 sequence 2

<400> SEQUENCE: 2

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Ala Pro Val Ser Val Gly Gly
    50                  55                  60

Gly Thr Val Leu Ala Lys Met Tyr Pro Arg Gly Asn His Trp Ala Val
65                  70                  75                  80

Gly His Leu Met Gly Gly Ser Gly Gly Ala Phe Glu Ile Asp Ala Asn
                85                  90                  95

Gly Asp Leu Asp Ile Lys Asn Leu Thr Arg Asp Asp Ser Gly Thr Tyr
            100                 105                 110

Asn Val Thr Val Tyr Ser Thr Asn Gly Thr Arg Ile Leu Asn Lys Ala
        115                 120                 125

Leu Asp Leu Arg Ile Leu Glu
    130                 135

<210> SEQ ID NO 3
<211> LENGTH: 122
<212> TYPE: PRT
<213> ORGANISM: Artificial sequence
<220> FEATURE:
<223> OTHER INFORMATION: ProCA1 sequence 3

<400> SEQUENCE: 3

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
         35                  40                  45

Phe Leu Lys Ser Gly Gly Ser Gly Gly Glu Gln Arg Leu Gly Asn Gln
 50                  55                  60

Trp Ala Val Gly His Leu Met Gly Gly Ser Gly Gly Ala Phe Glu Ile
 65                  70                  75                  80

Asp Ala Asn Gly Asp Leu Asp Ile Lys Asn Leu Thr Arg Asp Asp Ser
                 85                  90                  95

Gly Thr Tyr Asn Val Thr Val Tyr Ser Thr Asn Gly Thr Arg Ile Leu
                 100                 105                 110

Asn Lys Ala Leu Asp Leu Arg Ile Leu Glu
         115                 120

<210> SEQ ID NO 4
<211> LENGTH: 118
<212> TYPE: PRT
<213> ORGANISM: Artificial sequence
<220> FEATURE:
<223> OTHER INFORMATION: ProCA1 sequence 4

<400> SEQUENCE: 4

Arg Asp Ser Gly Thr Val Trp Gly Ala Leu Gly His Gly Ile Glu Leu
 1               5                  10                  15

Asn Ile Pro Asn Phe Gln Met Thr Asp Ile Asp Glu Val Arg Trp
                 20                  25                  30

Glu Arg Gly Ser Thr Leu Val Ala Glu Phe Lys Arg Lys Met Lys Pro
         35                  40                  45

Phe Leu Lys Ser Gly Gly Ser Gly Gly Asn Gln Trp Ala Val Gly
 50                  55                  60

His Leu Met Gly Gly Ser Gly Gly Ala Phe Glu Ile Asp Ala Asn Gly
 65                  70                  75                  80

Asp Leu Asp Ile Lys Asn Leu Thr Arg Asp Asp Ser Gly Thr Tyr Asn
                 85                  90                  95

Val Thr Val Tyr Ser Thr Asn Gly Thr Arg Ile Leu Asn Lys Ala Leu
                 100                 105                 110

Asp Leu Arg Ile Leu Glu
         115

<210> SEQ ID NO 5
<211> LENGTH: 119
<212> TYPE: PRT
<213> ORGANISM: Artificial sequence
<220> FEATURE:
<223> OTHER INFORMATION: ProCA1 sequence 5

<400> SEQUENCE: 5

Arg Asp Ser Gly Thr Val Trp Gly Ala Leu Gly His Gly Ile Glu Leu
 1               5                  10                  15

Asn Ile Pro Asn Phe Gln Met Thr Asp Ile Asp Glu Val Arg Trp
                 20                  25                  30

Glu Arg Gly Ser Thr Leu Val Ala Glu Phe Lys Arg Lys Met Lys Pro
         35                  40                  45

Phe Leu Lys Ser Gly Gly Ser Gly Gly Gly Ser Thr Glu Trp Ala Glu
 50                  55                  60

Glu Asn Ser Arg Gly Gly Ser Gly Gly Ala Phe Glu Ile Asp Ala Asn
 65                  70                  75                  80

Gly Asp Leu Asp Ile Lys Asn Leu Thr Arg Asp Asp Ser Gly Thr Tyr 85                  90                  95

Asn Val Thr Val Tyr Ser Thr Asn Gly Thr Arg Ile Leu Asn Lys Ala
                100                 105                 110

Leu Asp Leu Arg Ile Leu Glu
        115

<210> SEQ ID NO 6
<211> LENGTH: 118
<212> TYPE: PRT
<213> ORGANISM: Artificial sequence
<220> FEATURE:
<223> OTHER INFORMATION: ProCA1 sequence 6

<400> SEQUENCE: 6

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Gly Lys Val Phe Arg Gly Asn
    50                  55                  60

Lys Val Lys Gly Gly Ser Gly Gly Ala Phe Glu Ile Asp Ala Asn Gly
65                  70                  75                  80

Asp Leu Asp Ile Lys Asn Leu Thr Arg Asp Asp Ser Gly Thr Tyr Asn
                85                  90                  95

Val Thr Val Tyr Ser Thr Asn Gly Thr Arg Ile Leu Asn Lys Ala Leu
                100                 105                 110

Asp Leu Arg Ile Leu Glu
        115

<210> SEQ ID NO 7
<211> LENGTH: 118
<212> TYPE: PRT
<213> ORGANISM: Artificial sequence
<220> FEATURE:
<223> OTHER INFORMATION: ProCA1 sequence 7

<400> SEQUENCE: 7

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Gly Lys Ile Val Ile Ala Arg
    50                  55                  60

Tyr Gly Lys Gly Gly Ser Gly Gly Ala Phe Glu Ile Asp Ala Asn Gly
65                  70                  75                  80

Asp Leu Asp Ile Lys Asn Leu Thr Arg Asp Asp Ser Gly Thr Tyr Asn
                85                  90                  95

Val Thr Val Tyr Ser Thr Asn Gly Thr Arg Ile Leu Asn Lys Ala Leu
                100                 105                 110

Asp Leu Arg Ile Leu Glu
        115

<210> SEQ ID NO 8
<211> LENGTH: 121

<212> TYPE: PRT
<213> ORGANISM: Artificial sequence
<220> FEATURE:
<223> OTHER INFORMATION: ProCA1 sequence 8

<400> SEQUENCE: 8

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Gly Trp Gln Pro Asp Thr Ala
    50                  55                  60

His His Trp Ala Thr Leu Gly Gly Ser Gly Gly Ala Phe Glu Ile Asp
65                  70                  75                  80

Ala Asn Gly Asp Leu Asp Ile Lys Asn Leu Thr Arg Asp Asp Ser Gly
                85                  90                  95

Thr Tyr Asn Val Thr Val Tyr Ser Thr Asn Gly Thr Arg Ile Leu Asn
            100                 105                 110

Lys Ala Leu Asp Leu Arg Ile Leu Glu
        115                 120

<210> SEQ ID NO 9
<211> LENGTH: 128
<212> TYPE: PRT
<213> ORGANISM: Artificial sequence
<220> FEATURE:
<223> OTHER INFORMATION: ProCA1 sequence 9

<400> SEQUENCE: 9

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Gly Met Ala Glu Trp Gln Pro
    50                  55                  60

Asp Thr Ala His His Trp Ala Thr Leu Pro Asp Pro Leu Gly Gly Ser
65                  70                  75                  80

Gly Gly Ala Phe Glu Ile Asp Ala Asn Gly Asp Leu Asp Ile Lys Asn
                85                  90                  95

Leu Thr Arg Asp Asp Ser Gly Thr Tyr Asn Val Thr Val Tyr Ser Thr
            100                 105                 110

Asn Gly Thr Arg Ile Leu Asn Lys Ala Leu Asp Leu Arg Ile Leu Glu
        115                 120                 125

<210> SEQ ID NO 10
<211> LENGTH: 125
<212> TYPE: PRT
<213> ORGANISM: Artificial sequence
<220> FEATURE:
<223> OTHER INFORMATION: ProCA1 sequence 10

<400> SEQUENCE: 10

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp

```
                    20                  25                  30

Glu Arg Gly Ser Thr Leu Val Ala Glu Phe Lys Arg Lys Met Lys Pro
            35                  40                  45

Phe Leu Lys Ser Gly Gly Gly Arg Gly Asp Arg Gly Asp Arg Gly Asp
        50                  55                  60

Arg Gly Asp Arg Gly Asp Arg Gly Asp Arg Gly Asp Gly Gly Gly Ala
65                  70                  75                  80

Phe Glu Ile Asp Ala Asn Gly Asp Leu Asp Ile Lys Asn Leu Thr Arg
                85                  90                  95

Asp Asp Ser Gly Thr Tyr Asn Val Thr Val Tyr Ser Thr Asn Gly Thr
            100                 105                 110

Arg Ile Leu Asn Lys Ala Leu Asp Leu Arg Ile Leu Glu
        115                 120                 125

<210> SEQ ID NO 11
<211> LENGTH: 127
<212> TYPE: PRT
<213> ORGANISM: Artificial sequence
<220> FEATURE:
<223> OTHER INFORMATION: ProCA1 sequence 11

<400> SEQUENCE: 11

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Gly Gly Leu Gly Ala Ser Trp His Arg Pro Asp
        50                  55                  60

Lys Phe Cys Leu Gly Tyr Gln Lys Arg Pro Leu Pro Gly Gly Ser Gly
65                  70                  75                  80

Gly Ala Phe Glu Ile Asp Ala Asn Gly Asp Leu Asp Ile Lys Asn Leu
                85                  90                  95

Thr Arg Asp Asp Ser Gly Thr Tyr Asn Val Thr Val Tyr Ser Thr Asn
            100                 105                 110

Gly Thr Arg Ile Leu Asn Lys Ala Leu Asp Leu Arg Ile Leu Glu
        115                 120                 125

<210> SEQ ID NO 12
<211> LENGTH: 128
<212> TYPE: PRT
<213> ORGANISM: Artificial sequence
<220> FEATURE:
<223> OTHER INFORMATION: ProCA1 sequence 12

<400> SEQUENCE: 12

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Gly Gly Ala Gly Pro Thr Trp Cys Glu Asp Asp
        50                  55                  60

Trp Tyr Tyr Cys Trp Leu Phe Gly Thr Gly Gly Lys Gly Gly Ser
65                  70                  75                  80
```

Gly Gly Ala Phe Glu Ile Asp Ala Asn Gly Asp Leu Asp Ile Lys Asn
            85                  90                  95

Leu Thr Arg Asp Asp Ser Gly Thr Tyr Asn Val Thr Val Tyr Ser Thr
            100                 105                 110

Asn Gly Thr Arg Ile Leu Asn Lys Ala Leu Asp Leu Arg Ile Leu Glu
            115                 120                 125

<210> SEQ ID NO 13
<211> LENGTH: 132
<212> TYPE: PRT
<213> ORGANISM: Artificial sequence
<220> FEATURE:
<223> OTHER INFORMATION: ProCA CD2 human

<400> SEQUENCE: 13

Thr Asn Ala Leu Glu Thr Trp Gly Ala Leu Gly Gln Asp Ile Glu Leu
1               5                   10                  15

Asn Ile Pro Ser Phe Gln Met Ser Asp Asp Ile Asp Asp Ile Lys Trp
            20                  25                  30

Glu Lys Thr Ser Asp Lys Lys Lys Ile Ala Gln Phe Arg Lys Glu Lys
            35                  40                  45

Glu Thr Phe Lys Glu Lys Asp Gly Gly Ser Gly Gly Leu Gly Ala Ser
        50                  55                  60

Trp His Arg Pro Asp Lys Phe Cys Leu Gly Tyr Gln Lys Arg Pro Leu
65                  70                  75                  80

Pro Gly Gly Ser Gly Gly Thr Tyr Glu Leu Asp Lys Asn Gly Asp Leu
                85                  90                  95

Asp Ile Lys His Leu Lys Thr Asp Asp Gln Asp Ile Tyr Lys Val Ser
            100                 105                 110

Ile Tyr Asp Thr Lys Gly Lys Asn Val Leu Glu Lys Ile Phe Asp Leu
            115                 120                 125

Lys Ile Gln Glu
        130

<210> SEQ ID NO 14
<211> LENGTH: 133
<212> TYPE: PRT
<213> ORGANISM: Artificial sequence
<220> FEATURE:
<223> OTHER INFORMATION: ProCA CD2 human

<400> SEQUENCE: 14

Thr Asn Ala Leu Glu Thr Trp Gly Ala Leu Gly Gln Asp Ile Glu Leu
1               5                   10                  15

Asn Ile Pro Ser Phe Gln Met Ser Asp Asp Ile Asp Asp Ile Lys Trp
            20                  25                  30

Glu Lys Thr Ser Asp Lys Lys Lys Ile Ala Gln Phe Arg Lys Glu Lys
            35                  40                  45

Glu Thr Phe Lys Glu Lys Asp Gly Gly Ser Gly Gly Ala Gly Pro Thr
        50                  55                  60

Trp Cys Glu Asp Asp Trp Tyr Tyr Cys Trp Leu Phe Gly Thr Gly Gly
65                  70                  75                  80

Gly Lys Gly Gly Ser Gly Gly Thr Tyr Glu Leu Asp Lys Asn Gly Asp
                85                  90                  95

Leu Asp Ile Lys His Leu Lys Thr Asp Asp Gln Asp Ile Tyr Lys Val
            100                 105                 110

Ser Ile Tyr Asp Thr Lys Gly Lys Asn Val Leu Glu Lys Ile Phe Asp
            115                 120                 125

Leu Lys Ile Gln Glu
        130

<210> SEQ ID NO 15
<211> LENGTH: 163
<212> TYPE: PRT
<213> ORGANISM: Artificial sequence
<220> FEATURE:
<223> OTHER INFORMATION: ProCA1.affibody for EGFR targeting

<400> SEQUENCE: 15

Gly Ser Arg Asp Ser Gly Thr Val Trp Gly Ala Leu Gly His Gly Ile
1               5                   10                  15

Glu Leu Asn Ile Pro Asn Phe Gln Met Thr Asp Ile Asp Val
            20                  25                  30

Arg Trp Glu Arg Gly Ser Thr Leu Val Ala Glu Phe Lys Arg Lys Met
        35                  40                  45

Lys Pro Phe Leu Lys Ser Gly Ala Phe Glu Ile Asp Ala Asn Gly Asp
    50                  55                  60

Leu Asp Ile Lys Asn Leu Thr Arg Asp Asp Ser Gly Thr Tyr Asn Val
65                  70                  75                  80

Thr Val Tyr Ser Thr Asn Gly Thr Arg Ile Leu Asn Lys Ala Leu Asp
                85                  90                  95

Leu Arg Ile Leu Glu Gly Gly Ser Gly Gly Val Asp Asn Lys Phe Asn
            100                 105                 110

Lys Glu Met Trp Ala Trp Glu Glu Ile Arg Asn Leu Pro Asn Leu Asn
        115                 120                 125

Gly Trp Gln Met Thr Ala Phe Ile Ala Ser Leu Val Asp Asp Pro Ser
    130                 135                 140

Gln Ser Ala Asn Leu Leu Ala Glu Ala Lys Lys Leu Asn Asp Ala Gln
145                 150                 155                 160

Ala Pro Lys

<210> SEQ ID NO 16
<211> LENGTH: 164
<212> TYPE: PRT
<213> ORGANISM: Artificial sequence
<220> FEATURE:
<223> OTHER INFORMATION: Humanized ProCA1.affibody for Her-2 targeting

<400> SEQUENCE: 16

Thr Asn Ala Leu Glu Thr Trp Gly Ala Leu Gly Gln Asp Ile Glu Leu
1               5                   10                  15

Asn Ile Pro Ser Phe Gln Met Ser Asp Asp Ile Asp Asp Ile Lys Trp
            20                  25                  30

Glu Lys Thr Ser Asp Lys Lys Ile Ala Gln Phe Arg Lys Glu Lys
        35                  40                  45

Glu Thr Phe Lys Glu Lys Asp Thr Tyr Glu Leu Asp Lys Asn Gly Asp
    50                  55                  60

Leu Asp Ile Lys His Leu Lys Thr Asp Asp Gln Asp Ile Tyr Lys Val
65                  70                  75                  80

Ser Ile Tyr Asp Thr Lys Gly Lys Asn Val Leu Glu Lys Ile Phe Asp
                85                  90                  95

Leu Lys Ile Gln Glu Gly Gly Ser Gly Gly Val Asp Asn Lys Phe Asn
            100                 105                 110

Lys Glu Met Arg Asn Ala Tyr Trp Glu Ile Ala Leu Leu Pro Asn Leu
        115                 120                 125

Asn Asn Gln Gln Lys Arg Ala Phe Ile Arg Ser Leu Tyr Asp Asp Pro
            130                 135                 140

Ser Gln Ser Ala Asn Leu Leu Ala Glu Ala Lys Lys Leu Asn Asp Ala
145                 150                 155                 160

Gln Ala Pro Lys

<210> SEQ ID NO 17
<211> LENGTH: 163
<212> TYPE: PRT
<213> ORGANISM: Artificial sequence
<220> FEATURE:
<223> OTHER INFORMATION: Humanized ProCA1.affibody for EGFR targeting

<400> SEQUENCE: 17

Thr Asn Ala Leu Glu Thr Trp Gly Ala Leu Gly Gln Asp Ile Glu Leu
1               5                   10                  15

Asn Ile Pro Ser Phe Gln Met Ser Asp Asp Ile Asp Asp Ile Lys Trp
            20                  25                  30

Glu Lys Thr Ser Asp Lys Lys Ile Ala Gln Phe Arg Lys Glu Lys
        35                  40                  45

Glu Thr Phe Lys Glu Lys Asp Thr Tyr Glu Leu Asp Lys Asn Gly Asp
50                  55                  60

Leu Asp Ile Lys His Leu Lys Thr Asp Gln Asp Ile Tyr Lys Val
65                  70                  75                  80

Ser Ile Tyr Asp Thr Lys Gly Lys Asn Val Leu Glu Lys Ile Phe Asp
                85                  90                  95

Leu Lys Ile Gln Glu Gly Gly Ser Gly Gly Val Asp Asn Lys Phe Asn
            100                 105                 110

Lys Glu Met Trp Ala Trp Glu Glu Ile Arg Asn Leu Pro Asn Leu Asn
        115                 120                 125

Gly Trp Gln Met Thr Ala Phe Ile Ala Ser Leu Val Asp Asp Pro Ser
    130                 135                 140

Gln Ser Ala Asn Leu Leu Ala Glu Ala Lys Lys Leu Asn Asp Ala Gln
145                 150                 155                 160

Ala Pro Lys

<210> SEQ ID NO 18
<211> LENGTH: 110
<212> TYPE: PRT
<213> ORGANISM: Artificial sequence
<220> FEATURE:
<223> OTHER INFORMATION: ProCA3

<400> SEQUENCE: 18

Met Ser Met Thr Asp Leu Leu Asn Ala Glu Asp Ile Lys Lys Ala Val
1               5                   10                  15

Gly Ala Phe Ser Ala Thr Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Met Leu Asp Lys Asp Lys Asp Gly Phe Ile Glu Glu Asp Glu Leu
50                  55                  60

Gly Phe Ile Leu Lys Gly Phe Ser Pro Asp Ala Arg Asp Leu Ser Ala
65                  70                  75                  80

Lys Glu Thr Lys Met Leu Met Ala Ala Gly Asp Lys Asp Gly Asp Gly
                85                  90                  95

```
Lys Ile Gly Val Glu Glu Trp Ser Thr Leu Val Ala Glu Ser
            100                 105                 110
```

<210> SEQ ID NO 19
<211> LENGTH: 111
<212> TYPE: PRT
<213> ORGANISM: Artificial sequence
<220> FEATURE:
<223> OTHER INFORMATION: ProCA3

<400> SEQUENCE: 19

```
Met Ser Met Thr Asp Leu Leu Asn Ala Glu Asp Ile Lys Lys Ala Val
1               5                   10                  15

Gly Ala Phe Ser Ala Thr Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Met Leu Asp Lys Asp Lys Asp Gly Phe Ile Glu Glu Asp Glu Leu
    50                  55                  60

Gly Phe Ile Leu Lys Gly Phe Ser Pro Asp Ala Arg Asp Leu Ser Ala
65                  70                  75                  80

Lys Glu Thr Lys Met Leu Met Ala Ala Gly Asp Lys Asp Gly Asp Gly
                85                  90                  95

Lys Ile Gly Val Glu Glu Trp Ser Thr Leu Val Ala Glu Ser Cys
            100                 105                 110
```

<210> SEQ ID NO 20
<211> LENGTH: 110
<212> TYPE: PRT
<213> ORGANISM: Artificial sequence
<220> FEATURE:
<223> OTHER INFORMATION: ProCA3

<400> SEQUENCE: 20

```
Met Ser Met Thr Asp Leu Leu Asn Ala Glu Asp Ile Lys Lys Ala Val
1               5                   10                  15

Gly Ala Phe Ser Ala Thr Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Met Leu Asp Lys Asp Lys Asp Gly Phe Ile Glu Glu Asp Glu Leu
    50                  55                  60

Gly Phe Ile Leu Lys Gly Phe Ser Pro Asp Ala Arg Asp Leu Ser Ala
65                  70                  75                  80

Lys Glu Thr Lys Met Leu Met Ala Ala Gly Asp Lys Asp Gly Asp Gly
                85                  90                  95

Lys Ile Glu Val Glu Glu Trp Ser Thr Leu Val Ala Glu Ser
            100                 105                 110
```

<210> SEQ ID NO 21
<211> LENGTH: 140
<212> TYPE: PRT
<213> ORGANISM: Artificial sequence
<220> FEATURE:
<223> OTHER INFORMATION: ProCA3

<400> SEQUENCE: 21

```
Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
```

```
                20              25              30
Met Val Gly Leu Lys Lys Ser Ala Asp Asp Val Lys Lys Val Phe
                35              40                  45

His Ile Leu Asp Lys Asp Lys Asp Gly Phe Ile Glu Glu Asp Glu Leu
        50              55              60

Gly Ser Ile Leu Lys Gly Phe Ser Ser Asp Ala Arg Asp Leu Ser Ala
65              70                  75              80

Lys Glu Thr Lys Thr Leu Met Ala Ala Gly Asp Lys Asp Gly Asp Gly
                85              90                  95

Lys Ile Glu Val Glu Glu Trp Ser Thr Leu Val Ala Glu Ser Gly Gly
                100             105                 110

Gly Leu Gly Ala Gly Gly Leu Gly Ala Ser Trp His Arg Pro Asp
            115             120             125

Lys Phe Cys Leu Gly Tyr Gln Lys Arg Pro Leu Pro
    130             135                 140

<210> SEQ ID NO 22
<211> LENGTH: 138
<212> TYPE: PRT
<213> ORGANISM: Artificial sequence
<220> FEATURE:
<223> OTHER INFORMATION: ProCA3

<400> SEQUENCE: 22

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
                20              25                  30

Met Val Gly Leu Lys Lys Ser Ala Asp Asp Val Lys Lys Val Phe
                35              40                  45

His Ile Leu Asp Lys Asp Lys Asp Gly Phe Ile Glu Glu Asp Glu Leu
        50              55              60

Gly Ser Ile Leu Lys Gly Phe Ser Ser Asp Ala Arg Asp Leu Ser Ala
65              70                  75              80

Lys Glu Thr Lys Thr Leu Met Ala Ala Gly Asp Lys Asp Gly Asp Gly
                85              90                  95

Lys Ile Glu Val Glu Glu Trp Ser Thr Leu Val Ala Glu Ser Gly Gly
                100             105                 110

Gly Ala Gly Pro Thr Trp Cys Glu Asp Trp Tyr Tyr Cys Trp Leu
            115             120             125

Phe Gly Thr Gly Gly Gly Lys Gly Gly Gly
    130             135

<210> SEQ ID NO 23
<211> LENGTH: 216
<212> TYPE: PRT
<213> ORGANISM: Artificial sequence
<220> FEATURE:
<223> OTHER INFORMATION: Rat Calmodulin-affibody

<400> SEQUENCE: 23

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
                20              25                  30

Gly Thr Val Met Arg Ser Leu Gly Gln Asn Pro Thr Glu Ala Glu Leu
            35              40                  45
```

```
Gln Asp Met Ile Asn Glu Val Asp Ala Asp Gly Asp Gly Thr Ile Asp
        50                  55                  60

Phe Pro Glu Phe Leu Thr Met Met Ala Arg Lys Met Lys Asp Thr Gly
 65                  70                  75                  80

Gly Ser Gly Gly Val Asp Asn Lys Phe Asn Lys Glu Met Arg Asn Ala
                 85                  90                  95

Tyr Trp Glu Ile Ala Leu Leu Pro Asn Leu Asn Asn Gln Gln Lys Arg
            100                 105                 110

Ala Phe Ile Arg Ser Leu Tyr Asp Asp Pro Ser Gln Ser Ala Asn Leu
        115                 120                 125

Leu Ala Glu Ala Lys Lys Leu Asn Asp Ala Gln Ala Pro Lys Gly Gly
130                 135                 140

Ser Gly Gly Asp Ser Glu Glu Ile Arg Glu Ala Phe Arg Val Phe
145                 150                 155                 160

Asp Lys Asp Gly Asp Gly Tyr Ile Ser Ala Ala Glu Leu Arg His Val
                165                 170                 175

Met Thr Asn Leu Gly Glu Lys Leu Thr Asp Glu Glu Val Asp Glu Met
            180                 185                 190

Ile Arg Glu Ala Asp Ile Asp Gly Asp Gly Gln Val Asn Tyr Glu Glu
        195                 200                 205

Phe Val Gln Met Met Thr Ala Lys
210                 215

<210> SEQ ID NO 24
<211> LENGTH: 161
<212> TYPE: PRT
<213> ORGANISM: Artificial sequence
<220> FEATURE:
<223> OTHER INFORMATION: Rat CaM-Bombesin

<400> SEQUENCE: 24

Ala Asp Gln Leu Thr Glu Glu Gln Ile Ala Glu Phe Lys Glu Ala Phe
 1               5                  10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asp Gly Thr Ile Asp
    50                  55                  60

Phe Pro Glu Phe Leu Thr Met Met Ala Arg Lys Met Lys Asp Thr Gly
 65                  70                  75                  80

Gly Asn Gln Trp Ala Val Gly His Leu Met Gly Gly Asp Ser Glu Glu
                 85                  90                  95

Glu Ile Arg Glu Ala Phe Arg Val Phe Asp Lys Asp Gly Asp Gly Tyr
            100                 105                 110

Ile Ser Ala Ala Glu Leu Arg His Val Met Thr Asn Leu Gly Glu Lys
        115                 120                 125

Leu Thr Asp Glu Glu Val Asp Glu Met Ile Arg Glu Ala Asp Ile Asp
    130                 135                 140

Gly Asp Gly Gln Val Asn Tyr Glu Glu Phe Val Gln Met Met Thr Ala
145                 150                 155                 160

Lys

<210> SEQ ID NO 25
<211> LENGTH: 164
<212> TYPE: PRT
```

<213> ORGANISM: Artificial sequence
<220> FEATURE:
<223> OTHER INFORMATION: Rat CA1-CD2-Affibody CA1-WT

<400> SEQUENCE: 25

```
Gly Ser Arg Asp Ser Gly Thr Val Trp Gly Ala Leu Gly His Gly Ile
1               5                   10                  15

Glu Leu Asn Ile Pro Asn Phe Gln Met Thr Asp Asp Ile Asp Glu Val
            20                  25                  30

Arg Trp Glu Arg Gly Ser Thr Leu Val Ala Glu Phe Lys Arg Lys Met
        35                  40                  45

Lys Pro Phe Leu Lys Ser Gly Ala Phe Glu Ile Asp Ala Asn Gly Asp
    50                  55                  60

Leu Asp Ile Lys Asn Leu Thr Arg Asp Asp Ser Gly Thr Tyr Asn Val
65                  70                  75                  80

Thr Val Tyr Ser Thr Asn Gly Thr Arg Ile Leu Asn Lys Ala Leu Asp
                85                  90                  95

Leu Arg Ile Leu Glu Gly Gly Ser Gly Gly Val Asp Asn Lys Phe Asn
            100                 105                 110

Lys Glu Gln Gln Asn Ala Phe Tyr Glu Ile Leu His Leu Pro Asn Leu
        115                 120                 125

Asn Glu Glu Gln Arg Asn Ala Phe Ile Gln Ser Leu Lys Asp Asp Pro
    130                 135                 140

Ser Gln Ser Ala Asn Leu Leu Ala Glu Ala Lys Lys Leu Asn Asp Ala
145                 150                 155                 160

Gln Ala Pro Lys
```

<210> SEQ ID NO 26
<211> LENGTH: 164
<212> TYPE: PRT
<213> ORGANISM: Artificial sequence
<220> FEATURE:
<223> OTHER INFORMATION: Rat CA1-CD2-Affibody CA1-ZHER2-4

<400> SEQUENCE: 26

```
Gly Ser Arg Asp Ser Gly Thr Val Trp Gly Ala Leu Gly His Gly Ile
1               5                   10                  15

Glu Leu Asn Ile Pro Asn Phe Gln Met Thr Asp Asp Ile Asp Glu Val
            20                  25                  30

Arg Trp Glu Arg Gly Ser Thr Leu Val Ala Glu Phe Lys Arg Lys Met
        35                  40                  45

Lys Pro Phe Leu Lys Ser Gly Ala Phe Glu Ile Asp Ala Asn Gly Asp
    50                  55                  60

Leu Asp Ile Lys Asn Leu Thr Arg Asp Asp Ser Gly Thr Tyr Asn Val
65                  70                  75                  80

Thr Val Tyr Ser Thr Asn Gly Thr Arg Ile Leu Asn Lys Ala Leu Asp
                85                  90                  95

Leu Arg Ile Leu Glu Gly Gly Ser Gly Gly Val Asp Asn Lys Phe Asn
            100                 105                 110

Lys Glu Leu Arg Gln Ala Tyr Trp Glu Ile Gln Ala Leu Pro Asn Leu
        115                 120                 125

Asn Trp Thr Gln Ser Arg Ala Phe Ile Arg Ser Leu Tyr Asp Asp Pro
    130                 135                 140

Ser Gln Ser Ala Asn Leu Leu Ala Glu Ala Lys Lys Leu Asn Asp Ala
145                 150                 155                 160

Gln Ala Pro Lys
```

<210> SEQ ID NO 27
<211> LENGTH: 164
<212> TYPE: PRT
<213> ORGANISM: Artificial sequence
<220> FEATURE:
<223> OTHER INFORMATION: Rat CA1-CD2-Affibody CA1-ZHER342

<400> SEQUENCE: 27

Gly Ser Arg Asp Ser Gly Thr Val Trp Gly Ala Leu Gly His Gly Ile
1               5                   10                  15

Glu Leu Asn Ile Pro Asn Phe Gln Met Thr Asp Asp Ile Asp Glu Val
            20                  25                  30

Arg Trp Glu Arg Gly Ser Thr Leu Val Ala Glu Phe Lys Arg Lys Met
        35                  40                  45

Lys Pro Phe Leu Lys Ser Gly Ala Phe Glu Ile Asp Ala Asn Gly Asp
    50                  55                  60

Leu Asp Ile Lys Asn Leu Thr Arg Asp Asp Ser Gly Thr Tyr Asn Val
65                  70                  75                  80

Thr Val Tyr Ser Thr Asn Gly Thr Arg Ile Leu Asn Lys Ala Leu Asp
                85                  90                  95

Leu Arg Ile Leu Glu Gly Gly Ser Gly Val Asp Asn Lys Phe Asn
            100                 105                 110

Lys Glu Met Arg Asn Ala Tyr Trp Glu Ile Ala Leu Leu Pro Asn Leu
        115                 120                 125

Asn Asn Gln Gln Lys Arg Ala Phe Ile Arg Ser Leu Tyr Asp Asp Pro
    130                 135                 140

Ser Gln Ser Ala Asn Leu Leu Ala Glu Ala Lys Lys Leu Asn Asp Ala
145                 150                 155                 160

Gln Ala Pro Lys

<210> SEQ ID NO 28
<211> LENGTH: 115
<212> TYPE: PRT
<213> ORGANISM: Artificial sequence
<220> FEATURE:
<223> OTHER INFORMATION: Rat CA1-CD2-Bombesin (C-terminal)

<400> SEQUENCE: 28

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Ser Gly Asn Gln Trp Ala Val Gly
            100                 105                 110

His Leu Met
        115

<210> SEQ ID NO 29

```
<211> LENGTH: 119
<212> TYPE: PRT
<213> ORGANISM: Artificial sequence
<220> FEATURE:
<223> OTHER INFORMATION: Rat CA1-CD2-Bombesin (52I)

<400> SEQUENCE: 29

Arg Asp Ser Gly Thr Val Trp Gly Ala Leu Gly His Gly Ile Glu Leu
1               5                   10                  15

Asn Ile Pro Asn Phe Gln Met Thr Asp Ile Asp Glu Val Arg Trp
            20                  25                  30

Glu Arg Gly Ser Thr Leu Val Ala Glu Phe Lys Arg Lys Met Lys Pro
            35                  40                  45

Phe Leu Lys Ser Gly Gly Ser Gly Gly Gly Asn Gln Trp Ala Val Gly
        50                  55                  60

His Leu Met Gly Gly Ser Gly Gly Gly Ala Phe Glu Ile Asp Ala Asn
65                  70                  75                  80

Gly Asp Leu Asp Ile Lys Asn Leu Thr Arg Asp Asp Ser Gly Thr Tyr
                85                  90                  95

Asn Val Thr Val Tyr Ser Thr Asn Gly Thr Arg Ile Leu Asn Lys Ala
            100                 105                 110

Leu Asp Leu Arg Ile Leu Glu
        115

<210> SEQ ID NO 30
<211> LENGTH: 110
<212> TYPE: PRT
<213> ORGANISM: Artificial sequence
<220> FEATURE:
<223> OTHER INFORMATION: Rat Parvalbumin WT

<400> SEQUENCE: 30

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
            35                  40                  45

His Ile Leu Asp Lys Asp Lys Ser Gly Phe Ile Glu Glu Asp Glu Leu
        50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Phe Ser Thr Leu Val Ala Glu Ser
            100                 105                 110

<210> SEQ ID NO 31
<211> LENGTH: 110
<212> TYPE: PRT
<213> ORGANISM: Artificial sequence
<220> FEATURE:
<223> OTHER INFORMATION: S56D

<400> SEQUENCE: 31

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30
```

```
Met Val Gly Leu Lys Lys Lys Ser Ala Asp Asp Val Lys Lys Val Phe
             35                  40                  45

His Ile Leu Asp Lys Asp Lys Asp Gly Phe Ile Glu Glu Asp Glu Leu
 50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                 85                  90                  95

Lys Ile Gly Val Glu Glu Phe Ser Thr Leu Val Ala Glu Ser
                100                 105                 110

<210> SEQ ID NO 32
<211> LENGTH: 110
<212> TYPE: PRT
<213> ORGANISM: Artificial sequence
<220> FEATURE:
<223> OTHER INFORMATION: S56D-F103W

<400> SEQUENCE: 32

Met Ser Met Thr Asp Leu Leu Ser Ala Glu Asp Ile Lys Lys Ala Ile
 1               5                  10                  15

Gly Ala Phe Thr Ala Ala Asp Ser Phe Asp His Lys Lys Phe Phe Gln
                 20                  25                  30

Met Val Gly Leu Lys Lys Lys Ser Ala Asp Asp Val Lys Lys Val Phe
             35                  40                  45

His Ile Leu Asp Lys Asp Lys Asp Gly Phe Ile Glu Glu Asp Glu Leu
 50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                 85                  90                  95

Lys Ile Gly Val Glu Glu Trp Ser Thr Leu Val Ala Glu Ser
                100                 105                 110

<210> SEQ ID NO 33
<211> LENGTH: 110
<212> TYPE: PRT
<213> ORGANISM: Artificial sequnce
<220> FEATURE:
<223> OTHER INFORMATION: E60D

<400> SEQUENCE: 33

Met Ser Met Thr Asp Leu Leu Ser Ala Glu Asp Ile Lys Lys Ala Ile
 1               5                  10                  15

Gly Ala Phe Thr Ala Ala Asp Ser Phe Asp His Lys Lys Phe Phe Gln
                 20                  25                  30

Met Val Gly Leu Lys Lys Lys Ser Ala Asp Asp Val Lys Lys Val Phe
             35                  40                  45

His Ile Leu Asp Lys Asp Lys Ser Gly Phe Ile Asp Glu Asp Glu Leu
 50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                 85                  90                  95

Lys Ile Gly Val Glu Glu Phe Ser Thr Leu Val Ala Glu Ser
                100                 105                 110

<210> SEQ ID NO 34
```

```
<211> LENGTH: 110
<212> TYPE: PRT
<213> ORGANISM: Artificial sequence
<220> FEATURE:
<223> OTHER INFORMATION: S56D-F103W

<400> SEQUENCE: 34

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Asp Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser
            100                 105                 110

<210> SEQ ID NO 35
<211> LENGTH: 110
<212> TYPE: PRT
<213> ORGANISM: Artificial sequence
<220> FEATURE:
<223> OTHER INFORMATION: G99D

<400> SEQUENCE: 35

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Asp Val Glu Glu Phe Ser Thr Leu Val Ala Glu Ser
            100                 105                 110

<210> SEQ ID NO 36
<211> LENGTH: 110
<212> TYPE: PRT
<213> ORGANISM: Artificial sequence
<220> FEATURE:
<223> OTHER INFORMATION: G99D-F103W

<400> SEQUENCE: 36

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45
```

His Ile Leu Asp Lys Asp Lys Ser Gly Phe Ile Glu Glu Asp Glu Leu
        50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                85                  90                  95

Lys Ile Asp Val Glu Glu Trp Ser Thr Leu Val Ala Glu Ser
                100                 105                 110

<210> SEQ ID NO 37
<211> LENGTH: 110
<212> TYPE: PRT
<213> ORGANISM: Artificial sequence
<220> FEATURE:
<223> OTHER INFORMATION: D53S-F103W

<400> SEQUENCE: 37

Met Ser Met Thr Asp Leu Leu Ser Ala Glu Asp Ile Lys Lys Ala Ile
 1               5                  10                  15

Gly Ala Phe Thr Ala Ala Asp Ser Phe Asp His Lys Lys Phe Phe Gln
                20                  25                  30

Met Val Gly Leu Lys Lys Lys Ser Ala Asp Asp Val Lys Lys Val Phe
                35                  40                  45

His Ile Leu Ser Lys Asp Lys Ser Gly Phe Ile Glu Glu Asp Glu Leu
        50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                85                  90                  95

Lys Ile Asp Val Glu Glu Trp Ser Thr Leu Val Ala Glu Ser
                100                 105                 110

<210> SEQ ID NO 38
<211> LENGTH: 110
<212> TYPE: PRT
<213> ORGANISM: Artificial sequence
<220> FEATURE:
<223> OTHER INFORMATION: D53E-F103W

<400> SEQUENCE: 38

Met Ser Met Thr Asp Leu Leu Ser Ala Glu Asp Ile Lys Lys Ala Ile
 1               5                  10                  15

Gly Ala Phe Thr Ala Ala Asp Ser Phe Asp His Lys Lys Phe Phe Gln
                20                  25                  30

Met Val Gly Leu Lys Lys Lys Ser Ala Asp Asp Val Lys Lys Val Phe
                35                  40                  45

His Ile Leu Glu Lys Asp Lys Ser Gly Phe Ile Glu Glu Asp Glu Leu
        50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                85                  90                  95

Lys Ile Asp Val Glu Glu Trp Ser Thr Leu Val Ala Glu Ser
                100                 105                 110

<210> SEQ ID NO 39
<211> LENGTH: 111
<212> TYPE: PRT
<213> ORGANISM: Artificial sequence

<220> FEATURE:
<223> OTHER INFORMATION: F103WC104

<400> SEQUENCE: 39

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Cys
            100                 105                 110

<210> SEQ ID NO 40
<211> LENGTH: 110
<212> TYPE: PRT
<213> ORGANISM: Artificial sequence
<220> FEATURE:
<223> OTHER INFORMATION: F103W

<400> SEQUENCE: 40

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser
            100                 105                 110

<210> SEQ ID NO 41
<211> LENGTH: 110
<212> TYPE: PRT
<213> ORGANISM: Artificial sequence
<220> FEATURE:
<223> OTHER INFORMATION: Human parvalbumin

<400> SEQUENCE: 41

Met Ser Met Thr Asp Leu Leu Asn Ala Glu Asp Ile Lys Lys Ala Val
1               5                   10                  15

Gly Ala Phe Ser Ala Thr Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Met Leu Asp Lys Asp Lys Ser Gly Phe Ile Glu Glu Asp Glu Leu
    50                  55                  60

```
Gly Phe Ile Leu Lys Gly Phe Ser Pro Asp Ala Arg Asp Leu Ser Ala
 65                  70                  75                  80

Lys Glu Thr Lys Met Leu Met Ala Ala Gly Asp Lys Asp Gly Asp Gly
                 85                  90                  95

Lys Ile Gly Val Asp Glu Phe Ser Thr Leu Val Ala Glu Ser
            100                 105                 110

<210> SEQ ID NO 42
<211> LENGTH: 130
<212> TYPE: PRT
<213> ORGANISM: Artificial sequence
<220> FEATURE:
<223> OTHER INFORMATION: PV collagen

<400> SEQUENCE: 42

Met Ser Met Thr Asp Leu Leu Ser Ala Glu Asp Ile Lys Lys Ala Ile
 1               5                  10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Val Lys Lys Val Phe
            35                  40                  45

His Ile Leu Asp Lys Asp Lys Asp Gly Phe Ile Glu Glu Asp Glu Leu
 50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                 85                  90                  95

Lys Ile Gly Val Glu Glu Trp Ser Thr Leu Val Ala Glu Ser Gly Gly
            100                 105                 110

Gly Lys Lys Trp His Cys Tyr Thr Tyr Phe Pro His His Tyr Cys Val
            115                 120                 125

Tyr Gly
    130

<210> SEQ ID NO 43
<211> LENGTH: 122
<212> TYPE: PRT
<213> ORGANISM: Artificial sequence
<220> FEATURE:
<223> OTHER INFORMATION: PV bombesin

<400> SEQUENCE: 43

Met Ser Met Thr Asp Leu Leu Ser Ala Glu Asp Ile Lys Lys Ala Ile
 1               5                  10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Val Lys Lys Val Phe
            35                  40                  45

His Ile Leu Asp Lys Asp Lys Asp Gly Phe Ile Glu Glu Asp Glu Leu
 50                  55                  60

Gly Ser Ile Leu Lys Gly Phe Ser Ser Asp Ala Arg Asp Leu Ser Ala
 65                  70                  75                  80

Lys Glu Thr Lys Thr Leu Met Ala Ala Gly Asp Lys Asp Gly Asp Gly
                 85                  90                  95

Lys Ile Gly Val Glu Glu Trp Ser Thr Leu Val Ala Glu Ser Gly Gly
            100                 105                 110

Gly Ala Gln Trp Ala Val Gly His Leu Met
            115                 120
```

```
<210> SEQ ID NO 44
<211> LENGTH: 129
<212> TYPE: PRT
<213> ORGANISM: Artificial sequence
<220> FEATURE:
<223> OTHER INFORMATION: PV Selectin

<400> SEQUENCE: 44
```

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Gly Gly
            100                 105                 110

Gly Lys Tyr Asp Gly Asp Ile Thr Trp Asp Gln Leu Trp Asp Leu Met
        115                 120                 125

Lys

```
<210> SEQ ID NO 45
<211> LENGTH: 125
<212> TYPE: PRT
<213> ORGANISM: Artificial sequence
<220> FEATURE:
<223> OTHER INFORMATION: PV RGD

<400> SEQUENCE: 45
```

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Gly Gly
            100                 105                 110

Gly Arg Gly Asp Arg Gly Asp Arg Gly Asp Arg Gly Asp
        115                 120                 125

```
<210> SEQ ID NO 46
<211> LENGTH: 111
<212> TYPE: PRT
<213> ORGANISM: Artificial sequence
<220> FEATURE:
<223> OTHER INFORMATION: PV Cys
```

-continued

<400> SEQUENCE: 46

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Cys
            100                 105                 110

<210> SEQ ID NO 47
<211> LENGTH: 173
<212> TYPE: PRT
<213> ORGANISM: Artificial sequence
<220> FEATURE:
<223> OTHER INFORMATION: PV Affibody

<400> SEQUENCE: 47

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Gly Gly
            100                 105                 110

Ser Gly Gly Val Asp Asn Lys Phe Asn Lys Glu Met Arg Asn Ala Tyr
            115                 120                 125

Trp Glu Ile Ala Leu Leu Pro Asn Leu Asn Asn Gln Gln Lys Arg Ala
        130                 135                 140

Phe Ile Arg Ser Leu Tyr Asp Asp Pro Ser Gln Ser Ala Asn Leu Leu
145                 150                 155                 160

Ala Glu Ala Lys Lys Leu Asn Asp Ala Gln Ala Pro Lys
                165                 170

<210> SEQ ID NO 48
<211> LENGTH: 79
<212> TYPE: PRT
<213> ORGANISM: Artificial sequence
<220> FEATURE:
<223> OTHER INFORMATION: Human calbindin D9K

<400> SEQUENCE: 48

Met Ser Thr Lys Lys Ser Pro Glu Glu Leu Lys Arg Ile Phe Glu Lys
1               5                   10                  15

```
Tyr Ala Ala Lys Glu Gly Asp Pro Asp Gln Leu Ser Lys Asp Glu Leu
            20                  25                  30

Lys Leu Leu Ile Gln Ala Glu Phe Pro Ser Leu Leu Lys Gly Pro Asn
        35                  40                  45

Thr Leu Asp Asp Leu Phe Gln Glu Leu Asp Lys Asn Gly Asp Gly Glu
    50                  55                  60

Val Ser Phe Glu Glu Phe Gln Val Leu Val Lys Lys Ile Ser Gln
65                  70                  75

<210> SEQ ID NO 49
<211> LENGTH: 79
<212> TYPE: PRT
<213> ORGANISM: Artificial sequence
<220> FEATURE:
<223> OTHER INFORMATION: CalbindinD9kF67W

<400> SEQUENCE: 49

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
            20                  25                  30

Lys Leu Leu Ile Gln Ala Glu Phe Pro Ser Leu Leu Lys Gly Pro Asn
        35                  40                  45

Thr Leu Asp Asp Leu Phe Gln Glu Leu Asp Lys Asn Gly Asp Gly Glu
    50                  55                  60

Val Ser Phe Glu Glu Trp Gln Val Leu Val Lys Lys Ile Ser Gln
65                  70                  75

<210> SEQ ID NO 50
<211> LENGTH: 79
<212> TYPE: PRT
<213> ORGANISM: Artificial sequence
<220> FEATURE:
<223> OTHER INFORMATION: CalbindinD9kP43M

<400> SEQUENCE: 50

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
            20                  25                  30

Lys Leu Leu Ile Gln Ala Glu Phe Pro Ser Leu Leu Lys Gly Met Asn
        35                  40                  45

Thr Leu Asp Asp Leu Phe Gln Glu Leu Asp Lys Asn Gly Asp Gly Glu
    50                  55                  60

Val Ser Phe Glu Glu Trp Gln Val Leu Val Lys Lys Ile Ser Gln
65                  70                  75

<210> SEQ ID NO 51
<211> LENGTH: 80
<212> TYPE: PRT
<213> ORGANISM: Artificial sequence
<220> FEATURE:
<223> OTHER INFORMATION: CalbindinD9kCys

<400> SEQUENCE: 51

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
            20                  25                  30

Lys Leu Leu Ile Gln Ala Glu Phe Pro Ser Leu Leu Lys Gly Pro Asn
```

```
                35                  40                  45
Thr Leu Asp Asp Leu Phe Gln Glu Leu Asp Lys Asn Gly Asp Gly Glu
 50                  55                  60

Val Ser Phe Glu Glu Phe Gln Val Leu Val Lys Lys Ile Ser Gln Cys
65                  70                  75                  80

<210> SEQ ID NO 52
<211> LENGTH: 160
<212> TYPE: PRT
<213> ORGANISM: Artificial sequence
<220> FEATURE:
<223> OTHER INFORMATION: Human-Troponin

<400> SEQUENCE: 52

Met Thr Asp Gln Gln Ala Glu Ala Arg Ser Tyr Leu Ser Glu Glu Met
1               5                   10                  15

Ile Ala Glu Phe Lys Ala Ala Phe Asp Met Phe Asp Ala Asp Gly Gly
                20                  25                  30

Gly Asp Ile Ser Val Lys Glu Leu Gly Thr Val Met Arg Met Leu Gly
            35                  40                  45

Gln Thr Pro Thr Lys Glu Glu Leu Asp Ala Ile Ile Glu Glu Val Asp
 50                  55                  60

Glu Asp Gly Ser Gly Thr Ile Asp Phe Glu Glu Phe Leu Val Met Met
65                  70                  75                  80

Val Arg Gln Met Lys Glu Asp Ala Lys Gly Lys Ser Glu Glu Glu Leu
                85                  90                  95

Ala Glu Cys Phe Arg Ile Phe Asp Arg Asn Ala Asp Gly Tyr Ile Asp
            100                 105                 110

Pro Gly Glu Leu Ala Glu Ile Phe Arg Ala Ser Gly Glu His Val Thr
        115                 120                 125

Asp Glu Glu Ile Glu Ser Leu Met Lys Asp Gly Asp Lys Asn Asn Asp
    130                 135                 140

Gly Arg Ile Asp Phe Asp Glu Phe Leu Lys Met Met Glu Gly Val Gln
145                 150                 155                 160

<210> SEQ ID NO 53
<211> LENGTH: 122
<212> TYPE: PRT
<213> ORGANISM: Artificial sequence
<220> FEATURE:
<223> OTHER INFORMATION: Rat CA1-CD2-Bombesin-RGD (52I)-Cend

<400> SEQUENCE: 53

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Gly Ser Gly Gly Gly Asn Gln Trp Ala Val Gly
        50                  55                  60

His Leu Met Gly Gly Ser Gly Gly Gly Ala Phe Glu Ile Asp Ala Asn
65                  70                  75                  80

Gly Asp Leu Asp Ile Lys Asn Leu Thr Arg Asp Asp Ser Gly Thr Tyr
                85                  90                  95

Asn Val Thr Val Tyr Ser Thr Asn Gly Thr Arg Ile Leu Asn Lys Ala
            100                 105                 110
```

-continued

```
Leu Asp Leu Arg Ile Leu Glu Arg Gly Asp
        115                 120

<210> SEQ ID NO 54
<211> LENGTH: 122
<212> TYPE: PRT
<213> ORGANISM: Artificial sequence
<220> FEATURE:
<223> OTHER INFORMATION: Rat CA1-CD2-Bombesin-RGD (52I)-Nend

<400> SEQUENCE: 54

Arg Gly Asp Arg Asp Ser Gly Thr Val Trp Gly Ala Leu Gly His Gly
1               5                   10                  15

Ile Glu Leu Asn Ile Pro Asn Phe Gln Met Thr Asp Asp Ile Asp Glu
            20                  25                  30

Val Arg Trp Glu Arg Gly Ser Thr Leu Val Ala Glu Phe Lys Arg Lys
        35                  40                  45

Met Lys Pro Phe Leu Lys Ser Gly Ser Gly Gly Gly Asn Gln Trp
    50                  55                  60

Ala Val Gly His Leu Met Gly Gly Ser Gly Gly Ala Phe Glu Ile
65                  70                  75                  80

Asp Ala Asn Gly Asp Leu Asp Ile Lys Asn Leu Thr Arg Asp Ser
                85                  90                  95

Gly Thr Tyr Asn Val Thr Val Tyr Ser Thr Asn Gly Thr Arg Ile Leu
            100                 105                 110

Asn Lys Ala Leu Asp Leu Arg Ile Leu Glu
        115                 120

<210> SEQ ID NO 55
<211> LENGTH: 113
<212> TYPE: PRT
<213> ORGANISM: Artificial sequence
<220> FEATURE:
<223> OTHER INFORMATION: Rat CA1-CD2-RGD-83I

<400> SEQUENCE: 55

Arg Asp Ser Gly Thr Val Trp Gly Ala Leu Gly His Gly Ile Glu Leu
1               5                   10                  15

Asn Ile Pro Asn Phe Gln Met Thr Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Ser Gly Thr Tyr Asn Val Thr Val
65                  70                  75                  80

Tyr Ser Thr Gly Gly Ser Gly Gly Arg Gly Asp Gly Ser Gly Gly
                85                  90                  95

Asn Gly Thr Arg Ile Leu Asn Lys Ala Leu Asp Leu Arg Ile Leu Glu
            100                 105                 110

Gly

<210> SEQ ID NO 56
<211> LENGTH: 135
<212> TYPE: PRT
<213> ORGANISM: Artificial sequence
<220> FEATURE:
<223> OTHER INFORMATION: Rat CA1-CD2-Bom-52I-RGD-83I

<400> SEQUENCE: 56
```

-continued

```
Arg Gly Asp Arg Asp Ser Gly Thr Val Trp Gly Ala Leu Gly His Gly
1               5                   10                  15

Ile Glu Leu Asn Ile Pro Asn Phe Gln Met Thr Asp Asp Ile Asp Glu
                20              25                  30

Val Arg Trp Glu Arg Gly Ser Thr Leu Val Ala Glu Phe Lys Arg Lys
        35                  40              45

Met Lys Pro Phe Leu Lys Ser Gly Gly Ser Gly Gly Gly Asn Gln Trp
    50              55                  60

Ala Val Gly His Leu Met Gly Gly Ser Gly Gly Gly Ala Phe Glu Ile
65              70                  75                  80

Asp Ala Asn Gly Asp Leu Asp Ile Lys Asn Leu Thr Arg Asp Asp Ser
                85              90                  95

Gly Thr Tyr Asn Val Thr Val Tyr Ser Thr Gly Gly Ser Gly Gly Arg
            100             105             110

Gly Asp Gly Gly Ser Gly Gly Asn Gly Thr Arg Ile Leu Asn Lys Ala
        115             120                 125

Leu Asp Leu Arg Ile Leu Glu
130                 135
```

CONTRAST AGENTS, METHODS FOR PREPARING CONTRAST AGENTS, AND METHODS OF IMAGING

CROSS-REFERENCE TO RELATED APPLICATIONS

This application is the 35 U.S.C. § 371 national stage of PCT Application No. PCT/US2013/044292, filed Jun. 5, 2013, which is entirely incorporated herein by reference and which also claims priority to, and the benefit of, U.S. Provisional Patent Application Ser. No. 61/655,575 entitled "CONTRAST AGENTS, METHODS FOR PREPARING CONTRAST AGENTS, AND METHODS OF IMAGING" and filed Jun. 5, 2012, and to U.S. Provisional Patent Application Ser. No. 61/818,516 entitled "CONTRAST AGENTS, METHODS FOR PREPARING CONTRAST AGENTS, AND METHODS OF IMAGING" and filed May 2, 2013, the entireties of which are hereby incorporated by reference.

SEQUENCE LISTING

The present disclosure includes a sequence listing incorporated herein by reference in its entirety.

FIELD OF THE DISCLOSURE

This disclosure relates to the field of protein contrast agents useful for providing enhanced MRI detection of targeted tissues. In particular, the disclosure relates to probes and methods of use for obtaining enhanced images of tumors in a human or non-human animal.

BACKGROUND

Cancer is a deadly disease causes more 500,000 deaths annually in the United States. Although huge effects have been made, the cancer therapy is restricted by still lack of effective and reliable methods for early diagnostics and evaluation of tumor biomarkers. Therefore, it is critical to develop an effective way to detect the tumor and its biomarkers in the early stage.
Multiple approaches are applied for the tumor diagnostics. These methods include screening blood circulating biomarkers, biopsy, and various imaging techniques. The blood circulating biomarkers hold great potential for the tumor diagnostics. In the current stage, however, it lacks sensitivity and specificity. For example, the PSA test, a standard for prostate cancer diagnostics, has a low correlation with prostate cancer staging. Biopsy is an informative method. However, this method is extremely invasive. The patients have to suffer from the great pain before the tissues are taken out from the body for the analysis. The "golden-standard" the evaluation of angiogenesis is the mean vascular density (MVD), which estimates the blood vessel density by IHC. However, tumor is usually heterogeneous, and MVD only quantify limited area in the collected tissues in the specific location of the tumor. Thus, the MVD of biopsy tissue can be misleading.[64, 69] On the other hands, imaging techniques are used to detect angiogenesis. However, most of these techniques are not satisfied with the requirement for the tumor diagnostics. The fluorescence imaging lacks of the tissue penetration. The sensitive imaging techniques such as PET and SPECT are expensive, and the number of PET and SPECT scanner is limited. Besides, PET and SPECT imaging use radioactive isotopes, which could be potentially harmful to the patients.[64]

MRI is one of the promising techniques for the cancer diagnostics. Magnetic renascence Imaging (MRI) is an advanced diagnostic technique with high resolution, three dimensional properties. Limited by the low sensitivity, 30% of the MRI tests require the administration of MRI contrast agents to improve the signal-to-noise ratio and obtain tissue-specific images.[26] With 7 unpaired protons, high magnetic moment and long election relaxation time, $Gd^{3+}$ became the best metal ion function as contrast agents. $Gd^{3+}$-based MRI contrast agents were applied for current clinically available diagnostics for over two decades.

The low sensitivity of MRI contrast agents limits the application of this technique for molecular imaging. To image the biomarkers with limited receptor number, MRI contrast agents must be incorporated with targeting moieties and have high relaxivity. Unfortunately, most of the current contrast agent only has relatively low relaxivity (less than 5 $s^{-1}$ $mM^{-1}$ for Gd-DTPA), and the lowest detection limits for these contrast agents are 0.1 mM. Therefore, it is hard to image the expression level of certain receptors when the receptor number is low. On the other hand, to targeting to the receptors, these contrast agents are usually conjugated to antibodies or peptides. Unfortunately, even single chain antibody has a large molecular weight and contrast agents conjugated with antibodies have low penetration to tumor tissue.[34] Protein-based contrast agents have more than 10 fold higher relaxivity than that of the current clinically available MRI contrast agents. By conjugating to small peptides or affibody, ProCA1s is able to image biomarkers, such as HER-2 and GRPR.

SUMMARY

The disclosure encompasses embodiments of a protein contrast agent for enhancing an MRI image, the protein contrast agent comprising: (i) a polypeptide having a conformation presenting at least five oxygen atoms positioned to chelate at least one paramagnetic metal ion selected from the group consisting of $Gd^{3+}$, $Eu^{3+}$, $Tm^{3+}$, $Yb^{3+}$, $Lu^{3+}$, $Mn^{2+}$, and $Fe^{3+}$, and wherein (a) each oxygen atom interacting with the metal ion can be between about 2 angstrom units and about 5 angstrom units from the metal ion; (b) the metal ion can have at least one water molecule electrostatically interacting therewith and at a distance of less than about 10 angstrom units therefrom, and wherein the polypeptide can include a target-specific moiety attached thereto; (ii) at least one polyethylene glycol molecule attached to the polypeptide; and (iii) at least one paramagnetic metal ion chelated to the polypeptide, wherein the protein contrast agent, when administered to a human or non-human animal can provide an enhanced MRI image allowing the determination of a T2/T1 or T1/T2 MRI intensity ratio, and wherein the metal ion or ions can be chelated to a beta-fold region of the polypeptide or at least one loop and an alpha-helix, wherein the protein contrast agent can provide an image of a tumor having a size less than about 0.25 microns, and wherein the target-specific moiety can be specific for a cell-specific target selected from the group consisting of: a hepatic tumor, a renal tumor, and a cardiovascular-specific target, and wherein the protein contrast agent can have an amino acid sequence having at least 85% similarity to a sequence selected from the group consisting of: SEQ ID Nos.: 1-22, or conservative variants thereof.

Another aspect of the disclosure encompasses embodiments of a pharmaceutically acceptable composition formulated for administration to a human or non-human animal for use as an MRI imaging contrast agent, said composition comprising a protein contrast agent having an amino acid sequence having at least 85% similarity to a sequence selected from the group consisting of: SEQ ID Nos.: 1-22, or conservative variants.

Another aspect of the disclosure encompasses embodiments of a method of obtaining an MRI image of a tissue, said method comprising the steps: (a) administering to a human or non-human animal a pharmaceutically acceptable dose of a protein contrast agent, wherein said protein contrast agent comprises: (i) a polypeptide having a conformation presenting at least five oxygen atoms positioned to chelate at least one paramagnetic metal ion selected from the group consisting of $Gd^{3+}$, $Eu^{3+}$, $Tm^{3+}$, $Yb^{3+}$, $Lu^{3+}$, $Mn^{2+}$, and $Fe^{3+}$, and wherein (a) each oxygen atom interacting with the metal ion is between about 2 angstrom units and about 5 angstrom units from the metal ion; (b) the metal ion has at least one water molecule electrostatically interacting therewith and at a distance of less than about 10 angstrom units therefrom, and wherein the polypeptide includes a target-specific moiety conjugated thereto; (ii) at least one polyethylene glycol molecule attached to the polypeptide; (iii) at least one paramagnetic metal ion chelated to the polypeptide; and (iv) a pharmaceutically acceptable carrier; (b) subjecting the human or non-human animal to MRI, thereby obtaining a T1 and a T2 determination; (c) determining the T2/T1 or T1/T2 intensity ratio of the MRI image; and (d) obtaining an image of the T2/T1 or T1/T2 intensity ratio relative to a tissue of the human or non-human animal, thereby determining the location of the protein contrast agent in the human or non-human animal, thereby identifying a target tissue.

Still another aspect of the disclosure encompasses embodiments of a method of producing a protein contrast agent, said method comprising the steps of: (a) obtaining a genetically modified cell comprising an expression vector expressing a polypeptide having an amino acid sequence selected from the group consisting of: SEQ ID Nos.: 1-56, or a conservative variant thereof; (b) culturing said genetically modified cell in a culture medium under conditions allowing the expression of the polypeptide by cultured cells; (c) isolating the cultured cells from the medium and disrupting said isolated cell thereby generating a cell lysate; (d) separating cell debris from the cell lysate; and (e) incubating the cell lysate at 80-100° C. for about 5-20 min, centrifuging to obtain a supernatant, and either (i) precipitating undesired proteins using streptomycin, polyethylene glycol, or ammonium sulfate, and isolating the protein contrast agent by ion exchange column.

BRIEF DESCRIPTION OF THE DRAWINGS

Many aspects of the disclosure can be better understood with reference to the following drawings.

FIGS. 1A-1E illustrate the amino acid sequences SEQ ID Nos.: 1-56 of the disclosure. Target-specific moieties are double underlined and linkers are single underlined. Amino acids providing side-chain oxygens binding to metal ions are indicated in bold and by vertical arrows.

FIG. 2 illustrates a western blot of ProCA32 after incubation with serum at 37° C. for 0 h, 2 h, 6 d, 8 d, 10 d, 12 d. ProCA32 still existed in the blood serum even after 12 days without any cleavage, which indicate our contrast agent is very stable in vivo.

FIG. 3 illustrates the binding affinity and metal selectivity of ProCA3 variants and Gd-DTPA.

Figure 4:
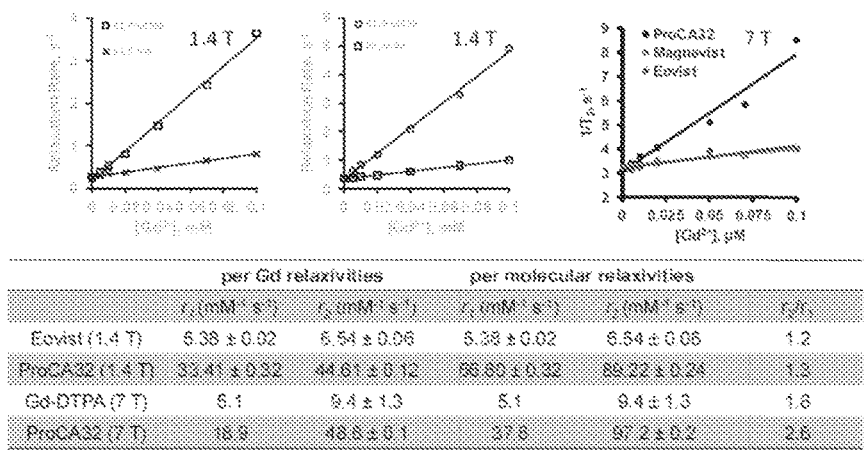
FIG. 4 illustrates that ProCA32 has high r1 and r2 relaxivities

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

Protein Contrast Agent, ProCA

Definitions

In describing and claiming the disclosed subject matter, the following terminology will be used in accordance with the definitions set forth below.

The term "contrast agent" as used herein refers to any agent that is physiologically tolerable and capable of providing enhanced contrast for magnetic resonance imaging. A suitable contrast agent is preferably biocompatible, e.g., non-toxic, chemically stable, not absorbed by the body or reactive with a tissue, and eliminated from the body within a short time.

The term "polymer" as used herein refers to any compound that is made up of two or more monomeric units covalently bonded to each other, where the monomeric units may be the same or different, such that the polymer may be a homopolymer or a heteropolymer. Representative polymers include, but are not limited to, peptides, polysaccharides, nucleic acids and the like, where the polymers may be naturally occurring or synthetic.

The term "polypeptide" as used herein includes proteins and fragments thereof. Polypeptides are disclosed herein as amino acid residue sequences. Those sequences are written left to right in the direction from the amino to the carboxy terminus. In accordance with standard nomenclature, amino acid residues (both D and L stereoisomers thereof) are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

The term "variant" as used herein refers to a polypeptide or polynucleotide or polymer that differs from a reference polypeptide or polynucleotide or polymer, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

A variant of a polypeptide may contain different modifications such as with PEGylation groups or the same type of groups with different sizes or lengths of the modifications.

"Variant" generated such as by modifying metal binding sites may have different metal binding properties and relaxivities and in vivo properties.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties. Modifications may also include PEGylation with PEG-chains, and the like.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, the polypeptides of the disclosure can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST and XBLAST). The default parameters are used to determine the identity of the polypeptides of the present disclosure.

By way of example, a polypeptide sequence may be identical to the reference sequence, that is 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in *Xenopus oocytes* by microinjection of mutated mRNA and chemically aminoacylated suppressor tRNAs (Turcatti, et al., J. Biol. Chem., 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.*, 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotide encompasses the terms "nucleic acid," "nucleic acid sequence," or "oligonucleotide" as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alias.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain. Codons correspond to specific amino acids (as defined by the transfer RNAs) or to start and stop of translation by the ribosome.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

The term "antibody" is used to refer both to a homogenous molecular entity, or a mixture such as a serum product made up of a plurality of different molecular entities. Monoclonal or polyclonal antibodies may be made by methods known in the art (e.g., Harlow & Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987)).

Affibody® ligands (U.S. Pat. No. 5,831,012, which is incorporated herein by reference) are highly specific affinity proteins that may be designed and used like aptamers. Affibodies may be produced or purchased from commercial sources (Affibody AB, Bromma, Sweden). Aptamers and affibodies may be used in combination with antibodies to increase the functional avidity of translucent or non-translucent solid matrices for probe molecule binding. Increased binding in turn results in an increased signal strength, greater signal-to-noise ratio, more reproducible target molecule detection and greater sensitivity of detection.

Aptamers must also be differentiated from the naturally occurring nucleic acid sequences that bind to certain proteins. These latter sequences generally are naturally occurring sequences embedded within the genome of the organism that bind to a specialized sub-group of proteins or polypeptides, or their derivatives, that are involved in the transcription, translation, and transportation of naturally occurring nucleic acids, i.e., protein-binding nucleic acids. Aptamers on the other hand are short, isolated, non-naturally occurring nucleic acid molecules. While aptamers can be identified that bind nucleic acid-binding proteins, in most cases such aptamers have little or no sequence identity to the sequences recognized by the nucleic acid-binding proteins in nature. More importantly, aptamers can be selected to bind virtually any protein (not just nucleic acid-binding proteins)

as well as almost any target of interest including small molecules, carbohydrates, peptides, etc. For most targets, even proteins, a naturally occurring nucleic acid sequence to which it binds does not exist. For those targets that do have such a sequence, i.e., nucleic acid-binding proteins, such sequences will differ from aptamers as a result of the relatively low binding affinity used in nature as compared to tightly binding aptamers. Aptamers are capable of specifically binding to selected targets and modulating the target's activity or binding interactions, e.g., through binding, aptamers may block their target's ability to function. The functional property of specific binding to a target is an inherent property of an aptamer.

A typical aptamer is 6-35 kDa in size (20-100 nucleotides), binds its target with micromolar to sub-nanomolar affinity, and may discriminate against closely related targets (e.g., aptamers may selectively bind related proteins from the same gene family). Aptamers are capable of using intermolecular interactions such as hydrogen bonding, electrostatic complementarities, hydrophobic contacts, and steric exclusion to bind with a specific target. In the present disclosure, aptamers also employ boronic acid-Lewis base/nucleophile (such as hydroxyl groups, diols, and amino groups) interactions for binding. Aptamers have a number of desirable characteristics for use as therapeutics and diagnostics including high specificity and affinity, low immunogenicity, biological efficacy, and excellent pharmacokinetic properties.

As used herein, the term "PEGylation" means and refers to modifying a polypeptide or polynucleotide by covalently attaching polyethylene glycol (PEG) to said polypeptide or polynucleotide, with "PEGylated" referring to a polypeptide having a PEG attached. For further general information on PEGylation methods see, for example, the Nektar Advanced PEGylation Catalogs 2004 and 2005-2006, as well as the references cited therein. PEGylation can be achieved by non-specific interaction with functional group of polypeptide chain such as via amino group or specific interaction at certain location of the macromolecules such as amino terminal or at the Cys residues.

The terms "biomarker" or "biomarker probe" are used to refer to a substance used as an indicator of a biologic state. It is a characteristic that is objectively measured and evaluated as an indicator of normal biologic processes, pathogenic processes, and/or pharmacologic responses to a therapeutic intervention.

The term "disease marker" is used to refer to substances, such as proteins, bio-chemicals, nucleic acids, carbohydrates, or enzymes, produced by disease cells or by the body in response to disease cells during disease development and progression. These substances are indicative of a particular disease process.

By "administration" is meant introducing a compound into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of a contrast agent including a compound to provide a pharmacologic effect, even in the absence of a disease or condition. For example, "treatment" encompasses delivery of a disease or pathogen compound via the contrast agent that provides for enhanced or desirable effects in the subject (e.g., reduction of pathogen load, reduction of disease symptoms, etc.).

As used herein, the terms "prophylactically treat" or "prophylactically treating" refers to completely or partially preventing a disease or symptom thereof and/or may be therapeutic in terms of a partial or complete cure for a disease and/or adverse effect attributable to the disease.

The term "unit dosage form," as used herein, refers to physically discrete units suitable as unitary dosages for human and/or animal subjects, each unit containing a predetermined quantity of a contrast agent calculated in an amount sufficient to produce the desired effect in association with a pharmaceutically acceptable diluent, carrier or vehicle. The specifications for unit dosage forms depend on the particular compound employed, the route and frequency of administration, the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

As used herein, a "pharmaceutical composition" is meant to encompass a contrast agent suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "therapeutically effective amount" and "an effective amount" are used interchangeably herein and refer to that amount of a contrast agent being administered that is sufficient to effect the intended application. The effective amount of the contrast agent can include enough so that the disease, for example, in the host can be imaged, studied, diagnosed, or the like. For example, an effective amount of a contrast agent including a compound will relieve to some extent one or more of the symptoms of the disease being treated, and/or that amount that will prevent, to some extent, one or more of the symptoms of the disease that the host being treated has or is at risk of developing. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

"Cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

It should be noted that precancerous cells, cancer cells, cancer, and tumors may be used interchangeably in the disclosure.

Discussion

MRI is an advanced imaging technique which collects real time, non-invasive, three dimensional imaging with high resolution, high depth penetration. MRI not only can collect anatomic images, but only can collect functional data such as water perfusion, blood vasculature, and tissue oxygen levels. MRI is also the attractive imaging modalities for molecular imaging of disease biomarkers. The combination of these data collected by MRI will provide informative guidance for disease diagnostics.

The molecular imaging of diseases biomarkers, however, are limited by the lack of MRI contrast agents which specifically binds biomarkers and alter the signal intensities with high dose efficiency. The expression level of biomarkers such as cell surface receptors is typically at nM or pM level. Since current clinically available MRI contrast agents have low relaxivity and requires 0.1 mM to observe MRI signal changes, it is hard to detect biomarkers by current clinically available MRI contrast agents incorporated with tumor targeting moieties. For example, $10^5$ GRPR molecules are expressed one PC3 cell, a prostate cancer cell line. Assuming PC3 cell has a volume of 1000 $\mu m^3$ (10 $\mu m \times 10$ $\mu m \times 10$ $\mu m$), then the local GRPR concentration is 1.7 $\mu M$. Current clinically available MRI contrast agents has a detection limit above 30 $\mu M$ and do not have biomarker targeting moieties. Thus, current clinically available MRI contrast agents cannot image this biomarker. Even the current clinically available MRI contrast agent is engineered with GRPR targeting peptide; the local concentration of contrast agents (1.7 $\mu M$ assuming 1 to 1 binding) is lower than detection limit of current clinically available MRI contrast agents. Thus, MRI contrast agents with high relaxivity (low detection limits) and specific biomarker targeting sequence are essential for the success of molecular imaging of biomarker.

The detection limits of MRI contrast agent are correlated with the relaxivity. Current clinically available MRI contrast agents with a relaxivity less than 5 mM$^{-1}$ s$^{-1}$ only have a relaxivity above 10 μM. When the relaxivity increase to above 100 mM$^{-1}$ s$^{-1}$, the detection limit of the contrast agents decreases to less than 690 nM. ProCA3 has a per particle $r_1$ relaxivity about 60 mM$^{-1}$ s$^{-1}$. 2 μM of ProCA32 can enhance the MRI signal. Thus, ProCA32 is a good candidate for developing MRI contrast agents for the molecular imaging of biomarkers with limited expression level. ProCA32M has an elimination half-life around 3 h. Therefore, this contrast agent has a good time window for the marker recognition, molecular imaging and excretion.

We designed three ProCA32 based MRI contrast agents for the molecular imaging of tumor biomarkers, such as GRPR, HER-2 and integrin $\alpha_v\beta_3$. ProCA32.bomb selectively enhances PC3 tumors other than H441 tumor in xenograft mice model. Since PC3 cells have more than 10 times higher GRPR level than that of H441, this result suggests that ProCA32.bomb can semi-quantitatively evaluate GRPR expression levels in different tumor. We also engineer HER-2 targeted ProCA3 (ProCA32.affi). ProCA32.affi can image HER-2 receptor in both xenograft SKOV-3 model and MCF10-DCIS isotropic model. These results suggest that targeted ProCA32 can be applied for the imaging of different biomarkers by engineering different biomarker targeting moieties and targeted ProCA32 has enormous potential to be applied for preclinical drug discovery and current clinically available tumor diagnosis and evaluation.

We developed tumor specific MRI contrast agents for the molecular imaging of tumor biomarkers. These novel targeted ProCA3s variants can binds to biomarkers such as GRPR, HER-2 and integrin $\alpha_v\beta_3$ with high specificity. Molecular imaging of GRPR and HER-2 in mice model shows semi-quantitative enhancement of biomarkers in tumor. Integrin $\alpha_v\beta_3$ targeted ProCA32, ProCA32.RGD also able to target tumor cells with high expression of integrin $\alpha_v\beta_3$. The success of MR imaging of GRPR and HER-2 suggest that targeted ProCA3s can be applied to image other important tumor biomarkers by engineering different biomarker targeting moieties. Thus, targeted ProCA3 has great potential to detect tumor location, tumor size, evaluate tumor progression by semi-quantitative evaluate biomarker expression levels and facilitate personalized medicine for tumor treatment.

MRI is a powerful, non-invasive diagnostic tool for living organisms and provides real-time images with great spatial resolution (Terreno et al., (2010) *Chemical Reviews* 110: 3019-3042). The image contrast is based on the excitation and relaxation of water and lipids in tissues. The intrinsic longitudinal ($T_1$) and transverse ($T_2$) relaxation time of different parts of the tissues generate image contrast based on the MR signal intensity. Because of the small intrinsic variations in $T_1$ and $T_2$ of most tissues, contrast agents are routinely applied to enhance contrast by shortening the relaxation time of the protons in the neighboring water molecules (Strijkers et al., (2007) *Anti-cancer Agents in Medical Chemistry* 7; Waters et al., (2008) *Basic Res. Cardiol.* 103: 114-121; Yoo & Pagel (2008) *Frontiers in Bioscience* 13: 1733-1752; Na et al., (2009) *Advanced Materials* 21: 2133-2148). $T_1$ positive contrast agents mainly shorten the relaxation time $T_1$, generating a brighter image, while $T_2$ contrast agents produce a darker image by shortening the transverse relaxation time, $T_2$.

The effectiveness of a contrast agent is usually evaluated by its relaxivity $r_1$ or $r_2$, given by: $1/T_{isample}=1/T_{isolvent}+r_j$ [M](i=1, 2). In this equation, $1/T_{isample}$ and $1/T_{isolvent}$ are the relaxation rates of the sample and pure solvent in s$^{-1}$, respectively, and [M] is the concentration of the contrast agent in mM. The ratio between $r_2$ and $r_1$ ($r_2/r_1$) is generally used to determine whether a contrast agent is suitable for $T_1$ or $T_2$ contrast (Strijkers et al., (2007) *Anti-cancer Agents in Medical Chemistry* 7). Normally, $T_1$ contrast agents have a lower ($r_2/r_1$) ratio (e.g., 1-2) while $T_2$ contrast agents have a larger ($r_2/r_1$) ratio (>10) (Tromsdorf et al., (2009) *Nano Letts.* 9: 4434-4440). $T_1$ positive contrast agents are clinically preferred because the brighter contrast brings higher resolution and is more easily detected in the MR images (Okuhata et al., (1999) *Advanced Drug Delivery Reviews* 37: 121-137).

$T_1$ contrast agents are generally paramagnetic Gd$^{3+}$ or Mn$^{2+}$ complexes (Caravan et al., (1999) *Chemical Reviews* 99: 2293-2352; Federle et al., (2000) *J. Magnetic Resonance Imaging* 12: 689-701). Their small sizes allow them to freely diffuse into extravascular space with low specificity (Caravan, P (2006) *Chem. Soc. Revs* 35: 512-523). Conjugation to macromolecules, such as dendrimers, (Cheng et al., (20090 *Adv. Functional Materials* 19: 3753-3759; Swanson et al., (2008) *Int. J. Nanomed.* 3: 201-210), liposomes (Ghaghada et al., (2008) *Academic Radiol.* 15: 1259-1263; Fossheim et al., (1999) *Magnetic Resonance Imaging* 17: 83-89; Zhang et al., (2009) *Europ. J. Radiol.* 70: 180-189), or proteins (Caravan, P. (2009) *Accounts of Chemical Res.* 42: 851-862; Yang et al., (2008) *J. Am. Chem. Soc.* 2008, 130: 9260-9267) has been explored to enhance the relaxivity and minimize the diffusion. In accordance with the purpose(s) of the present disclosure, as embodied and broadly described herein, aspects of the present disclosure, in one aspect, relate to contrast agents, compositions including contrast agents, methods of making contrast agents, methods of imaging, methods of diagnosing, methods of studying, and the like. More particularly, the contrast agents of the disclosure include magnetic resonance imaging contrast agents that accumulate in tissue and can be used to determine the presence and/or location of a target. In addition, contrast agents of the present disclosure can include target-specific moieties to target cells or tissue (e.g., cancer).

Detecting tumor metastasis by MRI is still presenting obstacles. Only a few examples in the literature (*BMC Cancer* 2011, 11, 40) report the detection of tumor metastasis using liver-specific MRI contrast agents such as Primovist®. However, it is extremely hard to detect small tumor metastasis with a diameter of about 1 mm or less. However, the injection of a protein contrast agent such as ProCA3 of the disclosure can enhance the specific organ more than do other MRI contrast agents. Accordingly, ProCA3 can be used for imaging metastasis to these organs with high sensitivity.

Compared to the literature-reported imaging tumor metastasis (larger than 0.5 cm in diameter), the ProCAs of the disclosure can detect a metastatic tumor with much smaller size (about 0.25-1 mm).

Dynamic contrast enhanced-MRI (DCE-MRI) is a powerful technique to monitor tumor vasculature changes. Current clinically available MRI contrast agents are already used for DCE-MRI tests. Compared to these contrast agents, the ProCAs of the disclosure have several advantages: 1) The DCE-MRI requires high accuracy to monitor contrast agents concentration in blood over time (so called artery input function (AIF)). However, the short retention and fast elimination rate in blood of current clinically available MRI contrast agents lack sufficient accuracy to measure AIF. Blood circulation time for the ProCAs of the disclosure is much long than current clinically available MRI contrast agents, allowing accurate measurements of AIF, improving the reliability of DCE-MRI; 2) Due to their small size, current clinically available MRI contrast agents cannot differentiate the small pores and large pores in tumor vessel leakage. ProCAs have a larger size compared to these current clinically available MRI contrast agents, which is good for distinguishing tumor vessels with small pores and large pores; 3) ProCAs have high relaxivity and dose efficiency, allowing lower dosages than that of current clinically available MRI contrast agents.

In general, the present disclosure provides contrast agents that include a scaffold polypeptide that includes (e.g., integrated into the scaffold polypeptide) at least one metal ion binding site (e.g., 1, 2, 3, 4, 5, or more biding sites) (also referred to as "metal ion binding site") capable of chelating paramagnetic and heavy metal ions. The contrast agents of the disclosure can further include a target-specific moiety such as, but not limited to, a cell receptor ligand, a ligand selectively binding to a cell surface marker, and the like. The contrast agents of the disclosure can include a near-IR moiety (e.g., functional group). The modification of the metal binding site, either by residue mutation or insertion is intended to alter the metal selectivity of the binding site. The contrast agents can include a metal ion interacting (e.g., bonding with or chelating with) with the metal ion binding site. A contrast agent can include two metal ions interacting (e.g., bonding with or chelating with) with two metal ion binding sites. The metal ion binding site may be developed by a design approach or by a grafting approach. After the site has been developed, the site or sites are operatively integrated into the select areas of the scaffold polypeptide.

The contrast agents of the disclosure are stable in a physiological environment. The phrase "physiological environment" can be described as cell, cellular conditions, tissues, organs, and vertebrate/invertebrates, animal/human or buffer conditions (e.g., pH of between about 6 and about 8 and a temperature of about 5-45° C.) mimic closely to cellular, or in vivo conditions. The term "stable" in reference to "physiological environment" means that the contrast agent is able to provide contrast capability and remain intact at least during the desired period of use. The phrase "stable in a physiological environment" refers to the contrast agent including at least one metal ion and the binding of the metal ion causes no changes or substantially no changes to the scaffold polypeptide conformation or to the binding affinity of the tailored metal ion binding site under physiological conditions that would cause premature release of the metal ion, and that the contrast agent functions as described herein.

The scaffold polypeptide of the contrast agent includes polyethylene glycol compounds (PEG) attached to the polypeptide. The PEGs can be attached (e.g., bonded) to the polypeptide via an amino acid residue such as lysine (Lys), glutamic acid (Glu), aspartic acid (Asp), cysteine (Cys), and/or carboxyl/amino terminals. The position of the amino acids of the polypeptide can be selected to position the PEGs so that the PEGs do not substantially interfere (e.g., decrease metal binding affinity more than 20%) with or interfere with the metal ion binding sites ability to interact with the metal ion of interest or the conformation of the polypeptide. The PEGs can be attached to one or more Lys residues since the position of the Lys residues on the polypeptide is such that the PEGs do not substantially interfere with or interfere with the metal ion binding site ability to interact with the metal ion of interest or the conformation of the polypeptide.

Unless otherwise indicated, reference to "contrast agent" can also refer to a contrast agent that includes PEGs. Additional details regarding PEGs are described herein.

The present disclosure provides for PEGylated contrast agents, where the PEGylation increases the blood circulation time of the contrast agent in recipient subjects. In addition, PEGylation of the contrast agent increases the solubility of the contrast agent by more than two-fold, three-fold, four-fold, five-fold, six-fold, seven-fold, eight-fold, nine-fold, ten-fold, or more relative to the un-PEGylated contrast agent. It should also be noted that PEGylation of the contrast agent further increased the in vitro of one or both R1 and r2 relaxivities of the contrast agents by about 10%, 25%, 50%, 75%, 100%, or 2-3 fold or more, relative to the non-PEGylated contrast agent. Although not intending to be bound by theory, the increase in molecular size due to the PEGylation and the addition of a hydration layer due to water retention by poly-PEG chain on protein surface may be the reasons for the increases in the relaxivities. PEGylation further confers the advantage of reduced immunogenicity of the protein contrast agents of the disclosure.

The disclosure further provides contrast agents capable of enhancing image contrast by affecting water molecule proton relaxation rates. Such contrast agents are effective for magnetic resonance imaging, in part because the water proton relaxation rate in the target tissue is affected differently from the relaxation rate of the water protons in the surrounding tissue. In the present disclosure, the contrast agents are paramagnetic species, which form complexes with metal ions, so to alter the relaxation rates of adjacent nuclei.

The scaffold polypeptide for MRI applications is a polypeptide that will host the tailored metal ion binding sites and has the following characteristics: (a) stability in a physiological environment; (b) a topology suitable for the integration of metal ion sites; (c) a rotational correlation time optimized for the magnetic field (e.g., around 100 millisecs in a magnetic field of 1.3 to 3 T), e.g., higher magnetic field application can demand a host polypeptide with a larger molecular weight; and (d) a water exchange rate such that the relaxivity of the polypeptide is not limited by the water exchange rate.

With the development of high-field MRI scanners, there is a strong need to develop contrast agents with high relaxivity in high magnetic field strength. However, the relaxivity of current macromolecular contrast agents dramatically drops at high magnetic field. The relaxivity for ProCA32 is 18 $mM^{-1} s^{-1}$, which is g than 3 times greater than that of DTPA, and reaches the theoretical up limits of the per Gd $r_1$ of $Gd^{3+}$ at 7 T (about 20 $mM^{-1}s^{-1}$). Other ProCA3 agents of the disclosure also have a per Gd $r_1$ relaxivity around 20 $mM^{-1}s^{-1}$ at 7 T and room temperature. These results indicate that ProCA3 has high relaxivity even in the high magnetic field and provides for the development of MRI contrast agents that are advantageous for use in the high magnetic field environment.

A property of the scaffold polypeptide is its ability to accept the introduction of metal ion binding sites therein. The scaffold polypeptides of the disclosure have a three-dimensional structure or an amino sequence with some homology to polypeptides whose structures have been solved, at least in part. Specifically, the scaffold polypeptide is screened to determine whether it can tolerate the integration of various binding sites without excessive denaturation. For example, the integration of metal ion binding sites into the scaffold polypeptide should not denature or unfold the protein. Thus, the metal ion binding site should not be placed by mutating a hydrophobic core or in a position that results in substantial structural perturbation. This can be examined by sequence alignment of proteins in the same family. The amino acids that have an essential role in folding of the structure or the function will be conserved among different species of this same type of the protein.

Metal ion binding sites are placed into a scaffold polypeptide such that the metal can be tumbled together with the protein. It is better to find a location that is not so flexible or the same flexibility as the polypeptide body so as to match the correction time. It is preferred to design or create the binding pocket in the polypeptide. Although insertion could work, it is preferable to do so in a relatively not so flexible region. Usually the protein can be checked by looking at the B factor (temperature factor for X-ray) or S2 factor (dynamic flexibility factor for NMR) of the pdb (protein data bank) file of the structure.

More than one metal binding site may be integrated into a scaffold polypeptide. The inclusion of more than one binding site improves the sensitivity of the contrast agent. Where more than one binding site is integrated into the protein, the site could have different affinities, but should still have strong enough affinity for the selected metal so to avoid competition with physiological metal ions. Both metal ions should be embedded into the host polypeptide with preferred rotational correlation times and water exchange rates to provide MRI contrast with an increased sensitivity.

The contrast agent can have a high affinity to and can preferentially select a particular metal ion (e.g., $Gd^{3+}$, $Mn^{2+}$, or $Fe^{3+}$). Contrast agents of the disclosure can show a dissociation constant $K_d$ less than $10^{-12}$ [M] for $Gd^{3+}$ in an environment having physiological metal ions and prevented those metal ions from precipitation under physiological conditions. Thus, the present disclosure may be used to create contrast agents having optimal selectivity for a specific metal ion.

The disclosure can provide a new mechanism to increase the relaxivity of contrast agents. This is accomplished by designing the metal ion binding sites, e.g., $Gd^{3+}$, in proteins, which can eliminate the mobility and flexibility of the chelating moiety associated with currently available contrast agents. High proton relaxivity by contrast agents can further enhance images.

An advantage of the present disclosure is that it provides contrast agents that can preferentially chelate a specific metal ion. For example, a preferred contrast agent having $Gd^{3+}$ binding site(s) will preferentially chelate $Gd^{3+}$ over other metal ions, such as $Mg^{2+}$ or $Ca^{2+}$. The ability to preferentially chelate a specific metal ion can improve the specificity of a contrast agent and reduces the cytotoxicity of the contrast agent.

A fusion protein/peptide/polypeptide or a non-degradable particle moiety can be added to the protein contrast agent with a linker to tune the correlation time for optimal contrast sensitivity, targeting (e.g., subcellular, cellular, tissue and organ selectivity), biodistribution (e.g., but not limited to, an affibody against to Her-2 was fused to CA1 as a targeted contrast agent to breast cancer), and/or bioelimination (e.g., using proteins with molecular weight less than 60 KDa). One of ordinary skill in the art may determine such linkers without undue experimentation.

An additional advantage of the contrast agent of the present disclosure is that targets of interest (e.g., specific tissues, specific organs, and biomarkers for molecular imaging of tissues and tissue growths such as cancerous cells or tissue, precancerous cells or tissue, cancer, or tumors) can be imaged. The active targeting of contrast agents to specific organs or tissues can be achieved by attaching (directly or indirectly via linking) a compound (e.g., peptide, antibody, antigen, and the like) having an affinity for the target of interest. Thus, the contrast agent can be administered to the host, and the contrast agent will interact with the target of interest. Subsequently, the host can be imaged to determine the presence or absence, as well as the location of the target of interest.

Scaffold Polypeptide

Scaffold polypeptides suitable with the present disclosure are inclusive of both natural amino acids and unnatural amino acids (e.g., β-alanine, phenylglycine, and homoarginine, rcarboxyglutamate (Gla)). The amino acids are alpha-amino acids, which can be either of the L-optical isomer or the D-optical isomer. The amino acids are D-optical isomers, as such isomers are less subject to proteolytic degradation. Such amino acids can be commonly encountered amino acids that are not gene-encoded, although preferred amino acids are those that are encodable. A near-IR functional group (e.g., Cy5.5, Cy7, Alexflour, and indocyanine green) for near-IR detection can be covalently bound to the scaffold polypeptide, a PEG, and/or a target-specific moiety. The scaffold polypeptides preferably further include one or more amino acid residues (e.g., Lys, Glu, Asp, Cys, or combinations thereof) able to bond with the PEGs or otherwise modified.

Various scaffold polypeptides may be used according to the disclosure. More specifically, suitable scaffold polypeptides can be selected properties suitable for diagnostic applications. The scaffold polypeptide for use with this disclosure may be of unitary construction (a particulate, a polychelant or a dendrimeric polypeptide). Scaffold proteins suitable with this disclosure may be selected without undue experimentation. For example, but not intended to be limiting, scaffold polypeptides suitable for use in the protein contrast agents of the disclosure include CD2, and parvalbumin.

The present disclosure encompasses proteins such as CD2 proteins (a cell adhesion protein) that exhibit high stability against proteolysis, thermal conditions (Tm 67° C.), pH (2-10), and salt (0-4 M NaCl) denaturation. CD2 proteins can be suitable with this disclosure because such proteins are stable in physiological environments, have a topology suitable for the integration of at least one or multiple metal ion chelating sites, and typically have a relaxivity greater than 10 $mM^{-1}s^{-1}$ (some of them up to about 50 $mM^{-1}s^{-1}$). In addition, CD2 proteins can tolerate multiple surface mutations without unfolding the protein. The CD2 proteins can be used as a host protein to design such as $Gd^{3+}$ binding sites.

Fluorescent polypeptides are another class of preferred scaffold polypeptide for this disclosure, as these polypeptides are stable in a physiological environment against proteolytic degradation and pH denaturation (pH 5-10). One advantage of using fluorescent proteins is that contrast agents constructed from such proteins can be multi-functional probes. Contrast agents constructed from fluorescent proteins can be screened using both fluorescence and MR imaging. This can be advantageous as such properties equip the contrast agent with both the fluorescence needed for fluorescence detection methods and sensitivity needed for the deep tissue detection from MRI. Such contrast agents are multifunctional contrast agents.

Natural metal binding proteins such as calmodulin, calbindin D9K, troponin C, and parvalbumin, can be engineered to bind paramagnetic metal ions with very strong metal binding affinity thus are capable of enhancing image contrast by affecting water molecule proton relaxation rates.

In addition, their selectivity over calcium and other physiologic metal ions such as zinc and magnesium is more than $10^5$ foldhigher, which is similar to that of current clinically approved contrast agents such as DTPA or DTPA-BMA. More than one water molecule can be in the coordination shells and protein surface, and this likely contributes to their extremely high relaxivity. Furthermore, functional sites of these engineered proteins, such as binding to the target molecules by calmodulin, were altered and PEGylation of these engineered proteins increases solubility and reduced immunogenicity and increase relaxivity Scaffold protein sequences that can be included in the contrast agent are provided that include the unmodified scaffold polypeptides and modified scaffold polypeptides (insertions and/or deletions) for a variety of illustrative scaffold polypeptides that include metal ion binding sites. The scaffold polypeptide sequences include one or more possible locations for attachment of PEGs, mutation sites, C-terminal sites for PEGylation or conjugation of moieties (e.g., fluorescent dyes), and the like.

PEGylated ProCAs

Contrast agents where PEGs are attached to the polypeptide via one or more amino acid residues such as Lys, Glu, Asp, Cys, carboxyl/amino terminals, or combinations thereof, are herein provided. The PEGs are attached to amino acid residues so that the PEGs do not substantially interfere with or interfere with the metal ion binding site ability to interact with the metal ion of interest or the conformation of the polypeptide. The PEGs can be attached to the amino acid residues through PEGylation processes known in the art. The PEGylation may, for example, be performed at a pH of about 7.5 to 9 or about 8 to 8.5.

The PEGs can be linear PEGs, multi-arm PEGs, branched PEGs, and combinations thereof. The molecular weight of the PEGs can be about 1 kDa to 100 kDa, about 1 kDa to 50 kDa, about 1 kDa to 40 kDa, about 1 kDa to 30 kDa, about 1 kDa to 20 kDa, about 1 kDa to 12 kDa, about 1 kDa to 10 kDa, or about 1 kDa to 8 kDa. It should be noted that the molecular weight can be any integer within any of the values mentioned above. When used in reference to PEG moieties, the word "about" indicates an approximate average molecular weight and reflects the fact that there will normally be a certain molecular weight distribution in a given polymer preparation. From 1 to 10 PEGs or more can be attached to the scaffold polypeptide.

The PEGs can have additional functional groups to allow us to further modify the contrast agent by adding other moieties such as signal peptides (such as GRP signal peptide for targeting to prostate cancer).

Target-Specific Moiety

The contrast agents of the disclosure can have a specific affinity for a target by attaching a target-specific moiety to the contrast agent. In this regard, the term "affinity" means that the contrast agent is preferentially attracted to the target(s) as opposed to all other targets in the human subject. The contrast agent can be designed to have the affinity using one or more polypeptides or chemical moieties on a target. If the target-specific moiety is attached to the scaffold polypeptide (attached directly or indirectly), like the PEG (attached directly or indirectly), the target-specific moiety does not substantially interfere with or interfere with the metal ion binding site ability to interact with the metal ion of interest or the conformation of the polypeptide.

A target-specific moiety can be attached (e.g., directly or indirectly) to the scaffold polypeptide, where the target-specific moiety has an affinity for a target (e.g., a cell, a tissue, a protein, an antibody, an antigen, and the like). The target-specific moiety can include, but is not limited to, polypeptides (e.g., but not limited to, antibodies (monoclonal or polyclonal)), antigens, nucleic acids (both monomeric and oligomeric), polysaccharides, sugars, fatty acids, steroids, purines, pyrimidines, ligands, or combinations thereof, where the target-specific moiety binds or otherwise interacts with the target. The target-specific moiety specifically interacts with a specific type of target or specific target and substantially (e.g., 90%, 95%, 99% or more specificity to the target or type of target) or completely excludes other targets. The target-specific moiety can have an affinity for one or more targets. The target-specific moiety can be selected based on the target selected and the environment the target is in and/or conditions that the target is subject to. The target-specific moiety can include: a biomarker probe, a precancerous target-specific moiety, a cancer target-specific moiety, a tumor target-specific moiety, and a probe or agent that targets at least two of a biomarker, a precancerous cell, a cancer cell, and a tumor.

The target-specific moiety can be linked, directly or indirectly, using a stable physical, biological, biochemical, and/or chemical association. The target-specific moiety can be independently linked to the scaffold polypeptide or the PEG using, but not limited to, a covalent link, a non-covalent link, an ionic link, a chelated link, as well as being linked through interactions such as, but not limited to, hydrophobic interactions, hydrophilic interactions, charge-charge interactions, $\pi$-stacking interactions, combinations thereof, and like interactions. One advantageous linker for attaching a target-specific moiety to a scaffold polypeptide of the disclosure is the peptide Gly-Gly-Ser-Gly-Gly.

The target-specific moiety can include, but is not limited to, gastrin release peptide (GRP) that can bind to specific types of cancer receptors, i.e. GRP receptors, and RGD peptides (Arg-Gly-Asp) corresponding to integrin $\alpha v \beta 3$ targets. Molecules that can be targets include, but are not limited to, vascular receptors (e.g., vascular endothelial growth factor receptor (VEGFR)), extracellular matrix proteins (e.g., proteases, MMP, thrombin), cell membrane receptors (e.g., epidermal growth factor receptor (EGFR) (e.g., HER-2)), intracellular proteins, enzymes (e.g., caspases and PSA), serum proteins (e.g., albumin), and the like.

Metal Ion Binding Sites

The affinity of the metal ion binding site may vary the contrast agent affinity for metal ions. Specifically, as affinity and sensitivity of the metal ion binding sites may be modified, the relaxivity and metal affinity of the contrast agent may be modified. Preferably, the metal ion binding site has optimal imaging properties including metal binding affinity, selectivity, relaxivity, NMRD profile, and water exchange rates.

The metal ion binding site of the present disclosure may be constructed using three methods: (1) a computational design approach in which the metal ion binding site with a selectivity and affinity for a metal ion is engineered and rationally designed de novo based on optimal binding characteristics of a metal ion with other moieties; (2) a grafting method in which the metal ion binding site with a selectivity and affinity for a metal ion is engineered and constructed selectively by varying the primary, secondary, and tertiary of an identified binding site; (3) direct modification of natural metal binding proteins in which the metal binding affinity to the desired metal ions are significantly increased while the affinity to the physiological metal ions are decreased. An engineered metal binding site can be created by a combination of more than one above mentioned methods.

Computational Design Approach

The computational design approach focuses on designing a metal ion binding site de novo. This design approach focuses on using an algorithm to construct and engineer an optimal binding site. Preferably, the computation design approach is used to create optimal binding sites by, e.g., varying the coordination geometry of the site, the water number in the coordination shells, the ligand types, and the charges.

The computational design approach comprises the following steps: (1) accessing one or more databases having structural, coordination, and/or 3-dimensional structure or model on metal ion binding sites; or creating model structures based on the sequence homology; (2) generating one or more preliminary metal ion binding sites from portions of the structural data; (3) selecting rationally one or more suitable metal ion binding sites from the generated preliminary binding sites based on, e.g., coordination geometry; and (4) creating a metal ion binding site by tailoring and tuning the selected metal ion binding site.

The metal ion binding site may be incorporated into a scaffold polypeptide, e.g., a fluorescent or CD2 protein. Further, such a method may be used to alter metal ion binding properties of proteins and generate new materials with various ion binding affinities.

More particularly, the method involves searching and accessing databases for preferred components of a metal ion binding site. Such databases that may be searched for the criteria or components may include public domain banks (e.g., NBCI or PubMed) or knowledge banks such as protein modeling structure data banks (e.g., Cambridge or RCSB Protein Data Bank Data Bank and BioMagResBank database) or data bank. Further, the database could include structural data from metal ion binding proteins whose structures have been characterized previously. One of ordinary skill in the art can identify databases and sources of material for databases suitable with this disclosure. Use of a computer obviously would greatly speed up the searching and is preferred.

These databases may be used to provide structural analysis of metal ions bound to a protein. Such analysis may include local coordination properties, types of residues or atoms commonly used to bind a desired metal ion, chemical features (e.g., pKa or changes), the number of charged residues on a site, and the range or deviation of the known binding sites. Further, such analysis may include the environment, such as types of atoms, residues, hydrophobicity, solvent accessibility, shapes of the metal binding sites, electrostatic potentials, and the dynamic properties (e.g., B-factors or the order factors of the proteins) of the binding sites. Such analysis also may include whether a binding site for a particular metal ion is a continuous or discontinuous binding site.

Once preliminary metal ion binding sites are found, using the structural data and analysis, one or more suitable metal ion binding sites may be generated based on rational factors. Specifically, different search algorithms may be used to generate potential metal ion binding sites based on other key features in addition to, for example, the geometric descriptors. These key features include the properties of the original residues in the scaffold polypeptide, ligand positions that are essential to protein folding, the number of the charged residues and their arrangement and number of water molecules in the coordination shell. The hydrogen bond network and the electrostatic interactions with the designed ligand residues also can be evaluated. Furthermore, the protein environments of metal ion binding sites can be analyzed according to solvent accessibility, charge distribution, backbone flexibility, and properties of scaffold polypeptides. Thus, one of ordinary skill in the art may rationally select a binding site based on desired parameters.

Once the metal ion binding sites are generated, a site may be tailored using two complementary approaches of computational design and grafting. First, the metal ion binding site may be tailored using a grafting method in which the primary, secondary, tertiary, and/or quaternary structures are tuned. Second, the metal ion binding site may be tailored using a computational design approach. It is understood that one or both of these approaches may be used to tailor the binding site.

The computational design approach includes modifying the metal ion binding site by modifying residues in the scaffold of the metal ion binding site. A geometric description of the ligands around a metal ion, a three-dimensional structure of the backbone of proteins, and a library of side-chain rotamers of amino acids (or atoms from the main chain) can identify a set of potential metal-binding sites using a computer. Using the geometric and graph description of a particular metal ion site, key ligand residues are carefully placed in the amino acid sequence to form the metal (metal ion) binding pocket. This binding pocket can be created automatically by the computer algorithm according to the coordination description and the user's preferred affinity.

The created potential metal ion binding sites can be optimized and tuned to specification. A backbone structure of the metal ion binding site with different degrees of flexibility may be used according to the need or the flexibility of the metal ion binding site. The designed metal ion binding sites are further filtered and scored based on the local factors, which may include the shape of the metal ion binding sites, locations, charge numbers, dynamic properties, the number of mutation needed, solvent accessibility, and side chain clashes. To achieve the maximums relaxivity, one to two oxygen atoms from the solvent water molecules in the coordination shell may provide additional coordination without reducing the required binding affinity and selectivity.

Stronger metal ion binding affinities of the designed sites may be developed based on several modeled factors that contribute to metal ion affinity. For example, the number of ligand residues is a factor to directly chelate a specific metal ion. In some cases, to have a strong metal ion affinity with a $K_d$ necessary to measure a metal ion concentration, it is necessary to include residues from the protein frame for optimal metal ion binding. In other cases, the number of charged residues is able to change metal ion affinity. In still other cases, the ligand type is a factor as the binding preferences of a chelate may depend on the particular ligand type. Other factors such as negatively charged environments may contribute to the binding affinity of a metal ion binding protein and can be taken into account by those of ordinary skill in the art without undue experimentation. These charged residues could increase the water-exchange rate to avoid its limitation for the required relaxivity.

The Grafting Method

The grafting method focuses on engineering and constructing a metal ion binding site by modifying the primary, secondary, tertiary, and/or quaternary structure of an identified binding site. By selectively manipulating the structure of the binding site, it is possible to obtain a metal ion binding site that can be engineered into a scaffold polypeptide, e.g., CD2 or fluorescent protein, without significantly denaturing the protein. Using the grafting method, it is possible to achieve a binding site that has a stronger preference for one metal ion over another metal ion. Such modifications may allow for improved contrast abilities.

Initially, an identified binding site for use with the grafting method may be any continuous sequence site that has some affinity for a metal ion. Such binding sites may derive from either known binding peptides such as an individual EF-hand site or from short fragments that have demonstrated the ability to bind specific metal ions such as alpha-lactalbumin. Such peptides may be highly conserved in nature and prevalent throughout nature or may be unnatural but known to have an affinity for a particular metal ion. One of ordinary skill in the art is able to identify binding sites with affinity for a metal ion without undue experimentation.

Once the binding site has been identified, the primary structure of the metal ion binding site may be altered and tuned to achieve a metal ion binding site with improved binding characteristics. For example, more charged ligand residues such aspartate and glutamate may be engineered by inserting codon(s) into the metal ion binding site so as to tune the responsiveness of the site or the scaffold polypeptide. The inclusion of additional charged ligands can allow the contrast agent to achieve an affinity for selected paramagnetic metal ions and to have a desired selectivity. Further, one or two water molecules can also be introduced into the coordination shell by removing or modifying ligand residues and their environments. Further other mutations to the primary structure include removing or adding amino acids to change properties such as flexibility or rigidity of the site. Adding or removing amino acids from the binding site alters the primary structure of the binding site.

The secondary structure of the metal ion binding site, that is the spatial arrangement of amino acid residues that are near one another in linear sequence, may be modified to tune the sensitivity and responsiveness of the metal ion binding site. The residues on the site itself, the flanking or the neighboring structures such as helices, beta strands, or turns may be modified by changing properties such as hydrophobicity, salt bridges, secondary structure propensity (e.g., helicity and β-sheets), and charge interactions with different amino acids, which all may inherently change the secondary structure.

The tertiary structure of the metal ion binding site may be modified to further tune the sensitivity and responsiveness of the metal ion binding site. The affinity of the metal ion binding site for the metal ion may be varied by selectively manipulating and adding helices, loops, bridges and/or linkers and chemical properties such as hydrogen bonding, electrostatic interactions and hydrophobic interactions. In fact, such variations in tertiary structure may add stability and affinity by increasing secondary structure propensity, adding charge interaction of the side chains, and by stabilizing the metal ion binding coordination chemistry. As such, it may be possible to increase or decrease the binding affinity of the continuous binding site by tuning the tertiary structure of the metal ion binding site. In addition, the dynamic properties can be modified by increasing the packing of the protein and replacing residues with amino acids or other moieties with more rigid (e.g., Pro) or flexible (e.g., Gly) properties, One method of directly altering the primary, secondary, and/or tertiary structure of the metal ion binding site is by altering the charges in the site. As the charges in any binding site have a significant role in the structure of the site, changing the charges or charge ratio may have significant impact on the structure of the site. In addition, as the charged side chains exhibit a strong influence on the metal ion binding affinity even though they are not directly involved as ligands, the variation of these chains results in variations in metal ion binding affinities and selectivity. A metal ion binding site may have stronger affinities to and better selectivity for a desired metal ion over a competitive metal ion by designing or modifying the site, e.g., changing the number of charged ligand residues to form metal ion binding pockets. For example, the metal ion binding affinity of the metal ion binding site may be varied by changing the charged side chains that are present on the metal ion binding site and/or the neighboring environment. The replacement of charged residues such as aspartate or glutamate with a residue such as alanine may dramatically reduce the binding affinity for the metal ion by up to 100 times.

In the case of multifunctional contrast agents, e.g., where the contrast agent is a fluorescent protein, it can be a factor to induce the metal binding site without altering significantly the chromophore environment to reduce the fluorescent signal. These metal binding sites can be added at remote locations away from the chromophore or simply fusion to the fluorescent moieties. Such locations can be evident from the sequence and protein folding.

The grafting approach may be used with the design approach to create an optimal metal binding site. For example, metal binding sites can be created by using part of continuous site and part of ligand residues created by computer design. The loops or any sequences of the proteins can be removed or modified to achieve optimal required binding affinity, metal selectivity, relaxivity and stability.

Thus, by varying the primary, secondary, and/or tertiary structure of the metal ion binding site, it is possible to achieve a metal ion binding site with desired specificity and affinity and more importantly contrast abilities.

The Modification Method of Native Metal Binding Proteins

The metal binding affinities of natural metal binding proteins can be altered by directly modifying the proteins such as the addition of metal ligand residues in the metal binding proteins to increase metal binding affinity to lanthanides. Fragments and/or domains of the natural metal binding proteins encompassing metal binding sites can also serve as scaffold polypeptide of the contrast agents if they exhibit strong metal binding affinity for $Ln^{3+}$ or other paramagnetic metal ions, serum stability, and desired relaxation properties. The affinity to natural metal ions such as physiological metal ions, e.g., calcium, zinc, and magnesium, will be significantly reduced by deleting metal binding ligand residues or reducing the cooperativity between coupled metal binding sites. Calcium binding sites in a natural calcium-binding protein such as parvalbumin can be modified so that the modified proteins have a strong metal binding affinity to lanthanides. On the other hand, the metal selectivity for lanthanides over calcium, magnesium and zinc remains very high. If it is necessary, the molecular recognition sites of these natural calcium-binding proteins can be altered by deletion at the active sites or PEGylation.

Selecting Metal ion Binding Sites in the Scaffold Protein

The metal ion binding sites may be selectively introduced into numerous sites of a scaffold polypeptide without substantially impairing its secondary structure. A number of methods for identifying integration sites in proteins, such as CD2 proteins, parvalbumin, calmodulin, and fluorescent proteins are known in the art, including, for example, site directed mutagenesis, insertional mutagenesis, and deletional mutagenesis. Other methods are known or easily ascertained by one skilled in art.

The sites of the fluorescent protein that can tolerate the insertion of a metal ion binding site also may be determined and identified by gene manipulation and screening. By generating mutant proteins and by manipulating the DNA sequence, it is possible to obtain a variety of different insertions, which then may be screened to determine whether the protein maintains its intrinsic activities. Preferably, sites that remove or interfere with the intrinsic fluorescence of the fluorescent protein are not optimal and may be screened out. Variants identified in this fashion reveal sites that can tolerate insertions while retaining fluorescence.

The metal ion binding sites for use with scaffold polypeptides may be selected by considering five criteria so to as optimize the local properties of the metal binding site, the fluorescent protein, and the protein environment. First, the geometry of the metal ion binding site should have relatively minor deviations from the desired coordination geometry. Second, negatively charged residues should be varied by no more than 2-9 charges according to the desired affinity for metal ion ($K_d$). Third, the water coordination shell of the metal ion chelating sites should be able to coordinate at least 1-2 water molecules. Fourth, the residues from the loops between the secondary structures with good solvent accessibility are desired for both the folding of the protein and the fast kinetics required for the contrast agent.

The mutation or the introduction of the metal ion binding site should not substantially interfere with the synthesis and folding of the protein. More particularly, the introduction of the metal ion binding site does not interfere with either post-translational chromophore formation or intermolecular interactions required for stabilizing the chromophores and folding of the protein frame. Furthermore, the introduced side chain should not be overpacked and should not clash with the protein frame of the scaffold polypeptide (e.g., the fluorescent protein). The direct use of chromophore residues as chelating sites is not preferred but is within the scope of this disclosure. The metal binding sites in the natural metal binding proteins can be directly modified to have proper metal binding affinity to the desired metal ions.

Metal Ions

One or more metal ions are atoms and ions, including the respective isotopes and radioisotopes that can bind to proteins or peptides. A metal ion may bind reversibly or irreversibly and such a bond may be covalent or non-covalent. While $Gd^{3+}$ is preferred in the protein contrast agents of the disclosure, it is understood that metal ions suitable with this disclosure include, but are not limited to metal ions including Group IIA metal ions, transition metal ions, and Lanthanide Series ions. Exemplary metal ions include, but are not limited to, the ion, isotope, and/or radioisotope forms of magnesium, calcium, scandium, titanium, manganese, iron, boron, chromium, cobalt, nickel, copper, zinc, gallium, strontium, yttrium, strontium, technetium, ruthenium, indium, hafnium, tungsten, rhenium, osmium, and bismuth. Exemplary radioisotopes include, but are not limited to, $^{64}Cu$, $^{67}Cu$, $^{67}Ga$, $^{68}Ga$, $^{88}Y$, $^{89}Sr$, $^{90}Y$, $^{97}Ru$, $^{99m}Tc$, $^{103}Ru$, $^{111}In$, $^{153}Sm$, $^{186}Re$, $^{188}Re$, $^{203}Pb$, $^{211}Bi$, $^{212}Bi$, $^{213}Bi$, and $^{214}Bi$.

The metal ions chosen to be chelated by the contrast agents depend in part on the diagnostic role of the metal ion. Metals that can be incorporated, e.g., through chelation, include lanthanides and other metal ions, including isotopes and radioisotopes thereof. For MR imaging applications, the preferred metal ion is gadolinium (III).

For MRI or MRS applications, the metal ions should be paramagnetic, and preferably non-radioactive. For X-ray and ultrasound imaging, heavy metal ions, e.g., with atomic numbers of at least 37, or at least 50, should be used, again preferably non-radioactive species. For scintigraphy the metal ions should be ions of radioactive isotopes. For MR, X-ray, EIT or magnetometric imaging, one may use chelating groups to bind to heavy metal clusters (e.g., polyoxoanions and full or partial sulfur analogues).

Methods of complexing metal ions with chelants and polychelants are known to those with ordinary skill in the art. Metal may be incorporated into the contrast agent, i.e., the tailored binding sites, by direct incorporation, template synthesis, and transmetallation. Preferably, the metal ion is chelated into the contrast agents of the disclosure by direct incorporation, which involves titration with solution of sub-stoichiometric levels up to full incorporation.

One or two or more metal ions can bind to the contrast agent. The contrast agent includes one or two or more metal ion binding sites. Each of the metal ion binding sites binds to the same metal ion. Each of the metal ion binding sites binds to a different metal.

Methods of Use

The contrast agents of the disclosure can be used in any one of a number of methods including, but not limited to: methods of detecting, studying, monitoring, evaluating, and/or screening, diseases, conditions, and other biological events in vivo or in vitro. The conditions can include, but are not limited to, altered growth rate of tissues, cancerous transformation of tissues, inflammation or infection of a tissue, altered volume of a tissue, altered density of a tissue, altered blood flow in a tissue, altered physiological function, altered metabolism of a tissue, loss of tissue viability, presence of edema or fibrosis in a tissue, altered perfusion in tissue, and combinations thereof. In particular, aspects encompassed by the disclosure include: methods of imaging tissue; methods of diagnosing the presence of a disease, precancerous cells or tissue, cancer cells or tissue cancer, and tumors, as well as related biological events; methods of monitoring the progress of a disease, precancerous cells or tissue, cancer cells or tissue cancer, and tumors, as well as related biological events; and the like.

Embodiments of the present disclosure include, but are not limited to, methods of imaging, detecting, studying, monitoring, evaluating, and/or screening biological materials (e.g., organs, tissues, tumors, cells, and the like), in vivo or in vitro. The tissue types that can be studied using the methods of the present disclosure include, but are not limited to, myocardial tissues, nervous tissue, lymphoid tissue, skeletal and smooth muscle tissue, bones and cartilages, tissues of various organs (e.g., the kidney, the liver, the spleen, the prostate, the uterus, the testicles, and the ovaries), and select portions of each.

The methods of the disclosure can use one or more types of detecting or imaging systems such as, but not limited to, magnetic resonance imaging (MRI), SPECT, PET, ultrasound, X-ray, CAT, optical imaging, and combinations thereof. The contrast agent is a multimodality contrast agent that includes a polypeptide having optical properties (GFP). Thus, the polypeptide having optical properties can be detected using optical imaging, while the metal can be detected using another technique such as a MRI system.

In general, the contrast agents of the disclosure may be administered to a host using one or more techniques or routes (e.g., oral, mucosal, parenteral, and the like). After an appropriate amount of time, the host can be introduced to an appropriate detection or imaging system. The detection or imaging system can detect the contrast agent. In particular, the detection or imaging system can detect the location(s) of the contrast agents, the concentration of the contrast agent, and the like. The information obtained from the detection or imaging system can be used to create or form an image of the host or a portion thereof. The image would include the position and/or concentration of the contrast agent in the host.

The contrast agents can be used to study, image, diagnose the presence of, and/or treat cancerous cells or tissue, precancerous cells or tissue, cancer, or tumors. For example, the presence and location of the cancerous cells or tissue, precancerous cells or tissue, cancer, or tumors can provide insight into the appropriate diagnosis and/or treatment. It should be noted that contrast agents could include target-specific moieties specific for other diseases or conditions so that other diseases or conditions can be imaged, diagnosed, and/or treated using contrast agents of the present disclosure. Other diseases and/or conditions can be studied, imaged, diagnosed, and/or treated in a manner consistent with the discussion below as it relates to cancerous cells, precancerous cells, cancer, and/or tumors. The contrast agent is administered to the host in an amount effective to result in uptake of the contrast agent into the cancerous cells or tissue, precancerous cells or tissue, cancer, or tumors.

The contrast agents of the disclosure may include a target-specific moiety having an affinity for a specific cancer or cell type. Detecting the presence of the contrast agent, in particular, the presence of the contrast agent at the typical location of the specific cancer can be used in the diagnosis of the presence of the cancer (or vice versa). Imaging the host over a time period (e.g., days, weeks, months, or years) can provide information about the progression of the cancer or other disease or condition.

The contrast agent or compositions including the contrast agent may be administered to a subject in an amount effective to achieve the desired result at the appropriate dosages and for the desired periods of time. An effective amount of the contrast agent or compositions may vary according to factors such as the age, body weight, general health, sex, and diet of the host; the time of administration; the route of administration; the rate of excretion of the specific compound employed; the duration of the treatment; the existence of other drugs used in combination or coincidental with the specific compositions employed; the ability of the composition to elicit a desired response in the subject; and like factors well known in the medical arts. An effective amount is also one in which any toxic or detrimental effects (e.g., side effects) of the contrast agent or compositions are outweighed by the therapeutically or diagnostically beneficial effects. The contrast agent or compositions of the disclosure may be administered at a concentration of, for example, about 1 to 3.0 μmole/kg or about 6-20 mM.

Structure Descriptions for Protein Contrast Agents (ProCAs)

Advantageous contrast agents with high relaxivity in in vivo imaging capability of diseases including cancer and liver metastasis have several criteria: (1) high relaxivity; (2). high distribution in liver; (3). permeability to the liver tissue but low permeability to the metastatic tumor tissue (these features improving the ratio of MRI liver signal intensity to tumor signal intensity); (4) ability to alter the signal from both $T_1$- and $T_2$-weighted MR images, so that detected tumor under $T_1$ weight MRI can be further validated by $T_2$-weight MRI. If the tumor is too is small, $T_2$-weighted MRI without a contrast agent is not able to show the tumor enhancement. An MRI contrast agent with good $r_2$ is able to decrease the liver signal which can improve the tumor detection using $T_2$ weighted MRI sequences; (5). An ideal MRI contrast agents should have stability and strong metal selectivity to avoid $Gd^{3+}$ release; (6). good pharmacokinetics; and (7) no toxicity. To increase selectivity, we have also add targeting moieties for the ProCAs of the disclosure (SEQ ID NOs.: 1-17, 21 and 22).

MRI contrast agents with high relaxivity and desired liver retention time have been achieved by directly engineering $Gd^{3+}$ binding sites into proteins with appropriate surface modification and based on following rationales. First, to achieve maximal value of r1 relaxivity of Gd contrast agents at medical field strength, a correlation time of the Gd binding of about 10 ns is needed. This can be achieved by embedding a Gd binding site in a fixed protein frame with a size between 10-20 Kda. Based on simulations of contrast agents (Xue et al., (2013) *Nanomed. Nanobiotech.* 5: 163-179, incorporated herein by reference in its entirety), the protein environment has the addition of a secondary water shell that also contributes to the increase of relaxivity. High relaxivity can be improved by the three key factors of $\tau_c$, q, and outer coordinate shell contributions. Second, the engineered metal binding sites should have strong metal binding affinity for Gd and metal selectivity for Gd over physiological metal ions such as $Ca^{2+}$, $Mg^{2+}$, $Zn^{2+}$, etc. Advantageously, metal binding affinity constants especially for metal selectivity (or kinetic selectivity) should be comparable or stronger than currently available ones to overcome the NSF effect associated with the Gd toxicity.

Accordingly, for the design of MRI contrast agents of the disclosure from protein with high thermodynamic stability, several proteins such as, but not limited to, parvalbumin (ProCA3 series), calmodulin (ProCA2 series) and their variants were selected as scaffold polypeptides for their high thermostabilities, high solubilities, high resistances to the enzyme cleavage, and high tolerance of mutations. Based on extensive analysis of structural parameters such as the ligand types, coordination numbers, water numbers, bond angles and lengths of different classes of metal binding sites in proteins and small chelators and key determinants for metal binding affinity, selectivity, conformational change, and dynamic properties of metalloproteins (see refs 2-10) $Gd^{3+}$ binding sites were generated with desired Gd relaxation properties. Third, modifying protein surface by PEGylation allowed to increase blood retention time and increase liver preference (refs 10-12).

Thus, the metal binding sites of the protein based MRI contrast agents of the disclosure are formed by the following component: (1) one or more metal ions (such as, $Gd^{3+}$, $Eu^{3+}$, $Tm^{3+}$, $Yb^{3+}$, $Lu^{3+}$, $Mn^{2+}$, $Fe^{3+}$,) that is chelated by 4-9 oxygen ligand atoms and at least one of them from the scaffold polypeptide. The distance between metal and oxygen ligand from both water and protein is between about 2 Å to about 5 Å in all of the protein-based MRI contrast agents. $H_2O$ water molecules within 10 Å of the $Gd^{3+}$ forms a secondary shell or outer sphere that also contributes to the relaxivity. PEG chain(s) is/are covalently linked to the scaffold polypeptide to increase blood retention time, and/or increase solubility and or relaxation, reduce immunogenicity, and/or to increase liver preference.

In the contrast agents of the disclosure, advantageous metal binding sites are the residues in shown in bold in FIG. 1.

ProCA32 has High Serum Stability:

ProCA3 was bacterially expressed and purified without using an affinity tag, as described in refs 13 and 14, incorporated herein by reference in their entireties. It is important that the ProCA3 variants are resistant to cleavage by serum enzymes and maintain intact structure before secreted out of the body. To evaluate the stability of ProCA32, ProCA32 was incubated in 50% serum and then analyzed by SDS-PAGE and mass spectrum, as shown in FIG. 2. ProCA32 was very stable in the serum for at least 3 days. After three days, the proteins in the serum were degraded, although detectable ProCA32 was still found even after 12 days. Immuno-blot and mass spectrum analysis also applied to detect the serum stability of ProCA32 and ProCA32-PEG. All of these data shows that ProCA32 is stable in serum of at least three days. ProCA32 has an excretion half liver around 2.8 hours and clearance about 0.13 l/kg in mice. Such high stability of ProCA32 is essential for the safety profile of ProCA32.

ProCA32 has High $Gd^{3+}$ Stability and Metal Selectivity:

The metal binding affinity and selectivity of engineered ProCA were determined using several spectroscopic methods. The $Tb^{3+}$-binding affinity of calcium-binding protein was measured by $Tb^{3+}$-chelator buffer system. Free metal concentration was carefully controlled by the ratio of metal with chelators from 0 to 1. After measuring the $K_d$ of $Tb^{3+}$, the $K_d$ of $Gd^{3+}$ to ProCA was measured by $Gd^{3+}$ competition methods. The binding affinity $K_d$ for $Gd^{3+}$ for ProCA32 was $2.79\pm0.36\times10^{-22}$, which is comparable to that with DTPA.

ProCA32 exhibits $10^{11}$-fold higher $Tb^{3+}$ and $Gd^{3+}$ binding affinity compared with the wild type protein scaffold, which indicated that a negative-charged side chain in position 5 is essential for strong binding of $Gd^{3+}$ by EF-protein, as shown in FIG. 3). Addition of different concentrations of 10 µM of ProCA32 in $Gd^{3+}$ loaded Fura-2 (20 µM), resulting the change of fluorescence wavelength shifted from 380 nm to 340 nm and change of Fura-fluorescence shifted to 280 nm by competition, further verifying its stronger Gd affinity than Fura-2.

The thermodynamic stability constants of physiological metals ions to the contrast agents of the disclosure were determined. ProCA32, showed desired metal selectivity. Metal selectivity in ProCA3 mutant dramatically increased $Gd^{3+}$ selectivity over physiological metal ions ($Zn^{2+}$, $Ca^{2+}$ and $Mg^{2+}$), compared with WT and other mutations, and this increase of $Gd^{3+}$ selectivity was mostly contributed by the dramatic increase of $Gd^{3+}$ binding affinity in position 5 of EF-hand I.

The metal binding affinity of ProCA variants for $Ca^{2+}$ and $Mg^{2+}$ were measured by $M^{2+}$-EGTA buffer system, as described in Refs 13-18, incorporated herein by reference in their entireties. The metal selectivity for Gd over $Ca^{2+}$ of ProCA3 is about 3 fold of DTPA or the commercially available Eovist®. The metal selectivity for Gd over Mg was about 2-fold higher than that of DTPA measured by Fluozin-1 competition method; the selectivity of $Zn^{2+}$ over $Gd^{3+}$ was 14.3, which is about 10-fold higher than that of DTPA. Thus, the contrast agents of the disclosure and especially the proCA3 series have strong metal stability and kinetic stability against transmetalogization that is associated with NSF.

Figure 5:
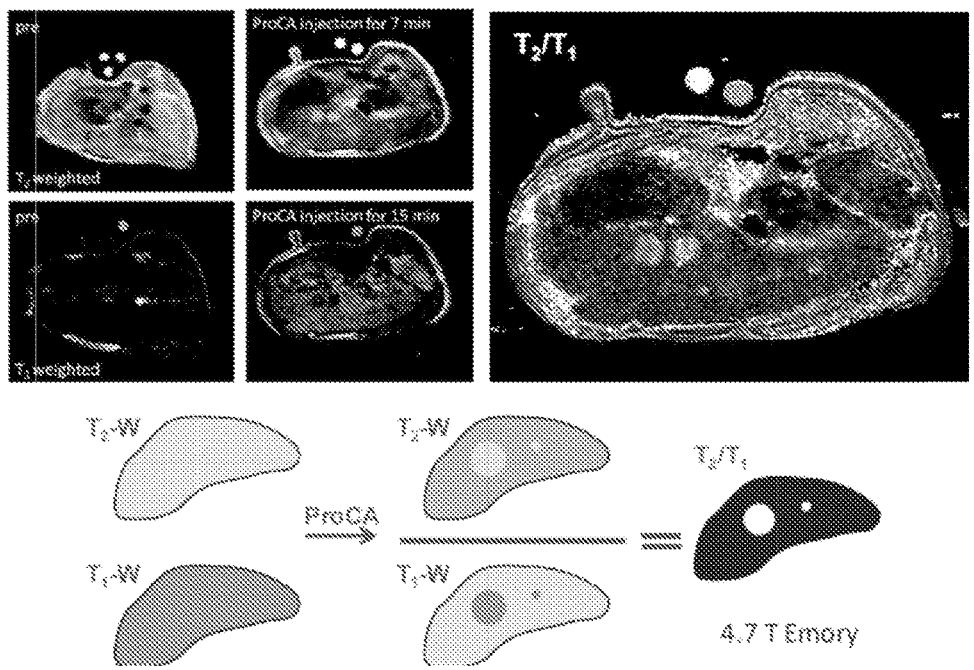
FIG. 5 illustrates liver tumor detection by T2/T1 ratiometric changes after injection of ProCA32M.
Figure 6:
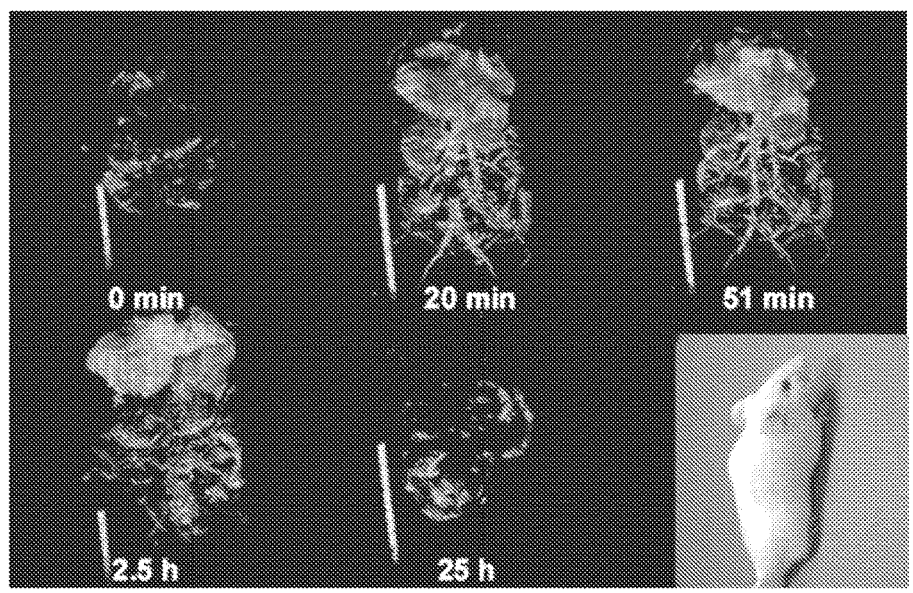
FIG. 6 is a series of digital images showing three-dimensional MRI with intravenous injection of ProCA32M that was PEGylated with PEG chains.
Figure 7:
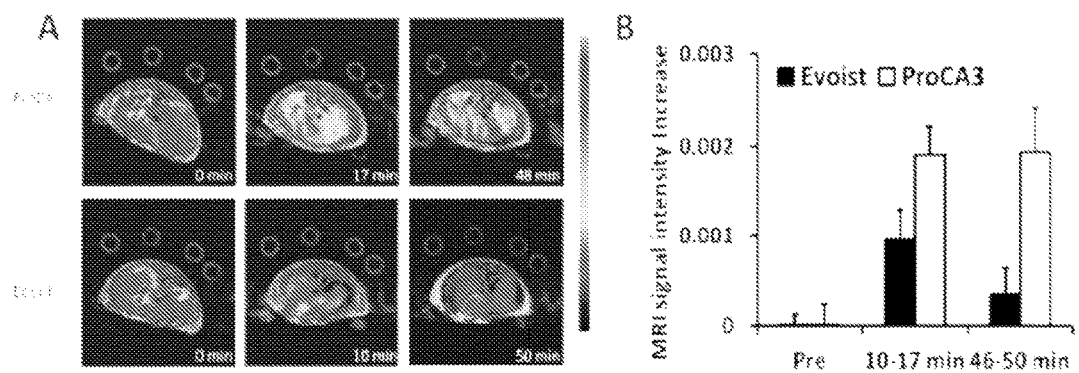
FIG. 7A is a series of digital images showing a comparison between ProCA32 and a clinically approved contrast agent.
FIG. 7B is a graph showing a comparison of signal intensity increases between ProCA32 and a clinically approved contrast agent.
Figure 8:
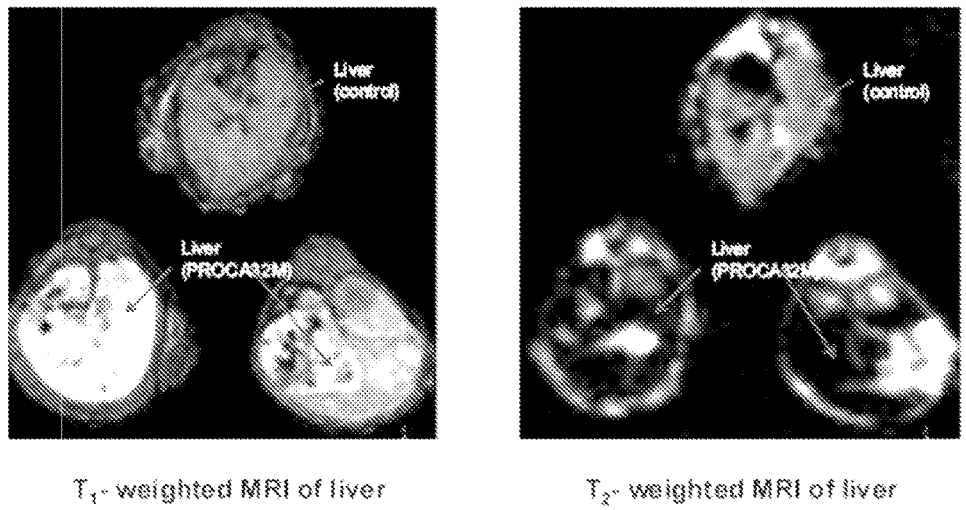
FIG. 8 is a pair of digital images showing T1 and T2 MR imaging of mice liver.
Figure 9:
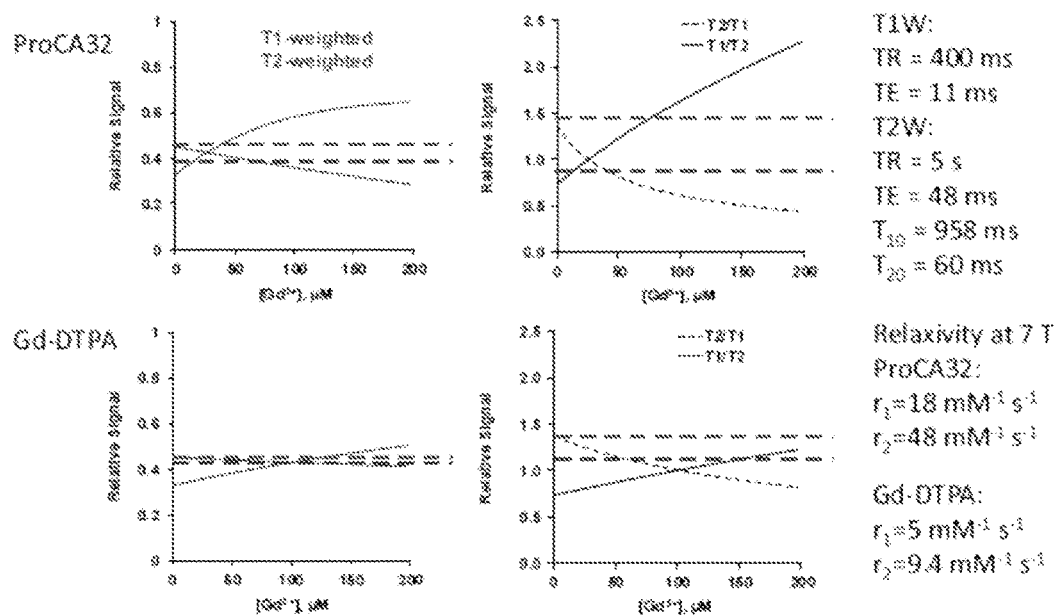
FIG. 9 is a series of graphs illustrating a simulation showing that ratiometric imaging improves the dynamic range MRI signal in liver.
Figure 10:
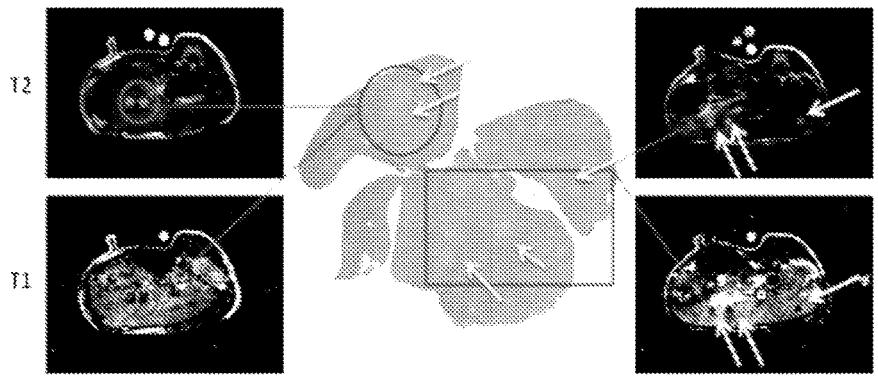
FIG. 10 illustrates imaging of liver metastases by both T1- and T2-weighted sequences.
Figure 11:
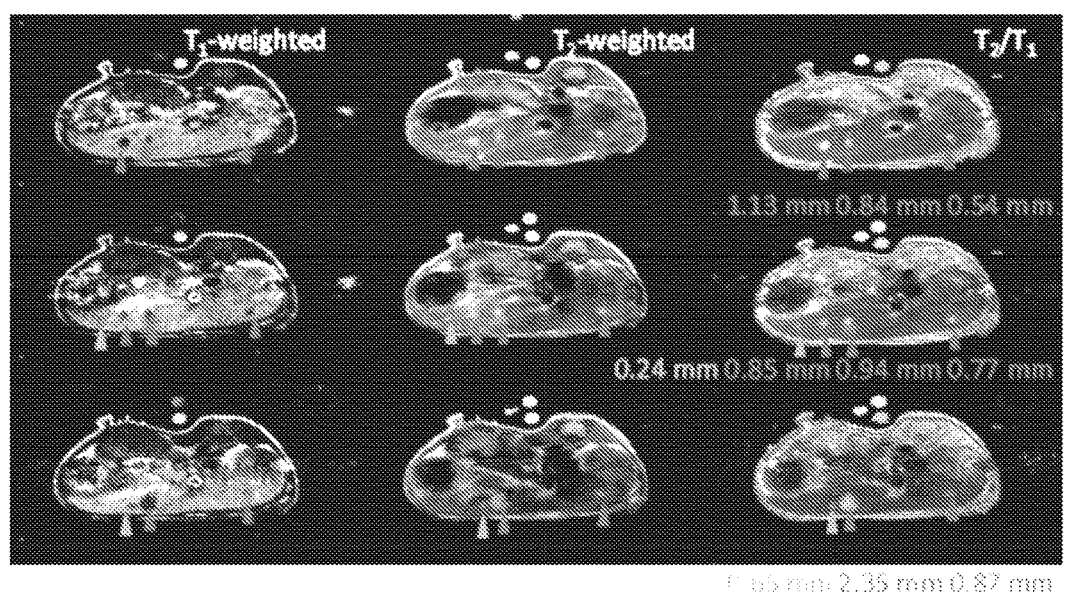
FIG. 11 illustrates the detection of metastases with a size less than 0.25 $mm^2$.
Figure 12:
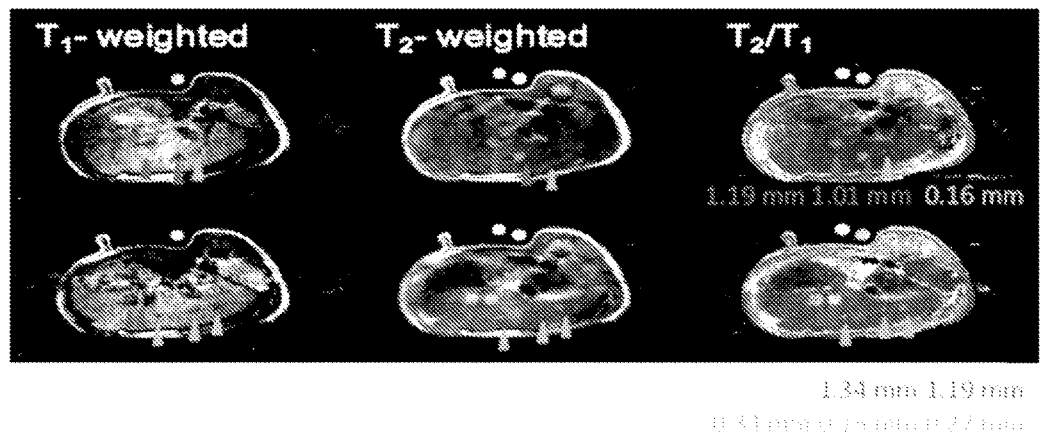
FIG. 12 illustrates the detection of metastases with a size less than 0.25 $mm^2$.
Figure 13:
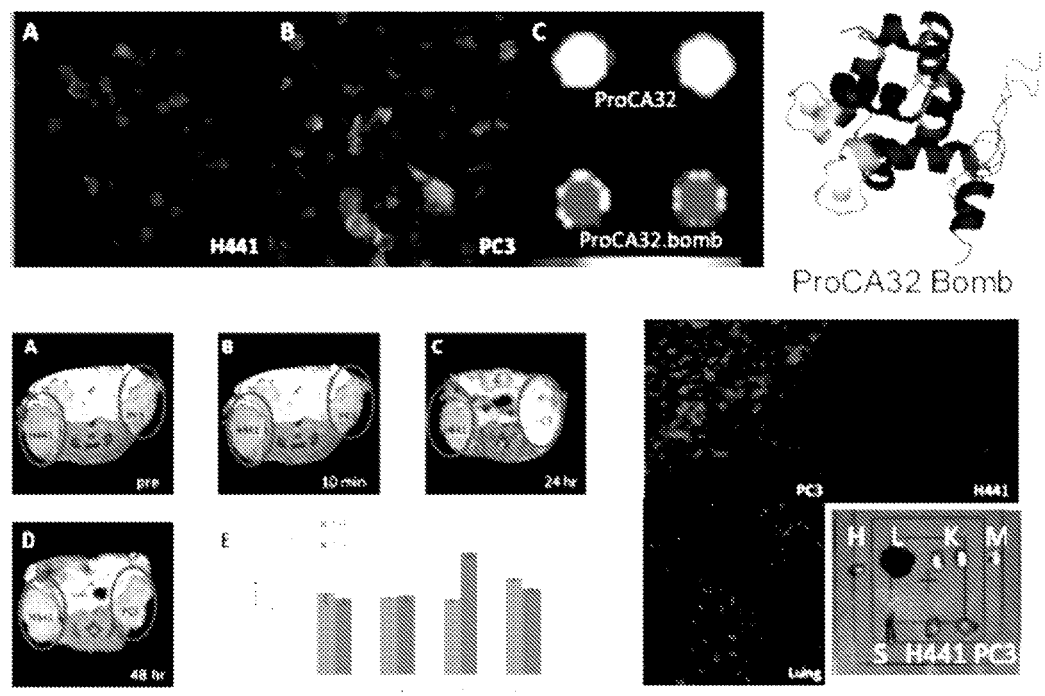
FIG. 13 illustrates molecular imaging of GRPR by ProCA3 variants.

MRI Methods Including Ratiometric Methodology for ProCAs:

ProCA variants of the disclosure have both high relaxivity for r1 and r2. For example, ProCA32 has a per Gd $r_2$ of 40 mmol$^{-1}$ s$^{-1}$ per particle and an $r_2$ of 40 mmol$^{-1}$ s$^{-1}$, (as shown in FIG. 4). Thus, they are advantageous for both T1 and $T_2$-weighted MRI imaging. In addition, all of ProCA contrast agents of the disclosure have advantageous half-lives and blood retention times ranging from about 20 min to 90 h in animals, depending on the surface modifications such as using different lengths of PEGylation chain. Accordingly, there are several ways to perform high quality MRI imaging for animals and human, such as, but not limited to the following:

r1 and r2 Weighted Imaging within a Single or Separate Injection:

For example, as shown in FIG. 5, 7 min after injection of ProCA32 into the tail vein of a mouse, the liver became darker, as imaged by $T_2$-weighted sequence. $T_1$-weighted sequence spin echo was then used with the same mice, the liver showing enhanced an MR signal at 15 min.

Quantitatively, ProCA32 with PEGylation 40 has 40% higher signal enhancement under $T_1$ weighted MRI sequence and 200% higher signal decrease under $T_2$-weighted MRI sequence. Thus, the contrast agent ProCA32 is able to image liver with both $T_1$- and $T_2$-weighted sequences with high contrast and high imaging quality in a single injection administration. Because the enhanced T1- and T2-weighted images have different effects of imaging contrast (brighter or darker, respectively), there is an enhanced probability of detecting the targeted tumor tissue. In contrast, the currently available approved liver contrast agents such as Eovist® have a very short fast phase (sec.) and liver uptake phase (approximately 3 min) in human. The mouse halftime is much shorter. Due this limitation, with these agents, it is not possible to obtain both high quality imaging for small animal. For human, their applications are also limited by their low relaxivity and short half-life. It is possible to obtain very high quality imaging by applying our contrast agent to both low and high field strengths such as 0.47-9.4 T.

Ratiometric Applications to Selectively Enhance the Tumor:

The contrast agents of the disclosure are also advantageous to enhance signal to noise ratio (S/N ratio) by optimizing a pulse sequence that first suppresses liver signal with inversion recovery and enhances tumor/liver contrast by T2-weighted with long TE during the liver-uptake (blood) phase upon injection of contrast agents. In this example, the signals from liver or organs with contrast agent can be suppressed and the tumor can be selectively enhanced. Any artifacts or challenges in imaging due to breath or motions associated to the organs can be effectively reduced or suppressed.

Both T1- and T2-weighted imaging may be performed separately and then process the imaging data as a T2/T1 ratiometric imaging, as shown in FIG. 5. Because ProCA variants can effectively decrease MRI signal in T2-weighted MRI and effectively increase MRI signal in T1-weighted MRI, the ratio between T2-weighted MRI and T1-weighted MRI after application of MRI contrast agents can further improve the dynamic range of the MRI signal change.

Accordingly, ratiometric imaging reduces the background and improves the sensitivity of ProCA in MRI. Thus, T2/T1 (T1/T2) ratiometric MRI can improve at least 10 times higher sensitivity than that of T1-weighted or T2-weighted MRI after injection of ProCA. ProCA can also be used to detect other liver diseases such as, but not limited to, uveal melanoma metastasis, primary liver tumor HCC, dysplasia, liver fibrosis, alcohol liver, NASH. Accordingly, the contrast agent of the disclosure are advantageously allow for MRI image enhancement by the generation of a ratiometric image (T1/T2) that the current image contrast agents are unable to provide. Current agents exhibit enhanced T1 or T2, but not both together. Other reported MRI contrast agents can change single type of MRI signals i.e. either T1-weighted such as Eovist® and Magnivest, or T2-weighted MRI such as iron oxide nanoparticles, but not both. Thus, they cannot be used for T2/T1 (T1/T2) ratiometric imaging.

Ratiometric Targeting Imaging:

Biomarker-targeted contrast agents of the disclosure (SEQ ID Nos.: 1-22, or conservative variants thereof) have the capability to also selectively bind to biomarkers expressed in the tumor cells due to the addition of target-specific ligands attached to the contrast agent scaffolds. Since they have also both high r1 and r2 relaxivity values, the tumor contrast can be enhanced at the tumor targeting phase by using inversion recovery with a long inversion time. The tumor targeting phase is usually a few hours after injection at which time contrast agents located on, in, or nearby normal cells are washed away, while they remain in the tumor due to specific binding. This method is very selective, it allows to identify the tumor types by biomarker types without invasive biopsy-coupled IHC staining. In addition, it allows selection of those patients able to benefit from targeted therapy. Further, it also allows monitoring an administered treatment by MRI. Furthermore, the contrast agents of the disclosure have applications in imaging-guided local treatment and drug deliver such as laser ablation or drug treatment.

DCE-MRI with Improved Kinetics Tumor, Blood Vessel and Organ Dynamic Properties:

Dynamic-contrast-enhanced MRI (DCE-MRI) is a non-invasive tool to probe tumor vasculature by mathematically modeling and calculating contrast accumulation in the tumor over time. The current clinically available MRI contrast agents, such as Gd-DTPA, have been applied to evaluate the tumor vasculature of many types of cancers, such as breast cancer, pancreatic cancer, as described in ref 17. This technique is advantageous to monitor the tumor vasculature changes of the patients after tumor treatment with anti-angiogenesis drugs. DCE-MRI is also widely applied as an advanced technique in the to evaluate the effects of angiogenesis drugs. Due to the non-invasive properties, applications of DCE-MRI decrease numbers of experimental animals and the cost in preclinical drug development.

Current DEC-MRI methods still have some limitations. First, to accurately calculate the blood volume and blood vessel permeability, most DCE-MRI methods require accurately measuring the arterial input function (AIF), the contrast agent concentration in the artery at different time points post injection. The AIF of current clinically available MRI contrast agents, however, is extremely difficult to be measured accurately due to their short blood half-lives and their fast excretion, as described in Ref 18. For example, the blood half-life for Gd-DTPA is only 2 min in mice and 10 min in human. There are difficulties to determining contrast agents in the blood very accurately in such a short time. Second, due to the small size and fast tumor penetration, DCE-MRI is not able to differentiate the leakage size using current clinically available MRI contrast agents. Third, current MRI contrast agents have short time accumulations and short time releases in tumor, which restrict the amount of data collection in the limited time period available.

Compared with currently available current clinically available MRI contrast agents, the ProCA contrast agents of the disclosure have several advantages for use in the DCE-MRI procedures. First, the concentration of ProCAs in the blood is more stable, which made it easier to measure AIF with a reduced error. In addition, ProCAs have much longer accumulation times in the tumor, which simplifies the mathematical model. Further, ProCAs can selectively pass certain blood vessels with a leakage larger than ProCAs. Furthermore, ProCAs have higher relaxivity, which can improve the sensitivity and dose efficiency of contrast agents. Since DCE-MRI can also be applied to imaging other abnormal tissue, ProCAs can also be used for the DCD-MRI of other type of diseases, such as stroke and liver kidney.

Functional Magnetic Resonance Imaging (fMRI):

During a brain activity following a sensory stimulation, a variety of changes occur, such as regional ionic concentrations, cerebral blood volume (CBV), and the glutamate responses. CBV, defined as milliliters of blood per 100 ml of brain tissue, is an important indicator of brain function (refs. 21-24). The CBV-weighted fMRI, including DSC-MRI and VASO-MRI has been playing an important role in understanding brain physiology and pathophysiology (refs. 25-27). Many disease conditions including brain tumors, Alzheimer's diseases, arteriovenous malformations and acute stroke are related to abnormal CBV values (see refs 25, and 28-32).

For functional brain imaging, absolute CBV (aCBV) maps can provide important information about CBV abnormalities in a single patient. Absolute CBV, often obtained by the DSC-MRI approach, which uses a paramagnetic contrast agent (Gd-based complexes) given by i.v. route applies a rapid image acquisition sequence to monitor the MR signal intensity during the first passage of the agent through the microvasculature (refs 29, and 33-36).

Relative CBV (rCBV) can also be obtained by VASO-MRI. It can provide maximal signal difference between pre- and post-contrast situations with advantages over a CBV measurement without requiring the measurement of the contrast agent concentration in the incoming arterial blood (ref. 25). Current measurement of CBV with both MRI techniques relies on the employment of small molecule-based Gd-DTPA as a contrast agent (refs. 25-27, and 37). The accurate measurement of CBV is limited by low relaxivity and short vascular retention time. It is remains necessary, therefore, to develop MRI contrast agents with significantly higher relaxivity and longer vascular retention time so as to measure CBV with both MRI techniques to detect brain responses at high resolution and accuracy.

The second change for brain and neural imaging is that the endogeneous contrast agent (blood-oxygen-level)-based fMRI lacks temporal resolution of electrophysiology. Mainly due to low relaxivity of current contrast agents, it was concluded that it is impossible to apply MRI to monitor biomarkers to monitor specific brain events due to limited numbers of the biomarkers in the brains.

However, the protein-based contrast agents of the disclosure can be advantageously used to monitor brain function. Flashing light simulation, the CBV, the glutamate response, and contrast agent-based fMRI signals from their primary visual (V1) cortices can be measured. The respective average V1 responses for a visual stimulation and be determined and compared during various types of brain activity. In addition, ProCA contrast agents can be distributed in blood for at least 30 min with very stable enhancement of blood vessel and heart. Any abnormality of blood and heart can change the volume of blood in these disease regions. Cerebral blood volume changes during brain activity. Such blood volume change can be monitored by the ProCAs of the disclosure with applications to detect cardiovascular disease such as coronary heart disease, pulmonale, congenital heart defect, cardiomyopathy, myocardial infarction, congestive heart failure, vascular heart disease, arrhythmia, peripheral arterial disease, cerebrovascular accident rheumatic heart disease. Further, cardiovascular disease has specific biomarker expression, such as integrin and selectin. These biomarkers can be targeted by ProCA covalently linked with biomarker targeting peptide.

Dosage Forms

Unit dosage forms of the contrast agents of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the contrast agents of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

Typical compositions including the contrast agent and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions including the contrast agent and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

Like the amounts and types of excipients, the amounts and specific type of active ingredient in a dosage form may differ depending on various factors. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

Accordingly, one aspect of the disclosure encompasses embodiments of a protein contrast agent for enhancing an MRI image, the protein contrast agent comprising: (i) a polypeptide having a conformation presenting at least five oxygen atoms positioned to chelate at least one paramagnetic metal ion selected from the group consisting of $Gd^{3+}$, $Eu^{3+}$, $Tm^{3+}$, $Yb^{3+}$, $Lu^{3+}$, $Mn^{2+}$, and $Fe^{3+}$, and wherein (a) each oxygen atom interacting with the metal ion can be between about 2 angstrom units and about 5 angstrom units from the metal ion; (b) the metal ion can have at least one water molecule electrostatically interacting therewith and at a distance of less than about 10 angstrom units therefrom, and wherein the polypeptide can include a target-specific moiety attached thereto; (ii) at least one polyethylene glycol molecule attached to the polypeptide; and (iii) at least one paramagnetic metal ion chelated to the polypeptide, wherein the protein contrast agent, when administered to a human or non-human animal can provide an enhanced MRI image allowing the determination of a T2/T1 or T1/T2 MRI intensity ratio, and wherein the metal ion or ions can be chelated to a beta-fold region of the polypeptide or at least one loop and an alpha-helix, wherein the protein contrast agent can provide an image of a tumor having a size less than about 0.25 microns, and wherein the target-specific moiety can be specific for a cell-specific target selected from the group consisting of: a hepatic tumor, a renal tumor, and a cardiovascular-specific target, and wherein the protein contrast agent can have an amino acid sequence having at least 85% similarity to a sequence selected from the group consisting of: SEQ ID Nos.: 1-22, or conservative variants thereof.

In embodiments of this aspect of the disclosure, the protein contrast agent can have an amino acid sequence having at least 90% similarity to a sequence selected from the group consisting of: SEQ ID Nos.: 1-22, or conservative variants thereof.

In embodiments of this aspect of the disclosure, the protein contrast agent can have an amino acid sequence having at least 95% similarity to a sequence selected from the group consisting of: SEQ ID Nos.: 1-22, or conservative variants thereof.

In embodiments of this aspect of the disclosure, the protein contrast agent can have an amino acid sequence selected from the group consisting of: SEQ ID Nos.: 1-22, or conservative variants thereof.

In embodiments of this aspect of the disclosure, the protein contrast agent can have an amino acid sequence selected from the group consisting of: SEQ ID Nos.: 1-22.

Another aspect of the disclosure encompasses embodiments of a pharmaceutically acceptable composition formulated for administration to a human or non-human animal for use as an MRI imaging contrast agent, said composition comprising a protein contrast agent having an amino acid sequence having at least 85% similarity to a sequence selected from the group consisting of: SEQ ID Nos.: 1-22, or conservative variants.

Another aspect of the disclosure encompasses embodiments of a method of obtaining an MRI image of a tissue, said method comprising the steps: (a) administering to a human or non-human animal a pharmaceutically acceptable dose of a protein contrast agent, wherein said protein contrast agent comprises: (i) a polypeptide having a conformation presenting at least five oxygen atoms positioned to chelate at least one paramagnetic metal ion selected from the group consisting of $Gd^{3+}$, $Eu^{3+}$, $Tm^{3+}$, $Yb^{3+}$, $Lu^{3+}$, $Mn^{2+}$, and $Fe^{3+}$, and wherein (a) each oxygen atom interacting with the metal ion is between about 2 angstrom units and about 5 angstrom units from the metal ion; (b) the metal ion has at least one water molecule electrostatically interacting therewith and at a distance of less than about 10 angstrom units therefrom, and wherein the polypeptide includes a target-specific moiety conjugated thereto; (ii) at least one polyethylene glycol molecule attached to the polypeptide; (iii) at least one paramagnetic metal ion chelated to the polypeptide; and (iv) a pharmaceutically acceptable carrier; (b) subjecting the human or non-human animal to MRI, thereby obtaining a T1 and a T2 determination; (c) determining the T2/T1 or T1/T2 intensity ratio of the MRI image; and (d) obtaining an image of the T2/T1 or T1/T2 intensity ratio relative to a tissue of the human or non-human animal, thereby determining the location of the protein contrast agent in the human or non-human animal, thereby identifying a target tissue.

In embodiments of the method of this aspect of the disclosure, (i) in the protein contrast agent the metal ion or ions can be chelated to a beta-fold region of the polypeptide or at least one loop and an alpha-helix; and (ii) the protein contrast agent can provide an image of a hepatic tumor having a size less than about 0.25 microns.

In embodiments of the method of this aspect of the disclosure, the target-specific moiety can be specific for a target selected from the group consisting of: a hepatic tumor, a renal tumor, and a cardiovascular-specific target.

In embodiments of the method of this aspect of the disclosure, the protein contrast agent can comprise a polypeptide having an amino acid sequence having at least 90% similarity to a sequence selected from the group consisting of: SEQ ID Nos.: 1-56, or conservative variants thereof.

In embodiments of the method of this aspect of the disclosure, the protein contrast agent can comprise a polypeptide having an amino acid sequence having at least 90% similarity to a sequence selected from the group consisting of: SEQ ID Nos.: 1-22, or conservative variants thereof.

In embodiments of the method of this aspect of the disclosure, the protein contrast agent can comprise a polypeptide having an amino acid sequence having at least 95% similarity to a sequence selected from the group consisting of: SEQ ID Nos.: 1-56, or conservative variants thereof.

In embodiments of the method of this aspect of the disclosure, the protein contrast agent can comprise a polypeptide having an amino acid sequence having at least 95% similarity to a sequence selected from the group consisting of: SEQ ID Nos.: 1-22, or conservative variants thereof.

In embodiments of the method of this aspect of the disclosure, the protein contrast agent can comprise a polypeptide having an amino acid sequence selected from the group consisting of: SEQ ID Nos.: 1-56, or conservative variants thereof.

In embodiments of the method of this aspect of the disclosure, the protein contrast agent can comprise a polypeptide having an amino acid sequence selected from the group consisting of: SEQ ID Nos.: 1-22, or conservative variants thereof.

Still another aspect of the disclosure encompasses embodiments of a method of producing a protein contrast agent, said method comprising the steps of: (a) obtaining a genetically modified cell comprising an expression vector expressing a polypeptide having an amino acid sequence selected from the group consisting of: SEQ ID Nos.: 1-56, or a conservative variant thereof; (b) culturing said genetically modified cell in a culture medium under conditions allowing the expression of the polypeptide by cultured cells; (c) isolating the cultured cells from the medium and disrupting said isolated cell thereby generating a cell lysate; (d) separating cell debris from the cell lysate; and (e) incubating the cell lysate at 80-100° C. for about 5-20 min, centrifuging to obtain a supernatant, and either (i) precipitating undesired proteins using streptomycin, polyethylene glycol, or ammonium sulfate, and isolating the protein contrast agent by ion exchange column.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

REFERENCES

1. Xue, S., Qiao, J., Pu, F., Cameron, M. & Yang, J. J. Design of a novel class of protein-based magnetic resonance imaging contrast agents for the molecular imaging of cancer biomarkers. *Wiley interdisciplinary reviews. Nanomedicine and nanobiotechnology* 5, 163-179 (2013).
2. Pidcock, E. & Moore, G. R. Structural characteristics of protein binding sites for calcium and lanthanide ions. *J Biol Inorg Chem* 6, 479-489 (2001).
3. Kirberger, M. et al. Integration of Diverse Research Methods to Analyze and Engineer Ca-Binding Proteins: From Prediction to Production. *Curr Bioinform* 5, 68-80 (2010).
4. Yang, W. et al. Rational design of a calcium-binding protein. *J Am Chem Soc* 125, 6165-6171 (2003).
5. Yang, W., Wilkins, A. L., Li, S., Ye, Y. & Yang, J. J. The effects of $Ca^{2+}$ binding on the dynamic properties of a designed $Ca^{2+}$-binding protein. *Biochemistry* 44, 8267-8273 (2005).
6. Yang, W. et al. Design of a calcium-binding protein with desired structure in a cell adhesion molecule. *J Am Chem Soc* 127, 2085-2093 (2005).
7. Maniccia, A. W., Yang, W., Li, S. Y., Johnson, J. A. & Yang, J. J. Using protein design to dissect the effect of charged residues on metal binding and protein stability. *Biochemistry* 45, 5848-5856 (2006).
8. Li, S. et al. Rational design of a conformation-switchable $Ca^{2+}$- and $Tb^{3+}$-binding protein without the use of multiple coupled metal-binding sites. *The FEBS journal* 275, 5048-5061 (2008).

9. Jones, L. M. et al. Rational design of a novel calcium-binding site adjacent to the ligand-binding site on CD2 increases its CD48 affinity. *Protein Sci* 17, 439-449 (2008).
10. Yang, J. J. et al. Rational design of protein-based MRI contrast agents. *J Am Chem Soc* 130, 9260-9267 (2008).
11. Li, S. et al. PEGylation of protein-based MRI contrast agents improves relaxivities and biocompatibilities. *J Inorg Biochem* 107, 111-118 (2012).
12. Qiao, J. et al. HER-2 targeted molecular MR imaging using a de novo designed protein contrast agent. *PLoS One* 6, e18103 (2011).
13. Henzl, M. T. Characterization of parvalbumin and polcalcin divalent ion binding by isothermal titration calorimetry. *Methods Enzymol* 455, 259-297 (2009).
14. Henzl, M. T., Agah, S. & Larson, J. D. Rat alpha- and beta-parvalbumins: comparison of their pentacarboxylate and site-interconversion variants. *Biochemistry* 43, 9307-9319 (2004).
15. Grynkiewicz, G., Poenie, M. & Tsien, R. Y. A new generation of $Ca^{2+}$ indicators with greatly improved fluorescence properties. *The Journal of biological chemistry* 260, 3440-3450 (1985).
16. Tanner, J. J., Agah, S., Lee, Y. H. & Henzl, M. T. Crystal structure of the D94S/G98E variant of rat alpha-parvalbumin. An explanation for the reduced divalent ion affinity. *Biochemistry* 44, 10966-10976 (2005).
17. Yokoyama, S., Inagaki, F. & Miyazawa, T. Advanced nuclear magnetic resonance lanthanide probe analyses of short-range conformational interrelations controlling ribonucleic acid structures. *Biochemistry* 20, 2981-2988 (1981).
18. Lee, J., Platt, S., Kent, M. & Zhao, Q. An analysis of the pharmacokinetic parameter ratios in DCE-MRI using the reference region model. *Magn Reson Imaging* 30, 26-35 (2012).
19. Mendichovszky, I. A., Cutajar, M. & Gordon, I. Reproducibility of the aortic input function (AIF) derived from dynamic contrast-enhanced magnetic resonance imaging (DCE-MRI) of the kidneys in a volunteer study. *Eur J Radiol* 71, 576-581 (2009).
20. Saito, K. et al. Assessing liver function using dynamic Gd-EOB-DTPA-enhanced MRI with a standard 5-phase imaging protocol. *J Magn Reson Imaging* (2012).
21. Belliveau, J. W. et al. Functional mapping of the human visual cortex by magnetic resonance imaging. *Science* 254, 716-719 (1991).
22. Mandeville, J. B. et al. Dynamic functional imaging of relative cerebral blood volume during rat forepaw stimulation. *Magn Reson Med* 39, 615-624 (1998).
23. Mandeville, J. B. et al. MRI measurement of the temporal evolution of relative CMRO(2) during rat forepaw stimulation. *Magn Reson Med* 42, 944-951 (1999).
24. Marota, J. J. et al. Investigation of the early response to rat forepaw stimulation. *Magn Reson Med* 41, 247-252 (1999).
25. Lu, H. et al. Novel approach to the measurement of absolute cerebral blood volume using vascular-space-occupancy magnetic resonance imaging. *Magn Reson Med* 54, 1403-1411 (2005).
26. Lu, H., Golay, X., Pekar, J. J. & Van Zijl, P. C. Functional magnetic resonance imaging based on changes in vascular space occupancy. *Magn Reson Med* 50, 263-274 (2003).
27. Lu, H., Clingman, C., Golay, X. & van Zijl, P. C. Determining the longitudinal relaxation time (T1) of blood at 3.0 Tesla. *Magn Reson Med* 52, 679-682 (2004).
28. Derdeyn, C. P. et al. Variability of cerebral blood volume and oxygen extraction: stages of cerebral haemodynamic impairment revisited. *Brain* 125, 595-607 (2002).
29. Essig, M. et al. Assessment of brain metastases with dynamic susceptibility-weighted contrast-enhanced MR imaging: initial results. *Radiology* 228, 193-199 (2003).
30. Harris, G. J. et al. Dynamic susceptibility contrast MRI of regional cerebral blood volume in Alzheimer's disease. *Am J Psychiatry* 153, 721-724 (1996).
31. Kader, A. & Young, W. L. The effects of intracranial arteriovenous malformations on cerebral hemodynamics. *Neurosurg Clin N Am* 7, 767-781 (1996).
32. Tomita, M. Significance of cerebral blood volume. In: Tomita M, Sawada T, Naritomi H, eds. Cerebral hyperemia and ischemia: from the standpoint of cerebral blood volume. p 3-30 (1988).
33. Duhamel, G., Schlaug, G. & Alsop, D. C. Measurement of arterial input functions for dynamic susceptibility contrast magnetic resonance imaging using echoplanar images: comparison of physical simulations with in vivo results. *Magn Reson Med* 55, 514-523 (2006).
34. Rosen, B. R., Belliveau, J. W., Vevea, J. M. & Brady, T. J. Perfusion imaging with NMR contrast agents. *Magn Reson Med* 14, 249-265 (1990).
35. Fossheim, S., Kellar, K. E., Fahlvik, A. K. & Klaveness, J. Low-molecular weight lanthanide contrast agents: evaluation of susceptibility and dipolar effects in red blood cell suspensions. *Magn Reson Imaging* 15, 193-202 (1997).
36. Fossheim, S., Saebo, K. B., Fahlvik, A. K., Rongved, P. & Klaveness, J. Low molecular weight lanthanide contrast agents: in vitro studies of mechanisms of action. *J Magn Reson Imaging* 7, 251-257 (1997).
37. Francis, S. T., Pears, J. A., Butterworth, S., Bowtell, R. W. & Gowland, P. A. Measuring the change in CBV upon cortical activation with high temporal resolution using look-locker EPI and Gd-DTPA. *Magn Reson Med* 50, 483-492 (2003).

EXAMPLES

Example 1

Method for Ratiometric Imaging

In the ratiometric imaging methods of the disclosure, ProCA contrast agents of the disclosure can cause the MRI signal intensity increase in T1-weighted MRI and cause a concomitant MRI signal intensity decrease in T2-weighted MRI. The ratio of the T2 intensity over T1 intensity (or T1/T2) of same position of tissue shows a significant change of the MRI signal when the ProCA concentration in the tissue changes.

The ratio metric imaging of MRI was obtained by the following steps before and after the injection of contrast agents: 1) collect T2-weighted image in MRI using T2-weighted MRI sequences by such as fast spin echo, or spin echo with long TR and TE; 2) collect T1-weighted imaging in MRI with the exact same location. These T1-weighted sequences include gradient echo or spin echo with short TR and TE; 3) Divide the intensity of T2-weighted MRI and T1-weighted MRI in each pixel to generate a new MRI image. This new generated image is called T2/T1 ratiometric imaging.

T2/T1 imaging by the method of the disclosure shows a significantly decreased MRI signal when the contrast agent concentration increases in tissues. In addition, we can generate T1/T2 imaging by dividing the intensity of T1-weighted MRI to T2-weighted MRI in each pixel. Such T1/T2 imaging shows an increased MRI signal when contrast agent concentration increase in tissues.

Example 2

Method for DCE-MRI

Dynamic contrast enhanced-MRI (DEC-MRI) data were acquired using a Varian 7 T MR scanner. A 26 G catheter was implanted into the tail vein of the mice before the scanning. The tissue of interest of the mouse was acquired in MRI with a set of MRI experiments including proton density map, T1 map and DCE-MRI sequence. The mice tissue included liver, kidney, tumor, brain, muscle and other tissue organs. $T_1$ map of mice tissue were acquired before contrast agent injection by saturation recovery FSEMS sequence with different lengths of TR, matrix: 256×256, fov=4 cm×4 cm and thickness=2 mm.

DCE-MRI was applied with FLASH sequence with 150 repeated scanning. 20 scans were acquired as baseline before contrast agent injection. DCE-MRI was acquired with following parameters: TR=18.80 ms, TE=2.95 ms, Flap Angel=25°, average=3; gain=25. The field view was 4 cm×4 cm with matrix of 128×128 and slice of 1 mm thickness. Data were acquired every 7 s. 0.015 mmol/kg ProCA (100 µl) was quickly injected after the twentieth scan, followed with the injection of 150 µl saline. Twenty rounds of scanning were acquired as baseline before the injection of contrast agents, and then a total volume of 100 µl of DTPA (0.2 mmol/kg) or ProCA (0.015 mmol/kg) was injected within 5 s in to the mice during scanning. A total of 150 rounds of scanning were final acquired within 7 s for ProCA in each round. The DCE-MRI data were processed by imaging software such as Matlab, Image J, and SPM.

Example 3

Expression and Purification Method

ProCAs were expressed in *E. coli* BL-21 DE3 or Tuner strains. The DNA plasmids of were transfected in *E. coli* bacteria. The ProCA-transfected *E coli* were grown in LB medium at 37° C. with constant shaking. ProCA expression was induced by IPTG after the $OD_{500}$ reached 0.6. After IPTG induction overnight, the bacteria were sonicated in 10 mM Tris-HCl buffer, pH 7.2, 100 µM PMSF and benzonuclease and followed by passing through a French pressure cell. The supernatant of cell lysate was incubated at 85° C. for 10 min, cooled to 4° C. in an ice-water bath, and centrifuged (17000 rpm, 20 min, 4° C.). The supernatant was collected for further purification. DNA was then precipitated by supplementation of 3% streptomycin sulfate. After dialysis for 24 h at 4° C. against 10 mM Tris/HCl at pH 8.5, the protein mixture was purified by the HiTrap Q column. After removing unbound proteins with 3 bed volumes of 10 mM Tris at pH 8.0, the column was eluted with a 0-1 M NaCl gradient in 10 mM Tis/HCl at pH 8.5. The protein and DNA separation were monitored by SDS-PAGE and agarose gel, respectively. The purified ProCA32 was dialyzed against 10 mM Tris, pH 8.5. Metals in ProCAs are removed by chelex-100 and the metal content in ProCAs analyzed by ICP-MS.

For large scale expression and purification, the plasmid encoding for ProCA3 was first transferred in BL21-DE3-plysS bacteria cultured on agar plate supplemented with ECAM media. 1 ml of a glycerol stock of ProCA32-expressing bacteria were inoculated in 100 ml ECAM and shake at 150 rpm and 37° C. overnight. Then, 10 ml of the bacteria was transferred to 250 ml ECAM medium and incubated at 37° C. and 200 rpm for 6 h. 120 ml of these bacteria were used as an inoculum for the bioreactor. The bioreactor were setup as follows: Initial glucose concentration 21 g/L; Batch media contained 50 µg/ml carbenicillin; vessel was inoculated to give $1.5 \times 10^{-2}$ cells; oxygen concentration was 30% and maintained with stirrer (min=160 rpm, max=450 rpm) and gas mix; air flow was constant at 10 LPM. Bacteria were harvested by continuous centrifugation.

The bacteria cell pellets were suspended by 10 mM HEPES, pH 7.0 and then disrupted by cell disrupter. After centrifugation at 6000 rpm for 30-60 min, the supernatant of bacterial lysate was collected for further protein purification. To separate ProCA3 from other proteins or biomolecules, such as DNA, different concentrations of PEG-8000 were added to the supernatant of the cell lysate.

The effective concentration range of PEG-8000 for ProCA32 precipitation was determined by SDS-PAGE. To further purify ProCA3, ProCA3 precipitation by PEG-8000 was dissolved in HEPES buffer at pH 7.0. These protein solutions were load to FPLC equipped with Hi-trap Q column. After binding to the column, the unbounded component was first washed with 7 column volumes (CV) of buffer A (10 mM HEPES buffer at pH 8.0). Then, buffer B (10 mM HEPES buffer, 1 M NaCl at pH 8.0) concentration was increased to 25% within 7 CV. The column was further washed with 25% of buffer B for 2 CV and then increase to 100% of buffer B of 1 CV to wash out every component bounded to the column. The fractions with ProCA32 elutions were determined by UV abs and SDS-PAGE. Finally, since ProCA32 is very stable at 90° C., the purified ProCA32 was incubated at 90° C. for 20 min followed by a centrifugation at 6000 rpm for 30 min to remove residue wanted protein.

PEGylation of ProCA:

ProCAs were PEGylated by the following steps: 1). ProCAs were dialyzed against 10 mM HEPES at pH 7.0-7.2 to remove Tris; 2). ProCAs were mixed with PEG-NHS ester in a molar ratio of 1:3 and then incubated at room temperature for 4 h or 4° C. overnight; 3). Unreacted free PEG-NHS were quenched by adding 100 mM Tris/HCl with a final concentration of 10 mM; 4) PEGylated ProCAs were further purified by HP Q column. After removing unbound proteins with 3 bed volumes of 10 mM HEPES at pH 8.0, the column was eluted with a 0-1 M NaCl gradient in 10 mM HEPES at pH 8.0. The PEGylation procedures were monitored by SDS-PAGE with protein staining by Coomassie brilliant blue and PEG staining with iodine.

Example 4

ProCA3 Variants

The ProCA3 variants (as shown in FIG. 1 and Table 1, for example) can comprise two gadolinium ions [$Gd^+$] embedded in alpha-helical and loop structures.

TABLE 1

Protein Contrast Agents of the Disclosure

| SEQ ID No. | Protein Scaffold | Ligand | Target | Position of target ligand in scaffold | Alternative Designation |
|---|---|---|---|---|---|
| 1 | ProCA1 (CD2) | GRP | GRPR | Internal | ProCA1.G10 |
| 2 | " | " | " | " | |
| 3 | " | Bombesin | " | " | ProCA1.B14 |
| 4 | " | " | " | " | ProCA1.B10 |
| 5 | " | PSMA Targeting peptide | PSMA | " | ProCA.PMSA |
| 6 | " | PSMA Targeting peptide | " | " | ProCA.PMSA |
| 7 | " | PSMA Targeting peptide | " | " | ProCA.PMSA |
| 8 | " | PSMA Targeting peptide | " | " | ProCA.PMSA |
| 9 | " | PSMA Targeting peptide | " | " | ProCA.PMSA |
| 10 | " | RGD | Integrin | " | ProCA1.RGD |
| 11 | " | CXCR-4 targeting peptide | CXCR-4 | " | |
| 12 | " | VEGFR targeting peptide | VEGFR | " | |
| 13 | ProCA1 (humCD2) | CXCR-4 targeting peptide | CXCR-4 | " | |
| 14 | " | VEGFR targeting peptide | VEGFR | " | |
| 15 | ProCA1 (ratCD2) | EGFR affibody | EGFR | C-terminus | |
| 16 | ProCA1 (humanized rat CD2) | Herceptin affibody | | " | |
| 17 | ProCA1 (humanized rat CD2) | EGFR affibody | EGFR | " | |
| 18 | ProCA3 (parvalbumin) | — | — | — | ProCA32 |
| 19 | ProCA3 (parvalbumin) | — | — | — | |
| 20 | ProCA3 (parvalbumin) | — | — | — | ProCA37 |
| 21 | ProCA3 (parvalbumin) | CXCR-4 targeting peptide | CXCR-4 | C-terminus | ProCA32.CXRC4 |
| 22 | ProCA3 (parvalbumin) | VEGFR targeting peptide | VEGFR | C-terminus | ProCA32.VEGFR |

There are six alpha-helix in ProCA3 variants. Metals such as, but not limited to, $Gd^{3+}$, $Eu^{3+}$, $Tm^{3+}$, $Yb^{3+}$, $Lu^{3+}$, $Mn^{2+}$, and $Fe^{3+}$ are chelated by more than six (6) oxygen ligand from amino acid. $Gd^{3+}$ binding sites in protein are located in the helix-loop-helix region of scaffold polypeptide. PEG is covalently linked to the scaffold polypeptide to improve the biological properties of the protein. At least one oxygen from water directly interacts with metal. The protein-based MRI contrast agents of the disclosure are formed by at least one metal ion, scaffold polypeptide with oxygen ligand from scaffold polypeptide and water as ligand bind to $Gd^{3+}$. The ProCA3 variants have a molecular weight from 11 kDa to 30 kDa.

ProCA3 can be further fused with a biomarker targeting peptide at N-terminal or C-terminal, and which can selectively bind to tumor-specific biomarkers expressed on the surface of the tumor cell. Exemplary biomarkers include, but are not limited to, such as EGFR, HER-2, VEGFR, CXCR4. These contrast agents can specifically enhance the tumor in MRI and CT.

Example 5

ProCA1 Variants

ProCA1 variants are formed by one metal ion such as, but not limited to, $Gd^{3+}$, $Eu^{3+}$, $Tm^{3+}$, $Yb^{3+}$, $Lu^{3+}$, $Mn^{2+}$, and $Fe^{3+}$ embedded in a beta-sheet protein. The metal ion is chelated by more than five (5) oxygen ligand from amino acid. PEG can be covalently linked to the scaffold polypeptide to improve the biological properties of the protein. Tumor targeting sequences can be grafted in the middle of ProCA1. ProCA1 variants have a molecular weight from 11 kDa to 30 kDa.

ProCA1 variants can be further fused with a biomarker target-specific peptide at the N-terminal or C-terminal, and which can selectively bind to tumor-specific biomarkers expressed on the surface of the tumor cell. Exemplary biomarkers include, but are not limited to, such as EGFR, HER-2, VEGFR, CXCR4. These contrast agents can specifically enhance the tumor in MRI.

Example 6

ProCA2 Variants

The ProCA2 variants are formed by two to four gadolinium embedded in alpha-helical and loop structures. There are six alpha-helix in ProCA3 variants. The metals, such as $Gd^{3+}$, $Eu^{3+}$, $Tm^{3+}$, $Yb^{3+}$, $Lu^{3+}$, $Mn^{2+}$, and $Fe^{3+}$, are chelated by more than six (6) oxygen ligands from amino acid. PEG can be covalently linked to the scaffold polypeptide to improve the biological properties of the protein. At least one oxygen from water directly interacts with metal. The protein based MRI contrast agents are formed by at least one metal ion, scaffold polypeptide with oxygen ligand from scaffold polypeptide and water as ligand bind to $Gd^{3+}$. ProCA2 variants have a molecular weight from 11 kDa to 30 kDa. ProCA2 variants can be further fused with biomarker targeting peptide as ligand at N-terminal, C-terminal or in the middle, which can specially bind to tumor biomarkers expressed on the surface of the tumor cell. These biomarkers include EGFR, HER-2, VEGFR, CXCR4. These contrast agents can specifically enhance the tumor in MRI and CT.

Example 7

Detection of Liver Metastasis by ProCA

Noninvasively early detection of cancer metastasis is essential for tumor diagnostics and treatment. MRI, embraced with high resolution, no depth limitation and three dimensional features, and exquisite soft tissue contrast without using ionizing radiation. However, the major barriers limiting the application of MRI to detect small liver lesions and metastasis with a size of smaller than 2 cm at the early stage, are due to the lack of desired MRI contrast agents capable of enhancing the contrast between normal liver tissues and tumors with high relaxivity with proper liver distribution and retention time. To overcome such limitations of low sensitivity associated to low relaxivity of the current clinically approved contrast agents, we have designed a novel class of protein MRI contrast agents (ProCA3) with multiple metal binding sites tailed to $Gd^{3+}$ binding and addition of a PEGylated hydration shell. ProCA3 exhibits $Gd^{3+}$ binding affinity (Kd Gd=2.8±0.3× $10^{-22}$ M) and metal selectivities over physiological metal ions $Ca^{2+}$ and $Mg^{2+}$ and $Zn^{2+}$ that are several order greater than that of current clinically available contrast agent DTPA. In addition, with significant improvement of both r1 and r2 relaxivities (r1=57 mM-1s-1 per Gd and 114 mM-1s-1 per particle, r2=80 mM-1s-1 per Gd and 160 mM-1s-1 per particle), ProCA3 is able to detect at least 2 μM in vitro and 0.8 μmol/kg that is greater than 100 fold increase in in vivo dose efficiency. ProCA3 has a good liver preference (60%) and retention time with a half-life about 2.8 hours, which permits to acquire high quality of MRI as well as high accuracy provided with both T1- and T2-weighted contrast imaging in a single injection. ProCA3 enables the first MRI detection of uveal melanoma micrometastatic liver tumor size down to about 0.16 mm revealed by histologic analysis. The unprecedented capability of ProCA3 in extending current detection of stage 3 to earlier metastatic liver tumor is expected to fill in a major gap in current clinically available MRI applications to enable non-invasive and early detection of primary liver tumors and metastases, the treatment effect by targeted therapy, as well as image-guided treatment and drug delivery.

Cancer formation of metastatic tumors in distant organs such as the lungs, liver, brain and bone is the main cause of nearly all human cancer-related deaths[8]. Liver is a common site for various cancer metastases including melanoma, breast, pancreatic, and colon cancers. Liver is also one of the major organs with high chance of formation of primary tumor in the developing countries. Liver failure from these metastases results in death. Uveal melanoma, the most common primary intraocular tumor, has an associated 40% risk of metastasizing to the liver within 10 years of diagnosis of the primary tumor. Hepatic metastases, which occur in 95% of patients with metastatic uveal melanoma, result in death in almost all cases. This high death rate is related to the recognition of liver metastasis at a very late stage (greater than 2.0 cm) in which the metastatic uveal melanoma is resistant to currently available systemic chemotherapies. Local treatment such as laser ablation is also limited by our capability in delineation of tumor lesions by non-invasive methods. Currently, there is no suitable non-invasive method for current clinically available detection of early small liver metastasis with desired sensitivity and selectivity.

Among the four current clinically available technologies that can effectively perform imaging across all parts of the human body, MRI is the most capable of creating high resolution 3D imaging and exquisite soft tissue contrast without using ionizing radiation[19-22]. It also allows for non-invasive, comprehensive, and repetitive assessment of biological and treatment processes of the same living animal and human at different points with anatomic and dynamic 3D information. In principle, the resolution of the current clinically available MRI scanner can reach 20 μm or better. However, clinically available MRI has the capability to detect tumor lesions only if the tumor is greater than about 1.8 cm. While MRI was strongly suggested for the routine follow-up of high-risk primary uveal melanoma patients, to date, MRI can only detect tumor sizes corresponding to the late stage of metastatic tumor due to the limitation of MRI contrast agents.

Gadolinium compounds are the most frequently used MRI contrast agents due to high paramagnetic property and asymmetric electronic ground state of $Gd^{3+}$, rendering the ability to create bright MR images by decreasing T1 without causing substantial line broadening. Current clinically available MRI contrast agents, such as Gd-DTPA, have relaxivities less than 5 $mM^{-1}$ $s^{-1}$ which require high injection doses of 0.025-0.2 mmol/kg to generate a detectable contrast with a local $Gd^{3+}$ concentration of about 100 μM. This is significantly lower than theoretic value of about 100 $mM^{-1}s^{-1}$ for one water molecule coordinated in the $Gd^{3+}$ inner shell. Patients with renal dysfunctions are also subject to a risk of nephrogenic systemic fibrosis (NSF) due to metal toxicity.

There are additional challenges for developing contrast agents for liver imaging due to its fast circulation. Gd-EOB-DTPA (Evoist US; Primovist, Europe, Bayer) and Gd-BOPTA (Multihance, Bracco) with 50% and 5% hepatocyte up take, respectively, are the most commonly used current clinically available approved as liver contrast agents. In addition to similar per Gd relaxivity ($r_1$) values around 4-6 $mM^{-1}s^{-1}$, and their very short retention time in the liver (1 min for Multihance and 30 min for Eovist) largely restrains a narrow time widow to achieve high quality MR imaging and limited time for MRI-guided liver intervention and local treatment. On the other hand, iron oxide nanoparticle contrast agents such as Ferumoxides are taken up by functioning Kupffer's cells creating T2/T2* effects on the normal liver, however it is less applicable due to imaging artifacts. Therefore, there is an urgent need to develop contrast agents with significantly improved relaxivity and metal stability, pharmacokinetics to enable the detection capability of smaller size tumor extending to less than 1 cm with good confidence.

The disclosure, therefore, encompasses protein-based MRI contrast agents with multiple metal binding sites decorated with a hydration water shell. They have strong $Gd^{3+}$ binding affinity that is comparable to current clinically available approved ones. In addition, they exhibit several order greater metal selectivity for Gd over physiological metal ions. These developed contrast agents with significantly improved relaxivity in both r1 and r2 values have unprecedented capability to enhance the detection limit both in vitro and in vivo several order of magnitude. With further improved liver retention time, it is possible to detect uveal melanoma in with a size less than 0.16 mm confirmed by histological analysis.

The ProCA3 variants can be formed by two gadolinium embedded in alpha-helical and loop structures. There are six alpha-helix in ProCA3 variants. The metals, such as $Gd^{3+}$, $Eu^{3+}$, $Tm^{3+}$, $Yb^{3+}$, $Lu^{3+}$, $Mn^{2+}$, $Fe^{3+}$, are chelated by more than 6 oxygen ligand from amino acid. $Gd^{3+}$ binding sites in these proteins are located in the helix-loop-helix region of the scaffold polypeptide. PEG is covalently linked to the scaffold polypeptide to improve the biological properties of the protein. At least one oxygen from water directly interacts with metal. The protein based MRI contrast agents are formed by at least one metal ion, scaffold polypeptide with oxygen ligand from scaffold polypeptide and water as ligand bind to $Gd^{3+}$. ProCA3 variants have a molecular weight from 11 kDa to 30 kDa.

ProCA3 can be further fused with biomarker targeting peptide moiety as ligand at N-terminal or C-terminal, which can specially bind to tumor biomarkers expressed on the surface of the tumor cell. At least one oxygen from water directly interacts with $Gd^{3+}$. The protein based MRI contrast agents are formed by metal ions, such as $Gd^{3+}$, $Eu^{3+}$, $Tm^{3+}$, $Yb^{3+}$, $Lu^{3+}$, $Mn^{2+}$, $Fe^{3+}$, and a scaffold polypeptide with oxygen ligand from scaffold polypeptide and water as ligand bind to Gd3+. The biomarkers include, but not limited to, EGFR, HER-2, VEGFR, CXCR4. These contrast agents can specifically enhance the tumor in MRI and CT.

ProCA32 has High $Gd^{3+}$ Stability and Metal Selectivity

To test our hypothesis and screening ProCA candidates with highest thermodynamic stability, $Gd^{3+}$ binding affinity and metal selectivity of ProCAs were measured by metal-chelator buffer system. ProCA3 variants were purified using Henzl's method with large modification. The UV absorbance of ProCA3 variants shows the similar pattern as reported in the literature. The $Tb^{3+}$-binding affinity of calcium-binding protein was measured by $Tb^{3+}$-chelator buffer system. Free metal concentration was carefully controlled by the ratio of metal with chelators from 0 to 1. After measured the $K_d$ of $Tb^{3+}$, the $K_d$ of $Gd^{3+}$ to ProCA is measured by $Gd^{3+}$ competition methods. The wild type calcium-binding protein binds to $Gd^{3+}$ with high affinity ($K_d$=6.4×10$^{-11}$ M), which is higher than the reported EF-hand proteins and comparable with our first generation of ProCA (ProCA1) designed on CD2. To better understanding the properties of our contrast agents, we introduce a tryptophan residue into the ProCA3. As shown from table II, introducing of fluorescence probe (F103W) to calcium-binding protein does not change $Gd^{3+}$ and $Tb^{3+}$ binding affinity of calcium-binding protein. Interestingly, ProCA32, a calcium-binding protein variant with PROCA32 mutation, exhibits 10$^{11}$ folds higher $Tb^{3+}$ and $Gd^{3+}$ binding affinity compared with wild type, which indicated that a negative charged side chain in position 5 is essential for strong binding of $Gd^{3+}$ by EF-protein. Fura-2 binds to $Gd^{3+}$ with a $K_d$ of 10$^{-16}$ M. The binding of $Gd^{3+}$ induce the fluorescence wavelength shift from 380 nm to 340 nm. To further compare the $Gd^{3+}$ binding affinity between ProCA32 and $Gd^{3+}$, we added different concentration of ProCA32 or wild type calmodulin in $Gd^{3+}$ loaded Fura-2 (20 μM). After adding 10 μM of ProCA32, The fura-2 fluorescence shift to 280 nm, which indicate that all the $Gd^{3+}$ is competed out from fura-2, and ProCA32 has much stronger $Gd^{3+}$ binding affinity than that of Fura-2. As control experiments, adding calmodulin with a concentration up to 20 μM does not shift the wavelength of Fura-2, and only a slight decrease of fluorescence intensity at 340 nm was observed. This results indicate that Calmodulin can compete $Gd^{3+}$ out of Fura-2, and CaM should have a much week $K_d$ than that of Fura-2. We also did Fura-2 competition assay by adding the same concentration of ProCA30, ProCA33, ProCA34 and ProCA35, the results is similar to calmodulin, indicating that ProCA3 variants, except ProCA32, has weak $Gd^{3+}$ affinity than that of Fura-2. ProCA32 has D, D, D, E, E in position 1, 3, 5, 9, 12 of EF-hand 1. Thus, D, D, D, E, E in position 1, 3, 5, 9, 12 of EF-hand is the optimized key residues to achieve high $Gd^{3+}$ binding affinity.

We further assessed the thermodynamic stability constant of physiological metals ions to our contrast agents. The $Ca^{2+}$ binding affinity of calcium-binding protein variants were measured by $Ca^{2+}$-EGTA buffer system, the dissociation constant of calcium-binding protein WT to $Ca^{2+}$ can reach to 10$^{-9}$ M, which is consistent with reported value measured by ITC and Ca flow dialysis. The $Ca^{2+}$ binding affinity of other variants were also around 10$^{-9}$ M. Similar to $Ca^{2+}$-EGTA buffer system[27], we used $Mg^{2+}$-EGTA buffer system to determine the $Mg^{2+}$ binding affinity to ProCA3 variants. ProCA30 and ProCA31 have similar $K_d$ to $Mg^{2+}$ about 2×10$^{-5}$ M. Interestingly, ProCA32 has 10 times stronger Kd to $Mg^{2+}$ than that of ProCA31 and ProCA32. Such dramatic increase of $K_d$ to $Mg^{2+}$ of ProCA32 may be cause by one more negative charged residue in EF-hand I of ProCA32.

$Zn^{2+}$ is an anther physiological metal ion contributes to the dissociation of $Gd^{3+}$ from current clinically available MRI contrast agents. Current clinically available MRI contrast agents usually have poor metal selectivity between $Gd^{3+}$ and $Zn^{2+}$. For example, Zn-DTPA has a thermodynamic stability of 5.13×10$^{-19}$ M, and the selectivity of $Zn^{2+}$ over $Gd^{3+}$ is 4.17. (Yang JACS) To further evaluate the $Gd^{3+}$ selectivity over $Zn^{2+}$ of ProCA3 variants, the binding affinity of ProCA3 of $Zn^{2+}$ was measured by Fluozin-1 competition method[26]. As shown from Table II, the $Zn^{2+}$ binding affinity for calcium-binding protein WT (ProCA30) is 2.05× 10$^{-6}$ M, and the binding affinity of $Zn^{2+}$ to ProCA32 is 6.0×10$^{-8}$ M. The $Gd^{3+}$ selectivity over $Zn^{2+}$ is 13.1, which is about 3 times higher than that of DTPA. These results indicate that addition of negative charged ligand to the metal binding pocket (S56D) has ambient increase the binding affinity of $Zn^{2+}$ compared with that of $Gd^{3+}$. These results are constant with literature that oxygen is not a preferred ligand for $Zn^{2+}$. Since oxygen is not a preferable ligand for $Zn^{2+}$ but a preferable ligand for $Gd^{3+}$, our designed ProCA can overcome $Gd^{3+}$ release of MRI contrast agents due to $Zn^{2+}$ competition.

Among our design protein contrast agent candidate, only one protein, ProCA32, shows desired metal selectivity. Metal selectivity in PROCA32 mutant dramatically increase $Gd^{3+}$ selectivity over physiological metal ions ($Zn^{2+}$, $Ca^{2+}$ and $Mg^{2+}$), compared with WT and other mutations, and this huge increase of $Gd^{3+}$ selectivity is mostly contributed by the dramatic increase of $Gd^{3+}$ binding affinity in position 5 of EF-hand I.

$Gd^{3+}$ binding affinity and metal selectivity increased in PROCA32 mutant. The water coordination number of $Tb^{3+}$ in ProCA was measured by $Tb^{3+}$ luminescence lifetime experiments. The determined water number for calcium-binding protein WT is 1.3, which is consistent with reported value[31]. Interestingly, water coordination number in PROCA32 is 0.44, which is much smaller than that of WT and other calcium-binding protein variants. This result indicate that the original water ligands were replaced by additional side chain ligand due to PROCA32 and the dramatic increase of $Tb^{3+}$ and $Gd^{3+}$ binding affinity is caused by the additional ligand binding from side chain of PROCA32. Since $Gd^{3+}$ can use two oxygen ligands from bidentate carboxylate ligand side chain of Asp or Glu, it is highly likely Asp56 in PROCA32 provide two oxygen ligand to interact with $Gd^{3+}$, while the original Ser56 only provide one oxygen ligand to interact with $Tb^{3+}$ and $Gd^{3+}$. On the other hand, mutation E60D or S56DE60D has increased water number indicating that side chain carboxyl group in E60D mutant is replaced by water as $Gd^{3+}$ binding ligand.

ProCA32 and PEGylated ProCA32 has High Serum Stability

It is extremely important that the ProCA3 are not cleaved by the enzyme in the serum and maintain intact structure before secreted out of the body. To evaluate the stability of ProCA32, ProCA32 were incubated in the 50% serum and then detected by SDS-PAGE and Mass spectrum. ProCA32 were very stable in the serum for at least 3 days. After three days, the proteins in the serum are degreed, but ProCA32 still existed in the blood serum even after 12 days. Immunoblot and Mass spectrum are also applied to detect the serum stability of ProCA32 and ProCA32-PEG. All of these data shows that ProCA32 is stable in serum of at least three days. ProCA32 has an excretion half liver around 2.8 hours and clearance about 0.13 l/kg in mice, such high stability of ProCA32 is essential for the safety profile of ProCA32.

High r1 and r2 Relaxivity of ProCA3 Variants

We next studied the longitudinal and transverse relaxivity of ProCA3 variants. The relaxivity of ProCA3s are measured in mini-spec (Brucker) at 60 MHz at 37° C. Our contrast agents present at least 10 folds increase in the both $r_1$ and $r_2$ than that of Gd-DTPA (FIG. 3). ProCA32 which shows most excellent stability has per Gd $r_1$ of 30 $mmol^{-1}$ $s^{-1}$ and $r_2$ of 40 $mmol^{-1}$ $s^{-1}$. ProCA32 has two $Gd^{3+}$ binding sites, and the per particle relaxivities are $r_1$ of 60 $mmol^{-1}$ $s^{-1}$ and $r_2$ of 80 $mmol^{-1}s^{-1}$. This is a great achievement because all the current clinically available MRI contrast agents, except MS-325, only yields $r_1$ of 3.5 and $r_2$ of 5 $mmol^{-1}s^{-1}$ at same magnetic field and same temperature. High relaxivity of ProCA32 also suggest that the detection limit of MRI contrast agents can be pushed from 20 μM to 1 μM when the $r_1$ relaxivity increase from 3.5 $mmol^{-1}s^{-1}$ to 60 $mmol^{-1}s^{-1}$ [33].

PEGylation improves the in vivo properties of protein drugs. To further optimize the pharmacokinetics of ProCA32, we covalently linked PEG40 (Thermo) to ProCA32, named ProCA32-P40. No change of $Gd^{3+}$ binding affinity, selectivity and relaxivity differences were found by above test.

Interestingly, the per $r_1$ and $r_2$ of ProCA35 (S56DE60D) further increase to 57 and 77 $mmol^{-1}$ $s^{-1}$, respectively. The increase of the relaxivities is consistent with the increase of water number in this mutant. These data indicate that the relaxivities increase of S56DE60D is cause by increase water number and the relaxivities of ProCA3 can be tuned by changing ligand types and the local $Gd^{3+}$ binding pocket. We didn't further study in vivo properties of ProCA35 because low $Gd^{3+}$ binding affinity and selectivity.

ProCA3 Variants have High $r_1$ Relaxivity at High Magnetic Field

With the development of high field MRI scanner, there is a strong need to develop the contrast agents with high relaxivity in high magnetic field strength. However, the relaxivity of macromolecular contrast agents always has dramatic drop at high magnetic field. Caravan and Luther point out the contrast agents with optimized relaxivity in high field should have a rotation correlation time ($\tau_R$) around 2 ns. We tested our Gd-calcium-binding protein variants in 7 T Varian MRI scanner using inversion recovery sequence. The relaxivity for ProCA32 is 18 $mM^{-1}$ $s^{-1}$, which is more than 3 times higher than that of DTPA, and reaches the theoretical up limits of the per Gd $r_1$ of $Gd^{3+}$ at 7 T (about 20 $mM^{-1}s^{-1}$). Other ProCA3s also have a per Gd $r_1$ relaxivity around 20 $mM^{-1}s^{-1}$ at 7 T and room temperature. These results suggest that ProCA3 has high relaxivity even in the high magnetic field which open new avenue for the development of MRI contrast agents applied in the high magnetic field.

ProCA32 is Much Sensitive than Current Clinically Available MRI Contrast Agents

Less contrast agents are acquired to acquired good image enhancement when the relaxivity of the contrast agent improved. Since our contrast agents show about 10 times higher relaxivity at 1.47 T and 3 times higher relaxivity at 7 T compared with that of Gd-DTPA, we further studied the detection limits in vitro and in vivo. To test the in vitro detection limits, ProCA3 with different concentration were scanned using T1-weighted spin echo sequence at 7 T. As shown from FIG. 4 A, 2.5 μM of ProCA3 showed much higher signal intensity compared with buffer only. This result indicates the detection limits for ProCA3 is at least 2.5 μM, which is more than 10 times sensitive than that of current clinically available MRI contrast agents. We further test the in vivo detection limits for the detection of kidney enhancement by injection of a serious concentration of ProCA3 in different mice. A clear kidney enhancement as obtained with an injection dosage of 0.8 μmol/kg ProCA32, a concentration more than 100 times lower than the current clinically available injection of Gd-DTPA. Interestingly, injection of 1.6 μmol/kg Gd-DTPA, same $Gd^{3+}$ concentration as 0.8 μmol/kg of ProCA32-P40, do not show any significant kidney enhancement under MRI. These results indicate that ProCA32 has much lower detection limits than Gd-DTPA in vitro and in vivo.

ProCA32 and ProCA32-P40 has No Toxicity

To evaluate the cytotoxicity of the ProCA3, H441 and PC3 cells precultured on 96 well plates are incubated with 30 or 50 μM Gd-DTPA and ProCA32. The cell variability after incubation overnight were tested by MTT assay. No significant differences are observed between untreated group and the groups incubated with ProCA3 without $Gd^{3+}$, ProCA3 with two $Gd^{3+}$, which indicate that ProCA32 is not toxic for H441 and PC3 cells. Our unpublished data show that ProCA3 also has no toxicity to human bone marrow cells.

The acute toxicity of ProCA32 to CD1 mice are analyzed with the injection of 0.012 mmol/kg ProCA32. The bloods of the mice are collected two days post injection. The blood from CD1 mice without any injection of contrast agents were used as control. There is no significant difference between control group and group injected with ProCA32 on creatine, ALT, ALP, cholesterol, glucose, triglycerol level, which indicate that the kidney, liver, heart function are not influenced by ProCA32. The albumin and total protein, total bile, $K^+$, $Na^+$, $Ca^{2+}$, and $Cl^-$ level are at the same level as the control mice. All these data indicates that ProCA32 has low chronic toxicity.

ProCA32-P40 has Excellent Pharmacokinetics and Long Toxicity

To understand the blood retention, distribution and clearance of ProCA32-P40, we did pharmacokinetics study of ProCA32-P40. the $Gd^{3+}$ concentration in the plasma of mice at different time points after injection of ProCA32-P40, $GdCl_3$ or Gd-DTPA. ProCA32-P40 has much longer blood retention time than that of $GdCl_3$ and Gd-DTPA. ProCA32-

P40 has a distribution half-life of 0.15 hour and elimination half-life of 2.9 hours. The volume distribution of ProCA32-P40 is 0.13 l/kg indicating that ProCA32-P40 mainly distributed in the blood and extracellular extravascular spaces. Thus, ProCA32-P40 has good pharmacokinetics for MRI.

To understand the organ distribution and clearance of ProCA32-P40 in mice, $Gd^{3+}$ concentration in different organs were measured by ICP-OES 10 minutes post i.v. injection of $GdCl_3$, Gd-DTPA or ProCA32-P40 in mice. $GdCl_3$ is mainly distributed in the lung and spleen after 10 post injection, while ProCA3 is mainly distributed blood, liver and kidney. Due to fast clearance, Gd-DTPA mainly accumulated in kidney.

Gadolinium release and accumulation is believed to induce NSF. To further study the long term accumulation and clearance of ProCA32-P40. $Gd^{3+}$ concentration in different organs were measured by ICP-OES 14 days post i.v injection of $GdCl_3$, Gd-DTPA or ProCA32-P40 (0.0033 mmol/kg ProCA32-P40, 0.0067 mmol/kg GdCl3 or 0.2 mmol/kg Gd-DTPA) in mice. Gadolinium from $GdCl_3$ has much higher accumulation in bone, liver and spleen, which are the major organs for the Gadolinium deposit. ProCA32-P40 has lowest accumulation in liver, lung, and spleen among these three reagents. Thus, ProCA32-P40 has lower long-term $Gd^{3+}$ accumulation compared with GdCl3 and the current clinically available injection dosage of Gd-DTPA. ProCA32 can Image Uveal Melanoma Metastasis in Liver with a Size Less than 0.25 mm in Mice Model with High Confidence.

Liver is one the major organ for the tumor metastasis, such as melanoma, breast cancer and pancreatic cancer. Early detection of primary and metastatic tumor in the tumor is essential for better treatment of tumor. 50% of the uveal melanoma metastasis to the liver and 90% of the patient dead after with metastatic tumor size between 0.5 mm to several centimeters. Less effective treatment can be done since the metastatic melanoma is too small to be detected by imaging modalities such as PET, MRI and ultrasound, and current detection limit of the liver metastatic tumor by MRI is around 20 mm with high confidence. Early detection tumor with a size less than 1 mm can be of great significance because prompt and suitable treatment of the disease can be applied if tumor can be detected earlier. Our data indicate that ProCA32-P40 is able to image liver with high intensity than Eovist and significantly change liver intensities using both $T_1$- and $T_2$-weighted sequences. Thus, we hypothesis ProCA32-P40 can detect tumor metastases in liver with much smaller size. The mice melanoma cells were implanted in the eye of the PEDF knockout mice. The tumor implanted mice were continuously grown for two weeks.

We then imaged the mice liver under MRI with $T_2$-weighted fast spin echo and $T_1$-weighted spin echo sequence. The mice were imaged before and injection of the contrast agents. Liver metastasis of melanoma cannot be detected without injection of the contrast agents neither in $T_1$-weighted nor $T_2$-weighted MR images. After injection of ProCA32-P40, We clearly see more than 10 liver metastasis in the mice liver with hypo-intensity of tumor in $T_1$ weighted spin echo and hyper-intensity of tumor in $T_2$ weighted fast spin echo sequence. Interestingly, the MR imaging of liver metastasis correlates well with HE staining, where the tumor in dark blue/purple color and normal liver is pink color. The location of the tumor under MRI were further confirmed by IHC staining of S100, which is a typical biomarker for melanoma. To further explore the mechanism of hypo-intensity of tumor under MRI, the optical and fluorescent images of mice liver with melanoma metastasis were taken by fluorescent dissecting microscope 30 min post I.V. injection of fluorescein-labeled ProCA32-P40. The liver tissue showed enhanced green fluorescence, while melanoma metastases does not show any fluorescence. These results indicate that after injection for 30 min, ProCA32-P40 is accumulated in liver tissue, while no ProCA32-P40 can be penetrated in to the melanoma due to lack of blood vessel and lower contrast agents permeability. Moreover, we are able to clearly detect liver metastasis with a size less than 0.25 mm under both $T_1$-weighted and $T_2$-weighted MR images. The ability of tumor detection using two dramatically different imaging modalities enable us to detect small tumors with high confidence. In contrast, most of current MRI test can only detect tumor with a size more than 20 mm with high accuracy. As a comparison experiment, we also try to image the tumor metastasis in the same mice model using Evoist. No tumor can be detected from either T1-weighted or T2-weighted MR images. Thus, ProCA32-P40 shows the great advantages for the imaging tumor metastasis in liver and ProCA32-P40 show great potential for the early diagnostics of liver metastasis. Early diagnosis of liver metastases is essential for the effective drug treatment of tumor.

Protein-based MRI contrast agents (ProCA) opened up a new avenue for the exploration of novel MRI contrast agents with high relaxivities. ProCA1, previously named CA1.CD2, has more than twenty folds higher relaxivity compared with that of Gd-DTPA at current clinically available magnetic field. Targeted ProCA1s, ProCA1.GRP(52) and ProCA1.affibody, are able to image cancer biomarker expression in mice model. Furthermore, the relaxivity, stability, biodistribution and immunogenicity can be further optimized by PEGylation. One of the limitation of ProCA1 is relatively low $Gd^{3+}$ binding affinity ($K_d=8.7\times10^{-13}$M), which is much lower than current clinically available MRI contrast agents ($10^{-21}$M for DTPA and $10^{-17}$M for DTPA-BMA), even though the metal selectivity between $Gd^{3+}$ and $Ca^{2+}/Zn^{2+}$ is better than DTPA-BMA and Gd-DTPA[26]. The low $Gd^{3+}$ binding affinity of ProCA1 variants hampers its application for the current clinically available application. On the other hand, even though peptide from EF-hand of CaM are used to chelate $Gd^{3+}$, peptide based MRI contrast agents is limited by low relaxivity, low $Gd^{3+}$ stability and low stability for enzyme cleavage. In the current study, we development a novel MRI contrast agents using completely different strategies. We carefully studied the metal binding geometry of $Gd^{3+}$ and other lanthanide, and then engineered naturally existed $Ca^{2+}$ binding protein as a MRI contrast agents with comparable $Gd^{3+}$ stability as current clinically available MRI contrast agents and much desired metal selectivity.

$Tb^{3+}$ luminescent life time decay in $H_2O$ and $D_2O$ solvents is measured to characterize the water coordination number of the inner sphere of metal binding sites. WT calcium-binding protein has averaged water number of 1.3, which is consistent with reported value. Interestingly, the water number of ProCA35 increases to 1.6, the increase of water number in ProCA35 is consistent with the increase of relaxivity in ProCA35. To our surprise, the water number of ProCA32 decrease from 1.2 to 0.4, while the relaxivity of ProCA32 does not decrease. All these results indicate that increase mutation of PROCA32 introduce more ligands from protein to interact with $Gd^{3+}$, which increase $Gd^{3+}$ binding affinity and decrease the number of water to interact with protein. The per $Gd^{3+}$ and per particle relaxivity of ProCA32 does not decrease compared with calcium-binding protein WT, which indicates other phenomena, such as water exchange rate or secondary or outersphere relaxivity plays an important role one the high relaxivity of ProCA32.

In this study, the relaxivity of ProCA3 variants can be modulated by careful protein design. Position 1, 3 5, 7, 9 and 12 in EF-hand is the key residues for metal binding. Among them, position 1, 3, 5 and 12 usually use side chain oxygen as metal ligand. Position 9 of EF-hand always bridged with one water molecular. Glutamate 60 is located in the position 9 in the EF-hand I of calcium-binding protein. X-ray structures of calcium-binding protein shows that Glutamate acid 60 directly interact with metals without water bridge, we hypothesis that mutation of E60D will introduce water ligand to position 9. Consistent with our hypothesis, the water number of S56DE60D increase to 1.8, while the WT calcium-binding protein only has a water number of 1.3. Interestingly, the per Gd relaxivity of ProCA35 (S56DE60DF103W) dramatically increase to r1=57 and r2=77 mM$^{-1}$s$^{-1}$, and pre particle relaxivity increase to 114 and 154 mM$^{-1}$s$^{-1}$, which is about 100% increase for both $r_1$ and $r_2$ comparing the ProCA30 (wild type CABP), ProCA31 (calcium-binding protein with F103W mutations) and ProCA32 (calcium-binding protein with PROCA32F103W mutations). This is the first report to clearly demonstrate the $r_1$ and $r_2$ relaxivities of protein-Gd$^{3+}$ complex can be tuned by the change of coordinated water molecular by site direct mutagenesis.

To develop a MRI contrast agent with high sensitivity, high relaxivity is higher desired. ProCA3 has more than 10 times higher $r_1$ relaxivity at current clinically available MRI field (1.4 T), which provide a more sensitive tool for the MR imaging for current clinically available and pre-current clinically available diagnostics. Furthermore, due to careful design, the $T_R$ of the ProCA3 variants were optimized for the use in the high magnetic field. The $r_1$ relaxivity of ProCA32 is 18 mM$^{-1}$s$^{-1}$, which reached the theoretical relaxivity value of Gd$^{3+}$ based MRI contrast agents. In contrast, most macromolecular MRI contrast agents has dramatic r1 relaxivity drop at high magnetic field due to undesired TR. The relaxivity of ProCA3 decrease at high temperature, which indicate that ProCA32-P40 also has optimized fast water exchange.

Only 2.5 µM of ProCA32 in the test tube can be detected, which is much lower dosage than that of Gd-DTPA. High relaxivity of ProCA3 at both current clinically available and high magnetic field will two advantages. First, increased the relaxivity improves the detection of MRI which will benefit the molecular imaging using MRI, since biomarkers always has limited expression levels and only can be detected by very sensitive probes. Second, increased relaxivity of ProCA3 can effective reduced the injection dosage, which could decrease the toxicity caused the metal release. The injection dosage for ProCA3 is 0.03 mmol/kg for the imaging of the blood pool, liver, kidney and liver metastasis. However, the in vivo detection limits of kidney can be further pushed to less than 0.0008 mmol/kg for kidney imaging and 0.0016 mmol/kg for the liver imaging. These results indeed indicated that ProCA32 can improve the detection limits and injection dosage for MRI.

Serum has different kinds of protease and Protein-MRI contrast agents must stable in vivo and resistance to the protease cleavage. We have analyzed the serum stability of ProCA32 and ProCA32-P40 by incubating the designed proteins that complex with Gd with mice serum at 37° C. at different length of time. The degradation of the protein was analyzed by both SDS-PAGE and MALDI mass spectrometry. The results showed that the protein remained intact for up to 72 hours in the presence of 50% human serum for 72 hours incubation. As an internal standard, albumin is cleaved and show lower band on the SDS-PAGE, while ProCA32 remains intact. These serum stability tests indicate that ProCA32 is resistant to protease the cleavage and is very stable in serum.

The toxicity of MRI contrast agents is mainly caused by free Gd$^{3+}$ release. Gd$^{3+}$ has a similar ionic radius as Ca$^{2+}$, thus, Gd$^{3+}$ can mimic Ca$^{2+}$ to interact with Ca$^{2+}$ binding proteins, such as Ca$^{2+}$-ATPase, channels, receptors and enzymes. Gd$^{3+}$ binding to the Ca$^{2+}$-binding proteins changes the activity or kinetic properties of the protein. for example, Gd$^{3+}$ can activate calcium-sensing receptor and induce inward Cl$^-$ current. Free Gd$^{3+}$ is toxic with a LD$_{50}$=0.1 mmol/kg in mice. NSF, a new merged disease in the patient with impaired rental function, is believed to be caused by the free Gd$^{3+}$ release after administration of Gd$^{3+}$-based MRI contrast agents. Therefore, a safe MRI contrast agent must have no Gd$^{3+}$ accumulation after injection. To further push protein-based MRI contrast agents for the current clinically available application, the toxicity, pharmacokinetics, biodistribution and excretion of these agents must be carefully studied. MTT assay in H441 cells shows that ProCA3 with and without Gd$^{3+}$ has no cytotoxicity. Our serum toxicity data shows that mice have normal liver, kidney, heart functions. The total protein concentration, albumin concentration, lipids concentration, Na$^+$, K$^+$, Ca$^{2+}$, and Cl$^-$ level in mice are also similar to the control group injected with saline. These data provide strong evidence that ProCA32 has no toxicity. The elimination half-life for ProCA32-P40 is 2.9 h and steady state volume distribution is 0.13 kg/l indicating that ProCA32-P40 is mainly distributed in the central organs such as liver, kidney and blood. ProCA32-P40 quickly excreted by with a clearance rate of 0.34 ml/min/kg.

Since ProCA32 has high $r_1$ and $r_2$ relaxivities and stability, it is promising to apply ProCA32 in vivo for the disease diagnosis. The PEGylation of ProCA32 (named ProCA32-P40) does change the Gd$^{3+}$ binding affinity, metal selectivity and selectivity. With 10 times lower injection dosage than that of current clinically available MRI contrast agents, ProCA32-P40 is able to image blood vessel, liver, kidney. The small blood vessels with a diameter of less than 1 mm are able to be clearly imaged; therefore, ProCA32 has great potential for MRA. Supported by both 3D gradient echo images and DCE-MRI, ProCA32 has much longer blood circulation time. Longer blood circulation of ProCA will benefit the MRI guided intervention therapy (ref), since such therapy usually performed for a very long time. Long blood circulation time of ProCA32 in blood also promising for the application of DCE-MRI. Arterial input function (AIF) in DCE-MRI experiment is the key experiment for successful calculating tumor permeability. However, it is hard to accurate determine AIF of current clinically available MRI contrast agents, since the blood circulation time of current clinically available MRI contrast agents is too short. ProCA32-P40 has longer blood circulation time, and AIF of ProCA32 is easily to be determined by both MRI and blood sampling. Thus, ProCA32-P40 will also have promising application on using DCE-MRI to probe tumor vasculature.

Liver is one the major organs for the tumor metastases, such as melanoma, breast cancer and pancreatic cancer. Early detection of primary and metastatic tumor in the liver is extremely essential for the early and effective cancer treatment. Liver metastases from uveal melanoma is a very server disease. 50% of the uveal melanoma metastasize to the liver and 90% of the patient die due to the lack of sensitive technique of early detection and lack of effective treatment when the metastatic melanoma has a size larger than 0.5 mm. More effective treatment can be done if the metastatic melanoma can be done if these tumors can be detected at early stage. However, current diagnostic methods such as PET, MRI and ultrasound, can only detect large tumors in the liver. The most sensitive technique for tumor detection is MRI with the injection of tumor specific MRI contrast agents, such as Eovist. Unfortunately, the current detection limit of the liver metastases by Eovist-enhanced MRI, diffusion MRI or T2 weighted MRI is around 20 mm with high confidence. In our study, we demonstrate that ProCA32-P40 has 50% higher signal MR signal intensity of liver in the T1-weighted MR images after injection of ProCA32-P40 compared with the same injection dosage of Eovist. In addition, ProCA32-P40 is able to efficiently decrease MR signal of liver the T2 weighted MR images, while Eovist does not cause such decrease. Due to the extremely small size and intrinsic properties of melanoma, no tumor can be visualized without injection of MRI contrast agents using $T_1$-, $T_2$- or diffusion weighted MRI sequences. Since ProCA32-P40 the low permeability of the tumor and high permeability to liver tissue, injection of ProCA32-P40 dramatically enhance the signal differences between tumor and liver tissue. Such differences can be used to detect tumor in both $T_1$-weighted and $T_2$-weighted MRI. The reason that Eovist fails to detect these tumor is mainly three reasons: 1) The r1 relaxivity of Eovist is low, which make the MRI signal differences between tumor and liver not so significant to be detected in $T_1$-weighted MRI sequences; 2) Using current clinically available injection dosage, Eovist do not have significant signal decrease in $T_2$-weighted MRI sequences and contrast enhanced $T_2$-weighted sequences cannot be used to further validate the tumor detected by T1-weighted images; 3) Since the tumor is too small, other MRI techniques without rely on the injection of MRI contrast agents, such as diffusion weighted MRI, is not sensitive to detect tumor and cannot be used as an alternative approach to validate the tumor from $T_1$-weighted MRI after injection of contrast agents. Therefore, ProCA32 is superior for the imaging of liver tumors with both $T_1$- and $T_2$-weighted sequences. ProCA32-P40 is in a better position for early detection of liver metastasis with much higher contrast to noise ratio, and with dual modality methods.

MRI contrast agents with high metal binding affinity, high relaxivity and low toxicity are highly desired for the preclinical and clinical study using MRI. Protein-based MRI contrast agents with high relaxivity, high metal selectivity, and high stability are required for current clinically available tests. In this paper, we reports our novel design of protein-based MRI contrast agents (ProCA3) by tuning metal binding sites from a native metal binding protein CABP. The extremely high $Gd^{3+}$ binding affinity ($K_{dGd}$=2.8±0.3×10$^{-22}$ M) is achieved by single mutation (S55D) on the metal binding sites. By increasing inner sphere water number from 1.2 to 1.5, the per $Gd^{3+}$ relaxivity of ProCA3 variants increase from 30 mM$^{-1}$s$^{-1}$ to 57 mM$^{-1}$s$^{-1}$. ProCA32-P40 present high stability, no cell toxicity and acute toxicity and proper blood circulation time for MRI of multiple organ tissues, such as liver, kidney and blood. ProCA32-P40 is able to detect liver metastasis with a size less than 0.6 mm with both $T_1$- and $T_2$-weighted MRI. This report opens a new avenue to understand the mechanism of $Gd^{3+}$ protein interaction, relaxivity, and molecular imaging, and it will also promote the early detection of liver metastases for better treatment.

Example 8

Application of ProCA in CBV

In cognitive and system-level neurosciences, functional magnetic resonance imaging (fMRI) is one of the main tools for noninvasively studying the brain activations associated with sensory stimulation and behavioral responses. FMRI is currently based on the blood-oxygen-level dependent (BOLD) contrast mechanism, which is an indirect measure of neural activity by way of hemodynamics and neurovascular coupling. Because of the limited temporal resolution and poorly understood neurovascular coupling of fMRI signals, the functional interpretation of BOLD signals is often complicated and unsettling. Multimodal recordings such as fMRI and EEG (electroencephalography), or fMRI and MEG (magnetoencephalography) often used to circumvent these problems are not also free of technical problems including ill-defined inverse EEG/MEG source solutions.

Magnetic resonance imaging (MRI) with high resolution three-dimensional maps of morphological features of the specimen has been an important tool for studying the brain. It is non-invasive, is not restricted by light scattering to those cells within a hundred microns of the surface and does not produce toxic photobleaching by-products, which are the major hurdles for optical microscopic methods. Because of these unique features and advantages, it has emerged as a powerful diagnostic technique in current clinically available settings and an indispensable tool in understanding brain behavior and neuron networks. For the last decade functional magnetic resonance imaging (fMRI) has rejuvenated the field of cognitive neuroscience by mapping spatiotemporal patterns of brain activity in human subjects. Blood-oxygenation-level dependent (BOLD) effect, based on a combination of changes in local blood oxygenation and flow and blood volume triggered by elevated neural activity, monitors hemodynamic changes. While BOLD effects offer a noninvasive readout of regional brain activity, the BOLD signal usually starts to rise within two seconds after onset of a sensory stimulus, which limits the use of the BOLD method to the specific response with spacing of capillaries in the brain (>50 um) and distinguishes components of activity originating from discrete cell populations such as excitatory vs. inhibitory cells, in a given brain area. During a brain activity following a sensory stimulation, a variety of changes occur, such as regional ionic concentrations, cerebral blood volume (CBV), and the glutamate responses.

CBV, defined as milliliters of blood per 100 ml of brain tissue, is an important indicator of brain function. The CBV-weighted fMRI including DSC-MRI and VASO-MRI has been playing an important role in understanding brain physiology and pathophysiology. Many disease conditions including brain tumors, Alzheimer's diseases, arteriovenous malformations and acute stroke are related to abnormal CBV values. For functional brain imaging, absolute CBV (aCBV) maps can provide important information about CBV abnormalities in a single subject. Absolute CBV, often obtained by the DSC-MRI approach, which uses a paramagnetic contrast agent (Gd-based complexes) given by i.v. route and applies a rapid image acquisition sequence to monitor the MR signal intensity during the first passage of the agent through the microvasculature. Relative CBV (rCBV) can also be obtained by VASO-MRI. It can provide maximal signal difference between pre- and post-contrast situations with advantages over a CBV measurement without requiring the measurement of the contrast agent concentration in the incoming arterial blood. Current measurement of CBV with both MRI techniques relies on the employment of small molecule based Gd-DTPA as a contrast agent. The accurate measurement of CBV is limited by low relaxivity and short vascular retention time. It is essential to develop MRI contrast agents with significantly higher relaxivity and longer vascular retention time by measuring CBV with both MRI techniques to detect brain responses at high resolution and accuracy.

The second change for brain and neural imaging is that the endogeneous contrast agent (blood-oxygen-level)-based fMRI lacks temporal resolution of electrophysiology. Mainly due to low relaxivity of contrast agents of current clinically available approved ones, it was concluded that it is impossible to apply MRI to monitor the biomarkers to monitor specific brain events due to limited numbers of the biomarkers in the brains.

Our protein-based contrast agent can be used to monitor brain function. To evaluate the safety and effectiveness of the contrast agents, we use flashing light simulation in anesthetized eyes-pen rats. In these experiments, we measure the CBV, the glutamate response, and the BOLD- and contrast-agents-based fMRI signals from their primary visual (V1) cortices. We evaluated the respective average V1 responses for a visual stimulation and compare these average responses.

Tumors can have abnormal blood vasculatures. The growth rate of the tumor is much faster than blood vessel, therefore, the rapid proliferation of tumor cells force blood vessel apart. The leakage size of the tumor vasculature various in different tumors, and it could be reached to more than 100 nm. Tumor and stromal cells also secret enzymes and growth factors to facilitate the formation of new blood vessel and rebuilt extracellular matrix. This process called angiogenesis. On the other hand, high interstitial fluid pressure in tumor forms a barrier for the penetration of drugs and imaging reagents from blood vessel to tumors.[63]

Dynamic-contrast enhanced MRI (DCE-MRI) is a non-invasive tool to probe tumor vasculature by mathematically modeling and calculating contrast accumulation in the tumor over time. The current clinically available MRI contrast agents, such as Gd-DTPA has been applied to evaluate the tumor vasculature of many types of cancers, such as breast cancer, pancreatic cancer.[1] This technique is very helpful to monitor the tumor vasculature changes of the patients after tumor treatment with angiogenesis drugs. DCE-MRI is also widely applied as an advanced technique in the preclinical field to evaluate the effects of angiogenesis drugs.[1] Due to the non-invasive properties, applications of DCE-MRI decrease the number of animals and cost in preclinical drug development.

Current DEC-MRI methods still have some limitations. First, to accurately calculate the blood volume and blood vessel permeability, most DCE-MRI methods require accurately measuring the arterial input function (AIF), the contrast agent concentration in the artery at different time points post injection. The AIF of current clinically available MRI contrast agent, however, is extremely difficult to be measured accurately due to their short blood half-lives and their fast excretion.[2] For example, the blood half-life for Gd-DTPA is only 2 min in mice and 10 min in human. It has a lot of technique difficulties to determine contrast agents in the blood very accurately in such a short time. Second, due to the small size and fast tumor penetration, DCE-MRI is not able to differentiate the leakage size using current clinically available MRI contrast agents. Third, current clinically available MRI contrast agents have short time accumulation and short time release in tumor, which restrict enough data collection in the limited time period.

Compared with current clinically available MRI contras agents, ProCAs has their own advantages for the DCE-MRI study: (1) the concentration of ProCAs in the blood is relatively stable, which made easier to measure AIF with small error; (2) ProCAs have much longer accumulation time in tumor, which simplified the mathematical model; (3) due to the larger size, ProCAs can only selective pass blood vessel with a leakage larger than ProCAs; and (4) ProCAs have higher relaxivity, which could improve the sensitivity and dose efficiency of contrast agents. Taken together, ProCAs are promising probes for the DCE-MRI of tumor blood vessel. Since DCE-MRI can also be applied to imaging other abnormal tissue, ProCAs can also be used for the DCD-MRI of other type of diseases, such as stroke and liver kidney.

Arterial Input Function Study of ProCA32

Since ProCA32 has high relaxivity and sensitivity at high magnetic field than of nanoparticles and small molecular MRI contrast agents. We measured the AIF differences of mice at 9.4 T Bruker MRI Scanner. Five baseline images without injection of contrast agents were collected before injection of MRI contrast agents. Then, 0.025 mmol/kg ProCA32 was injected in mice through tail vein. MR images were continuously collected by another 85 min. ProCA32 has very clear AIF. The blood vessel of the mice is enhanced for at least 85 min. On the other hand, Gd-DTPA only has very short AIF with a half-life less than 1 min. Due to such fast decrease of Gd-DTPA in blood vessel, it is extremely hard to collect AIF of Gd-DTPA correctly for DCE-MRI study. Thus, ProCA32 has a tremendous advantage for the evaluation of tumor vasculatures by DCE-MRI.

DCE-MRI of Kidney by ProCA32

We next compared the in vivo properties between ProCA32 and Gd-DTPA to probe blood vessel and kidney enhancement by DCE-MRI. To evaluate the dynamic enhancement of ProCA32, $T_1$ map of the same slice are collected by FESMS sequence with different length of TR. Then, MR images are collected every 7 seconds by FLASH sequence (TR=18.44 ms, TE=2.83 ms, thickness=1 mm, matrix 128×128, Fov 4 cm×4 cm). After collecting 20 slides as baseline, 0.015 mmol/kg ProCA32 were injected in mice followed by an injection of 150 μl saline through tail vein. 130 slices were continuously collected. The concentration of ProCA3 in tissue are calculated based on the relaxivity of ProCA3 at 7 T and the signal intensity differences between the baseline images and images post injection of the contrast agents. The ProCA3 concentration in blood reached to a plateau within 2 min post injection of ProCA3 and the contrast agent concentration keep constant for at least 10 min and ProCA3 concentration decrease after 10 min post injection with blood retention half-life around 15 min in mice. As comparison, 0.2 mmol/kg Gd-DTPA was for DCE-MRI in mice. Due to the short blood retention time, the peak enhancement of blood post injection of Gd-DTPA was not observed, which was mainly caused by the extremely short blood retention time for Gd-DTPA. Compared with Gd-DTPA, ProCA32 shows extremely good blood vessel enhancement with much longer blood retention time. This is extremely significant, because ProCA32 can enhance the blood vessel image with longer time and with 1/10 dosage of injection of contrast agent compared with Gd-DTPA. We compared MR images of kidney after injection of Gd-DTPA (0.2 mmol/kg) or Gd-ProCA32 (0.02 mmol/kg). The time of kidney enhancement by Gd-DTPA is very short. The enhancement of cortex and medulla reach to maximum within than 1 min than half of the signal decreased to less than 50% within the next 1 min, which left only limited time window for data acquirement. The enhancement of kidney by ProCA32 is slower than that of Gd-DTPA. The cortex enhancement reached to the maximum after 1 min post injection and medulla enhancement was slower, which took 2 min to reach to the maximum. The half of the ProCA3 image is much longer. The slow kinetics of ProCA32 in kidney provides new insight to study kidney function by DCE-MRI.

Angiogenesis is an essential process for the tumor development and metastasis. Inhibition of angiogenesis is an effective way for the tumor therapy. However, the discovery of anti-angiogenesis drugs is hampered by the lack of sensitive methods for monitoring the drug treatment for the patients. DCE-MRI is a promising technique to monitor the tumor structure changes under drug treatment. The evaluation of tumor vasculature by DCE-MRI is quantified by calculating the permeability rate and volume of contrast agents from blood to tumor tissue after a bolus injection of MRI contrast agents. Current clinically available MRI contrast agents, such as Gd-DTPA, have been extensively applied to evaluate tumor vasculatures of brain tumors in mice, rat, dogs and human patients. DEC-MRI is also extensively applied for the development of novel anti-tumor drugs. However, the contrast agents used in DCE-MRI have many disadvantages: (1) A reliable DCE-MRI evaluation is highly dependent on arterial input function, the real-time concentration of contrast agents in blood after a bolus injection of MRI contrast agents. However, current clinically available MRI contrast agents have very small sizes and very short half-life in blood, and arterial input function of current clinically available MRI contrast agents is extremely hard to measure correctly. A MRI contrast agent with prolonged half-life can improve the AIF measurement, which further improves the accuracy and reliability of MRI contrast agents in blood. 2) An ideal MRI contrast agent should have high relaxivity and high sensitivity. The currently MRI contrast agents, however, only have a relaxivity around 5 mM$^{-1}$ s$^{-1}$. To be detected by DCE-MRI, a local contrast agent concentration of 30 µM is required. If the relaxivity of MRI contrast agent increase to 100 µM, only a local concentration 0.69 µM of contrast agent is sufficient to be detected under DCE-MRI. Therefore, a MRI contrast agent with longer circulation time and higher relaxivity is strongly required for the DCE-MRI field.

In this example, we demonstrate that protein-based MRI contrast agent, ProCA32, is a promising contrast agent for DCE-MRI due to significant longer blood circulation time and significant higher signal intensity. The blood half-life of ProCA32 in mice is more than 100 times long than that of Gd-DTPA, which made the collection of AIF easier with high accuracy and reliability. The blood signal intensity is dramatically improved after injection of ProCA32 instead of Gd-DTPA. ProCA3 also shows about 5 times higher signal intensity in kidney, indicating a potential application of ProCA3 for the evaluation of kidney function by DCE-MRI. The application of DCE-MRI for disease diagnostics is limited by the lack of MRI contrast agents with high relaxivity, high metal binding affinity and selectivity, proper blood retention time. Current clinically available MRI contrast agents all have very low relaxivity, and very short blood half-life, which made the DCE-MRI data collection and calculation unreliable. Our current developed ProCAs have more than 10 times high relaxivity, a blood half-life of 2.8 h, with a size about 2-4 nm. These unique properties made ProCAs to be the ideal candidates for evaluate tumor vasculature, kidney perfusion by DCE-MRI.

Example 9

Molecular Imaging of Tumor Biomarkers Using ProCA Variants-Molecular Imaging of GRPR in Cancer by ProCA3.Bomb Three groups the GPCR exist in the bombesin receptor family. Among these receptors, gastrin-releasing peptide receptor (GRPR) is a promising biomarker for the tumor diagnostics. Discovered in 1971 from amphibian, the natural ligand of GRPR, bombesin peptide, is found to be strongly and specifically bind to gastric-release peptide receptor (GRPR) with high affinity. It human homolog, GRP, is plays a vital role on gastric acid secretion, muscle contraction, cell differentiation. The interaction between GRP and GRPR could activate multiple signaling pathways including tumor cell proliferation, survival and differentiation. Due to the low expression level in normal tissues and high expression level in tumors, GRPR becomes a promising biomarker for the tumor diagnostics. The high affinity interaction between GRPR and bombesin made bombesin a promising targeting peptide for the molecular imaging of prostate cancer, breast cancer and small cell lung cancer.

We linked the bombesin sequence in the 3' of ProCA3 DNA in the plasmid. We further expressed and purified this novel protein-based MRI contrast agents, named ProCA32.bomb. ProCA32.bomb contains a ProCA32 sequence, which binds two Gd$^{3+}$ as contrast agents. ProCA32.bomb also has a bombesin targeting peptide, which binds to GRPR with high affinity.

To test the interaction between ProCA32.bomb and GRPR, ProCA32.bomb was incubated with H441 and PC3 cells for 30 min. MR imaging of these cells were collected after robust wash by PBS. H441 has a low expression level of GRPR while PC3 has high expression level of GRPR. PC3 has higher MRI intensity than that of H441, which means more ProCA32.bomb binds to PC3 cells. Since PC3 cells have at least 10 fold higher GRPR expression than H441 cells, these results indicate that ProCA32.bomb specifically binds to GRPR.

To further confirm the interaction between ProCA32.bomb to GRPR, we did immunofluorescence staining of ProCA3 in PC3 and H441 cells after these cells were incubated with ProCA32.bomb and robust wash. PC3 cells has higher staining of ProCA32.bomb than that H441 cells indicating that ProCA32.bomb specifically interact with GRPR.

We next imaged GRPR expression in xenograft mice model. H441 and PC3 xenografted nude mice were used to test the ability of tumor imaging on ProCA32.bomb. MRI experiments were applied when the tumor size reached around 1 cm. ProCA32.bomb was labeled with Cy5.5 and PEGylated by PEG-40. The spin echo MR image shows that PC3 tumor light up 1 day after injection and decreased afterward. Gd$^{3+}$ distribution were analyzed by ICP-OES. Consistent with MRI results, PC3 tumor has higher Gd$^{3+}$ accumulation than that of H441 tumor.

Western blot and immunofluorescence results from mice tissues confirm that the GRPR are highly expressed in both PC3 and H441 tumor, while it has exceptionally low expression in kidney, liver and heart (data not shown). Immunofluorescence images also indicate that ProCA32.bomb is accumulated in PC3 and H441 tumor, while the control organs, such as lung, have low ProCA32.bomb accumulation. These data indicate the ProCA3.bemb can be applied for the molecular imaging of GRPR in tumors.

Molecular Imaging of HRE-2 Biomarker by ProCA3.Affi

Breast cancer is a deadly disease. According to national cancer institute's report, it is estimated that 226,870 women will be diagnosed to have breast cancer and 39,510 women will die of this disease. Biomarkers such as the epidermal growth factor receptors EGFR and HER-2/Neu are highly expressed in various diseases such as breast and ovarian cancers and play important roles in disease progression and survival. HER-2 is also one of the major drug targets for targeted therapy. However, one of five HER-2/Neu current clinically available tests, including biopsy and IHC, provides incorrect results, leading to improper selection of appropriate patients for personalized treatment using biomarker targeted therapies.[76, 77] There is an urgent need to develop non-invasive and accurate methods for diagnosis and selection of patients and to monitor biomarker levels/distribution and their changes upon treatment by targeted drugs.

Instead of using HER-2 antibody for molecular imaging, we linked HER-2 affibody at the C-terminal of ProCA32, named ProCA32.affi. The purification of ProCA32.affi is the same of ProCA32 purification shown in chapter 3. We also covalently linked PEG-40 and cy5.5 at the lysine residues of the ProCA32.affi.

We next test the MRI imaging of HER-2 biomarkers in cancer in two mice models after injection of ProCA32.affi. In the xenograft model, SKOV-3 tumor was implanted in the flank the mice. After the tumor size reached about 1 cm. 0.03 mmol/kg of ProCA3.affi was I. V. injected in the mice. MR imaging were collected before injection and at different time points after injection. Tumor edge was significantly enhanced after injection of ProCA32.affi and the highest enhancement were shown at 49 h post injection of ProCA32.affi. Such enhancement is still can be detected three days post injection, while the enhancement of other organs dramatically decrease the original intensity. Since ProCA32.affi also conjugated with cy5.5, ProCA3.affi can also be used for the near infrared imaging. Consistent with MRI enhancement, the SKOV-3 tumor is enhanced after ProCA3.affi injection. Since ProCA32.affi can enhance SKOV-3 tumor in MRI and NIR imaging, this contrast agents can be further applied non-invasively evaluate HER-2 expression levels in breast and ovarian cancers.

Next, we tested the MR imaging of HER-2 in the breast cancer isotropic tumor model. MCF-10DCIS tumor cells were implanted in the nipple of the mice. MRI and NRI imaging were performed when tumor size was larger than 1 cm. The MCF-10DCIS tumor were enhanced 1 day after injection of ProCA3.affi and the tumor enhancement in MRI is consistent with the tumor enhancement in NIR imaging. These results indicate that ProCA32.affi can be used for the MRI and NIR imaging of HER-2 biomarkers. HER-2 is a prognosis biomarker for the breast cancer. Thus, these results ProCA32.affi can be used to evaluate breast cancer progression noninvasively.

Molecular Imaging of Angiogenesis by ProCA3.RGD

Tumor requires nutrition to grow. When tumor grows more than 1-2 mm in diameter, the passive perfusion of nutrient is not sufficient enough for the tumor growth. The formation of new blood vessel, angiogenesis, is essential for a tumor to overcome this growth restriction. On the other hand, angiogenesis also facilitates tumor metastases.[68] It is essential to develop an effective way to monitor the initiation of angiogenesis. The methods for the angiogenesis diagnostics are also valuable for monitoring the effects of the chemotherapy against angiogenesis.

Integrins belong to a large family of integral membrane proteins expressed in animal cells. Two transmembrane subunits, a subunit and β subunit, non-covalently interact with each other to form functional integrin. By different combinations, they are able to form more than two dozen of different integrins. The extracellular domain of integrin binds to variety of proteins in the extracellular matrix, such as fibronectin, collagen, laminnin, collagen and I-CAM-1. The intracellular domain of integrin binds to signal transduction molecule and cell skeleton, such as talin, filamin, FAK. These molecules not only transfer the extracellular signal from outside to inside of the cell, but also transfer the inside signal to the extracellular space. Integrin $\alpha_v\beta_3$ is expressed when the new blood vessel are formed. It is up-regulated when certain tissue undergoes inflammation, wound, and necrosis and tumor formation. Integrin is one of the sensitive and high expression biomarkers of angiogenesis during tumor formation.[81] The natural ligands of integrin are vitronectin, fibronectin, fibrinogen, osteopontin. To interact with integrin $\alpha_v\beta_3$, most of these ligands contains a specific amino acid sequence, RGD (Arg-Gly-Asp). The binding affinity between RGD and integrin is about $10^{-6}$ M, which is strong enough to be used as a targeting peptide for the molecular imaging.

To develop a MRI contrast agent for imaging of integrin $\alpha_v\beta_3$, we linked 4-repeat-RGD peptide at the c-terminal of ProCA32, named ProCA32.RGD. ProCA32 has two $Gd^{3+}$ binding sites and the RGD peptide is linked at the C-terminal of ProCA32 by GGG linker.

Next, we tested the interaction between ProCA32.RGD to integrin $\alpha_v\beta_3$ high expression cells, U-87-MG. Immunofluorescence results show that ProCA32.RGD can bind to U-87-MG cells. The cytoplasm staining of U-87-MG staining by ProCA3 antibody indicates that ProCA32.RGD is robustly uptake by endocytosis. As a negative control, ProCA3 without targeting peptide has no immunofluorescence staining after incubation with U-87-MG at the same conditions. These results indicate that ProCA32.RGD is a promising contrast agent for the molecular imaging of integrin $\alpha_v\beta_3$ in cancer.

Molecular Imaging of HRE-2 Biomarker by ProCA2 Variants with 4 Gd Binding Sites

Two human cancer cell lines, SKOV-3 and MDA-MB-231 were selected to examine whether the designed ProCA22 can target to cancer cells[83]. SKOV-3 is an ovarian cancer cell line with estimated $3\times10^6$ HER-2/cell. MDA-MB-231 is a breast cancer cell line with modest HER-2 levels (approximately $3\times10^4$ HER-2/cell). Binding of the Gd-ProCA2-affi to the selected cells was first analyzed by immuno-fluorescence staining using the polyclonal antibody against PEGylated parental protein ProCA22. The cell binding analyses showed that the SKOV-3 cancer cells bind more ProCA22 compared to MDA-MB-231. These results indicated that the designed ProCA22 was able to target the cancer cells with high HER-2 expression level.

Cell binding analyses was applied to examine whether the designed ProCA22 can target to cancer cells. Binding of the Gd-ProCA22 to the selected cells was first analyzed by immuno-fluorescence staining using the polyclonal antibody against PEGylated parental protein. A substantial staining intensity of ProCA22 bound to SKOV-3 cells was observed. However, the MDA-MB-231 cells demonstrated very weak staining. The immunostaining results were consistent with NIR fluorescence imaging results. Under the assumption that $1\times10^7$ cells comprise a volume of 50-100 μL, this binding capacity led to the accumulation of $Gd^{3+}$ at 10-20 µM in the cell pellets. This local concentration is sufficient to produce strong MRI contrast, especially the protein contrast agent with high relaxivity reported here.

MR images were acquired by applying the in vivo performance of MRI of CD-1 mice (20-25 g, N=4) on a 4.7 T Varian MRI system using a dedicated rodent coil with modified parameters and vary pulse sequences. During the MR scan, mice were anesthetized with 1.5% isoflurane and kept warm with a heated pad. MR images were acquired by $T_1$- and $T_2$-weighted fast spin echo sequences (TR=2 s, TE=0.022 s, and ESP=0.01 s) with field of view of 3×3 cm, matrix of 256×256, and slice thickness of 1 mm. The tumors were dissected after MRI experiments. We examined the in vivo performance of MRI of CD-1 mice (20-25 g, N=4) using a 4.7 T Varian MRI system. MR images of mice before and a series of time points after administration of approximately 100 µL of PEGylated Gd-ProCA22 (approximately 3 mM) through the tail vein. Significant contrast enhancements were observed in several organs with the greatest enhancement in the kidney, liver, and blood vessels by comparison with pre- and post-contrast $T_1$ and $T_2$ weighted images obtained at 4.7 T. Meanwhile, the positive tumor injected SKOV-3 breast cancer cells with high HER-2 expression level gave stronger enhanced images compared with the negative tumors injected MDA-MB-231 with lower HER-2 expression level. The injection dose of 4.8 µmol kg-1 was 20-fold lower than Gd-DTPA dose typically used in clinics (0.1 mmol/kg). The tissue-dependent enhancement was consistent with the biodistribution of IHC staining results. Consistent with MR imaging, a strong NIR light emission from the SKOV-3 tumor at 24-hour post-administration of the contrast agent, however, the NIR intensities at the MDA-MB-231 tumor site were much less than that of the SKOV-3 tumor.

Cy5.5 Mono Maleimide dye produces an intense signal in the Near IR (NIR) region of the spectrum. NIR imaging has high sensitivity and is coupled with the MR imaging to confirm accurate targeting of selected biomarkers to cancer cells[85]. We observed a strong NIR light emission from the SKOV-3 tumor at 24-hour post-administration of the contrast agent; however, the NIR intensities at the MDA-MB-231 tumor site were much less than that of the SKOV-3 tumor.

Here we introduced an optical imaging capability by conjugating a near-IR dye, Cy5.5 Mono Maleimide, to a cysteine residue at C-terminal of the protein to facilitate imaging analyses. The Cy5.5 Mono Maleimide has a maximum absorbance at 674 nm and a maximum emission wavelength at 689 nm. The labeling yield is as high as 70%; the unlabeled free dye was separated from labeled proteins by dialysis in 10 mM HEPES buffer. NIR images are shown before and after injecting Gd-ProCA22-affi into the mouse. It can be clearly observed that the kidney and liver were lit up 4 hours after injecting the contrast agent. Moreover, tumors and organs from the imaged mice were collected 48 h post injection of Gd-ProCA22-affi to further analyze the HER-2 targeting properties of the designed Gd-ProCA22-affi. The organs and tumors were imaged using optical animal imaging. High levels of accumulation of Cy5.5 in the liver, kidneys, and the SKOV-3 tumor were observed. In comparison, the level of Cy5.5 at the MDA-MB-231 tumor was quite low. The results strongly suggested that our protein contrast agent is able to target the tumor with high HER-2 expression level and produce the HER-2 specific MR image enhancement.

To further verify the contrast agent targeted to the HER-2 positive tumor, we applied immune histo-chemistry (IHC) staining using the antibody PAb with tissue slides made from the tumor samples and selected organs collected from the imaged mice. Strongest staining was observed with liver and the SKOV-3 tumor tissue slides. Close examination of the staining patterns of the tumor slides revealed distribution of the designed protein both inside and outside the cancer cells with substantial stronger staining inside the cancer cells, indicating internalization of the protein contrast agent. The kidney slides also presented strong immune staining consistent with the NIR imaging finding. Interestingly, the areas near proximal tubes showed strongest staining, suggesting that the protein contrast agent may be secreted through kidney. In contrast, immune staining of negative tumor sections grown from MDA-MB-231 cell line revealed very weak staining.

Protein-Based MRI Contrast Agents for the Molecular Imaging of Prostate Cancer by ProCA1 with GRPR Targeting Peptide Nowadays, peptides with targeting capability are designed and utilized widely. However, they still have some limitations such as short biologic half-life due to rapid proteolysis, less binding affinity, lack of specificity and induction of pharmacologic side effects which limit their current clinically available application. Our design is decreasing the flexibility of the targeting peptide as well as keeping the secondary structure by grafting peptides bombesin variants to the scaffold polypeptide ProCA1. Theoretically, this new design could increase the targeting capability and specificity of MRI contrast agent ProCA1.

Bombesin variants (B10, G10 and B14) were successfully grafted to ProCA1 by the flexible linker GGSGG. Bombesin variants share the same heptapeptide sequence at the C-terminus which suggests that there will be some important functions such as binding affinity. According to Patel's report, the binding affinity of bombesin to GRPR is about 2.1 nM while which of GRP is about 6.6 nM. To screen GRPR targeting sequence with higher binding affinity, we designed a series of ProCA1 linked with bombesin analogues and did several experiments in vitro and in vivo to select the best one.

To identify whether the secondary structures of ProCA1 variants were maintained or not, the protein folding property was investigated by fluorescent spectroscopy. ProCA1 was analyzed in 10 mM HEPES buffer at pH 7.4. Protein concentration is fixed at 5 µM. The emission spectra were collected from 300 nm to 400 nm with an excitation wavelength of 282 nm. Tryptophan was used as a control. If the structure of ProCA1 was destroyed, tryptophan residues inside of ProCA1 would expose to buffer. And thus, the emission spectrum of ProCA1 would be similar to the free tryptophan. The emission spectrum of pure tryptophan was observed at 360 nm while the emission spectrum of ProCA1 variants appeared at 330 nm. Compared the spectrum of tryptophan and ProCA1 variants, the spectrum of ProCA1 variants had blue shift here which indicated ProCA1 variants were well folded.

To determine the Kd of FLUO-5N to $Gd^{3+}$, the concentration of FLUO-5N was fixed at 1 µM and titrated with standard $Gd^{3+}$ solution. The buffer system contained 2 mM nitrilotriacetate. The fluorescence signal of FLUO-5N increased till it was up to saturation state. The fluorescence signal intensity plots were fitted by hill equation. The calculated Kd value ($5.2*10^{-12}$M) was consistent with other's result (Kd=$3.8*10^{-12}$ M).

The Kd of ProCA1 variants to Gd$^{3+}$ was determined by the competition between ProCA1 variants and FLUO-5N. When the concentrations of FLUO-5N and Gd$^{3+}$ were fixed, ProCA1 variants were gradually added to the sample solution to compete Gd$^{3+}$ with FLUO-5N.

Where Kd1 is the dissociation constant for FLUO-5N, [FLUO-5N]T is the total concentration of FLUO-5N, Kapp is the apparent dissociation constant for protein and Kd2 is the dissociation constant for protein. Compare Kd of ProCA1 variants to Gd$^{3+}$, ProCA1B14 showed the highest binding affinity to Gd$^{3+}$ among them.

Before we did the MRI experiment, we needed to measure the relaxivity of ProCA1 variants. The concentration of Gd$^{3+}$ was fixed at 50 µM and a series of Gd$^{3+}$ to protein ratios were designed to determine the relaxivity of ProCA1 variants. From the raw data, using T1 value as an example, the relaxivity of ProCA1 increased while the concentration of protein increased until it reached to saturate state.

r1 and r2 were calculated from the equation II when the t1 and t2 value of ProCA1 variants and buffer were measured. Theoretically, when the ratio of ProCA1 to Gd$^{3+}$ was up to 1:1, the relaxivity saturate. Even when the ratio of ProCA1 to Gd$^{3+}$ was up to 2:1 or 3:1, the relaxivity didn't increase. The relaxivity of ProCA1 at the 1:1 binding site was the relative intensity of this contrast agent in this specific magnetic field.

$$R1,2 = (1/T1,2 Sample - 1/T1,2 buffer)/[ProCA] \quad \text{II}$$

The relaxivity of ProCA1 variants which were measured at 25° C. were shown in the table. All ProCA1 variants showed much higher relaxivity (17-28 mM$^{-1}$s$^{-1}$, 25□ 60 MHz) than that of current clinically available contrast agents (3.5 mM$^{-1}$s$^{-1}$).

Scatchard plot is a classical method to calculate Kd of ProCA1 variants to GRPR. GRPR number on different cell surface can be quantified by Scatchard equation (III). In this equation, Ka is the associate affinity constant, [B] is the concentration of binding receptors, [F] is the concentration of free receptors, and [Rt] is the total concentration of receptors. A plot of B/F versus B is known as a Scatchard plot.

$$[B]/[F] = Ka[R_T] - Ka[B] \quad \text{III}$$

In this experiment, [R$_T$] was the concentration of total ProCA1 variants added, [B] was the concentration of binding ProCA1 variants, [F] was the concentration of free receptors. A standard curve of absorbance versus the concentration of precultured ProCA1 variants is utilized to calculate [B] which corresponds to the absorbance of the wells of precultured PC3 cell lysate. [F] was calculated by [R$_T$] minus [B]. Ka was the concentration of ProCA1 variants at which the GRPR is half-maximally occupied by ProCA1 variants. According to Kd=1/Ka, dissociate constants of ProCA1 variants were calculated. Among them, ProCA1B14 had the highest binding affinity (Kd=2.8 nM). The GRP receptor numbers were also calculated from equation III which equals the value of [B$_{max}$]. [B$_{max}$] was the intercept on the B axis. Traditional Scatchard plot rely on radio-labeled antibody identifying precultured antigen to calculate [B]. The improved method has good accuracy as well as the radio-labeled method and is more easily manipulated and safer.

Based on those in vitro investigations of ProCA1 variants, ProCA1B14 which has the highest binding affinity to GRPR among all variants and better relaxivity than Gd-DTPA, was chosen as a representative for the in vivo experiment. ProCA1B14 was PEGylated to increase the solubility of the protein and decreased its immunogenicity. ProCA1B14 was also conjugated with NIR dye Cy5.5 before it was used in the MRI scanning.

H441 and PC3 cancer cell lines which express different levels of GRPR were injected in left and right flank of athymic mice which grew up as tumor (1 cm) xenograft models. The contrast agent ProCA1B14 (5 µM, 50 µl) was injected into the mice by tail vein injection. MR images were recorded at different time points (pre-scan and 10 min, 30 min, 24 h, and 48 h after injection) to trace the change of contrast enhancement in tumor regions. The contrast enhancement of H441 tumor increased gradually and reached the highest level at the time point 24 h post injection. Then, the signal intensity of H441 began to decrease. While, the contrast enhancement of PC3 tumor increased gradually and reached the highest level at the time point 48 h post injection. There is an interesting phenomenon that the signal intensity of PC3 was lower than that of H441 before 24 h, however, the condition reversed after 24 h. The possible reason is that more and more free ProCA1B14 went through the whole body of mice and targeted to GRPR on PC3 tumor surface because PC3 has higher GRPR expression level than that of H441.

Consistent with MR imaging, we observed a strong NIR light emission from the PC3 tumor and H441 tumor at 48 h post injection of ProCA1B14. However, the NIR intensities at H441 tumor site were much less than that of the PC3 tumor. To probe the distribution of ProCA1B14 in the tumor tissues after MRI scan, we did immunofluorescence staining. The mice with xenografted tumors were sacrificed and representative organs were immersed in flek O.C.T and fixed by liquid nitrogen. All the samples were stored at −80° C. The cryosectioning was performed by cryostas (Biology facility, GSU). The anti-ProCA1 primary antibody reacted with ProCAB14, which binds GRPR and accumulated in the tissues. The goat anti rabbit secondary antibody conjugated with fluo 594 was added to react with the primary antibody. The immunofluorescence intensity signal was coming from the recognition of secondary antibody conjugated with fluorescence dye to anti-ProCA1 primary antibody. Compare the fluorescence intensity, ProCA1B14 binds GRPR on PC3 and H441 tumors and some of them were internalized in the cell. PC3 tumor showed stronger staining than that of H441 tumor which was consistent with the Gd$^{3+}$ distribution studies by ICP-OES.

To detect the location of ProCA1B14 in the examined tumor tissues, we did immunohistochemistry staining. The mice with xenografted tumors were sacrificed and representative organs were immersed in flek O.C.T and fixed by liquid nitrogen. All the samples were stored at −80° C. The cryosectioning was performed by cryostas (Biology facility, GSU). The frozen tissue samples were stained by using the IHC protocol mentioned above. As shown in the FIG. 17, the brown color indicates the staining of ProCA1B14 binding to the GRPR on tumors, while the blue color indicates the hematoxylin background staining. Compare the staining of PC3 and H441 tumor slides, we found that PC3 tumor showed stronger brown color than that of H441 tumor which indicates PC3 tumor has more GRPR expression and some ProCA1B14 already internalized in the cells. The IHC results were consistent with our MRI data and confirmed that our ProCA1B14 can be used as a MRI contrast agent to semi-quantitatively analyze the receptor change in tumors.

Since GRPR highly expressed on prostate tumor surface compared with normal prostate, GRPR is a promising biomarker for prostate cancer diagnosis and treatment. The targeting capability of ProCA1 to GRPR is optimized by grafting targeting sequence with strong binding affinity. Scatchard plot experiments have been used to quantitatively analyze that the binding affinity of ProCA1 variants to GRPR on cancer cell lines. Among three of them, ProCA1B14 shows the strongest binding affinity which is a critical feature for a molecular imaging agent. ProCA1B14 has also been confirmed with high $Gd^{3+}$ binding affinity and high relaxivity which proved its excellent sensitivity as a MRI contrast agent and safety profile for future application. The MRI intensity signals of PC3 tumor and H441 tumor in xenografted mice were dominantly enhanced after injection of ProCA1B14 under 7 T MR scanner. The tumor enhancement was further confirmed by ICP-OES and NIR imaging. Interestingly, the intensity enhancement of PC3 tumor and H441 tumor were correlated well with the difference of GRPR expression levels in PC3 tumor and H441 tumor which indicates the possibility of using MRI to quantitatively trace the dynamic changes of biomarkers during the disease development. Considering the dynamic changes of biomarkers are usually related with the stage of cancers, this kind of innovation will contribute to evaluate the stage of prostate cancer and drug treatment effects in the current clinically available applications.

Protein-Based MRI Contrast Agents for the Molecular Imaging of Cancer by ProCA1 with HER-2 or EGFR Targeting Affibody The ProCA1-affi1907 was created by fusion of affibody $Z_{EGFR1907}$ which can specifically target to EGFR. The epitope locates in helix 1 and 2 with 13 amino acids. This three helix protein which consists of 58 amino acids were cloned to the C-terminal of ProCA1-CD2 with a GGSGG linker in between. In the fused protein ProCA1-affi1907, there is one $Gd^{3+}$ binding site in ProCA1-CD2 which can function as an MRI contrast agent. The affibody $Z_{EGFR1907}$ keeps the helix structure with the EGFR binding sites exposed.

Same as the parental protein ProCA1-CD2, the constructed ProCA1-affi1907 was also expressed in E. coli and subsequently purified by GS-4B column for GST fusion protein. To apply this fusion protein in cells and animal experiments, PEGylation was also used to modify this protein, since PEGylation can increase the relaxivity and stability of the fusion protein. An optimized PEG size of 40 repeated PEG units was used for better tumor penetration and keeping the tumor binding capability.

ProCA1-affi1907 can specifically target to EGFR in cancer cells with high EGFR expression. Two cancer cell lines were used for immunostaining. One is breast cancer cell line MDA-MB-231, which overexpresses EGFR but only low levels of HER-2 expression. Another one is an ovarian cancer cell line SKOV-3, which overexpresses both EGFR and HER-2. The parental protein ProCA1-CD2 was used as a negative control. Binding of the Gd-ProCA1-affi1907 to the selected cells was analyzed by immuno-fluorescence staining using the polyclonal antibody against PEGylated parental protein ProCA1 (PAbPGCA1). A substantial staining intensity of ProCA1-affi1907 bound to MDA-MB-231 cells was observed and increased as incubation concentration increased. In contrast, the cells stained with ProCA1-CD2 demonstrated very week binding. In SKOV-3 cells, it showed the same phenomena as MDA-MB-231.

The ProCA1-affi1907 of different concentration was incubated with cancer cells with different expression levels of EGFR. The breast cancer cell line MDA-MB-231 has highest expression level as indicated. SKOV-3 also shows high expression level of EGFR. MCF-7 is an EGFR negative cell line.

The protein contrast agents would result in MRI contrast enhancement in xenograft orthotopic models of MCF-10DCIS human cancer cell lines. The contrast agent $Gd^{3+}$ ProCA1-affi342 at concentration of 3 mM (100 fold lower than current clinically-approved contrast agent DTPA) was administrated via the tail vein. Pre- and post-contrast MRI were collected at different time points using T1 and T2 weighted fast spin echo or T1 weighted gradient echo sequences. The mice were imaged using two pulse sequences: the T1 and T2 weighted fast spin echo sequence (TR=2 s, TE=0.022 or 0.066 s) and the T1-weighted gradient echo sequence (TR=0.088 s, TE=2 ms and P=0.009 s). The fields of view are 3 cm×3 cm with matrix of 256×256 and slice of 1 mm in thickness. Image J was used to quantitatively analyze the MRI images obtained. The regions of interest (ROI) were selected by circling the tumor sites. Then the signal intensities of the ROIs were calculated and compared. Six adjacent slides were selected to measure signal changes which were averaged to obtain statistical significant results. At 3 time point, the tumor site exhibited significant contrast enhancement. Strong contrast enhancement was observed in the tumor 24 hours after injection. Such MRI contrast enhancement was decreased after 24 h post injection. The tumor showed enhancement in edge area, however, the center of the tumor was still dark as pre-scan. This result demonstrated the heterogeneous structure of tumor.

The biomarker may not only have expression level change during the progression and drug treatments, the morphology or the distribution of biomarkers may also change inside the tumor. IHC can clearly demonstrate the distribution of biomarker in the tumor by staining both the biomarker, like HER-2 and nucleus. Since MRI is a technique with high resolution, we expect to use our designed MRI contrast agents to monitor the tumor structure. At the time point of 24 h, when most contrast agents concentrated in the tumor area, the heterogeneous structure can be viewed. This MRI results confirms the biomarkers like HER-2 detected by ProCA1-affi342 inside the tumor area is heterogeneous. The MRI is able to image the structure of the tumor; however, the resolution is not as high as IHC to give the information of the distribution of HER-2. The DCE-MRI (Dynamic Contrast Enhancement) is expected to give more information about the biomarker changes.

We claim the following:

1. An MRI contrast agent comprising:
   (i) a polypeptide having an amino acid sequence with at least 85% similarity to sequence SEQ ID NO: 22 and having at least one of a first paramagnetic metal ion chelation site comprising negatively charged amino acid side-group oxygen atoms at at least four of positions 52, 54, 56, 60 and 63 of SEQ ID NO: 22 and a second paramagnetic metal ion chelation site comprising negatively-charged amino acid side-group oxygen atoms at at least four of positions 91, 93, 95, 99 and 102 of SEQ ID NO: 22, wherein in each paramagnetic metal ion chelation site said amino acid side-group oxygen atoms are positioned to chelate a paramagnetic metal ion;
   (ii) at least one polyethylene glycol molecule attached to the polypeptide; and
   (iii) a paramagnetic metal ion chelated to at least one of the first and the second paramagnetic metal ion chelation sites of the polypeptide, said paramagnetic metal ion is selected from the group consisting of $Gd^{3+}$, $Eu^{3+}$, $Tm^{3+}$, $Yb^{3+}$, $Lu^{3+}$, $Mn^{2+}$, and $Fe^{3+}$;
   and wherein:
   (a) in each paramagnetic metal ion chelation site the negatively-charged amino acid side-group oxygen atoms interacting with the metal ion are between about 2 angstrom units and about 5 angstrom units from the metal ion;
   (b) the metal ion electrostatically interacts with at least one water molecule and at a distance of less than about 10 angstrom units therefrom;
   (c) the metal ion or ions are chelated to a beta-fold region of the polypeptide or at least one loop and an alpha-helix; and
   (d) the polypeptide includes a target-specific amino acid sequence specific for a cell-specific target of a hepatic tumor, a renal tumor, or a cardiovascular-specific target.

2. The MRI contrast agent of claim 1, wherein the polypeptide has an amino acid sequence having at least 90% similarity to SEQ ID NO: 22.

3. The MRI contrast agent of claim 2, wherein the polypeptide has an amino acid sequence having at least 95% similarity to SEQ ID NO: 22.

4. The MRI contrast agent of claim 3, wherein the polypeptide has the amino acid residues 1-112 of SEQ ID NO: 22.

5. A pharmaceutically acceptable composition formulated for administration to a human or non-human animal comprising an MRI contrast agent comprising:
   an MRI contrast agent comprising:
   (i) a polypeptide having an amino acid sequence with at least 85% similarity to sequence SEQ ID NO: 22 and having at least one of a first paramagnetic metal ion chelation site comprising negatively charged amino acid side-group oxygen atoms at at least four of positions 52, 54, 56, 60 and 63 of SEQ ID NO: 22 and a second paramagnetic metal ion chelation site comprising negatively-charged amino acid side-group oxygen atoms at at least four of positions 91, 93, 95, 99 and 102 of SEQ ID NO: 22, wherein in each paramagnetic metal ion chelation site said amino acid side-group oxygen atoms are positioned to chelate a paramagnetic metal ion;
   (ii) at least one polyethylene glycol molecule attached to the polypeptide; and
   (iii) a paramagnetic metal ion chelated to at least one of the first and the second paramagnetic metal ion chelation sites of the polypeptide, said paramagnetic metal ion is selected from the group consisting of $Gd^{3+}$, $Eu^{3+}$, $Tm^{3+}$, $Yb^{3+}$, $Lu^{3+}$, $Mn^{2+}$, and $Fe^{3+}$;
   and wherein:
   (a) in each paramagnetic metal ion chelation site the negatively-charged amino acid side-group oxygen atoms interacting with the metal ion are between about 2 angstrom units and about 5 angstrom units from the metal ion;
   (b) the metal ion electrostatically interacts with at least one water molecule and at a distance of less than about 10 angstrom units therefrom;
   (c) the metal ion or ions are chelated to a beta-fold region of the polypeptide or at least one loop and an alpha-helix; and (d) the polypeptide includes a target-specific amino acid sequence specific for a cell-specific target of a hepatic tumor, a renal tumor, or a cardiovascular-specific target, and a pharmaceutically acceptable carrier.

6. A method of obtaining an MRI image of a tissue, said method comprising the steps:
(a) administering to a human or non-human animal a pharmaceutically acceptable dose of a contrast agent, wherein said contrast agent comprises:
  (i) a polypeptide having an amino acid sequence with at least 85% similarity to sequence SEQ ID NO: 22 and having at least one of a first paramagnetic metal ion chelation site comprising negatively charged amino acid side-group oxygen atoms at at least four of positions 52, 54, 56, 60 and 63 of SEQ ID NO: 22 and a second paramagnetic metal ion chelation site comprising negatively-charged amino acid side-group oxygen atoms at at least four of positions 91, 93, 95, 99 and 102 of SEQ ID NO: 22, wherein in each paramagnetic metal ion chelation site said amino acid side-group oxygen atoms are positioned to chelate a paramagnetic metal ion;
  (ii) at least one polyethylene glycol molecule attached to the polypeptide; and
  (iii) a paramagnetic metal ion chelated to at least one of the first and the second paramagnetic metal ion chelation sites of the polypeptide, said paramagnetic metal ion is selected from the group consisting of $Gd^{3+}$, $Eu^{3+}$, $Tm^{3+}$, $Yb^{3+}$, $Lu^{3+}$, $Mn^{2+}$, and $Fe^{3+}$;
  and wherein:
    (a) in each paramagnetic metal ion chelation site the negatively-charged amino acid side-group oxygen atoms interacting with the metal ion are between about 2 angstrom units and about 5 angstrom units from the metal ion;
    (b) the metal ion electrostatically interacts with at least one water molecule and at a distance of less than about 10 angstrom units therefrom;
    (c) the metal ion or ions are chelated to a beta-fold region of the polypeptide or at least one loop and an alpha-helix; and
    (d) the polypeptide includes a target-specific amino acid sequence specific for a cell-specific target of a hepatic tumor, a renal tumor, or a cardiovascular-specific target;
(b) subjecting the human or non-human animal to MRI, thereby obtaining a T1 and a T2 determination;
(c) determining the T2/T1 or T1/T2 intensity ratio of the MRI image; and
(d) obtaining an image of the T2/T1 or T1/T2 intensity ratio relative to a tissue of the human or non-human animal, thereby determining the location of the contrast agent in the human or non-human animal, thereby identifying a target tissue.

7. The method of claim 6, wherein (i) in the contrast agent the metal ion or ions are chelated to a beta-fold region of the polypeptide or at least one loop and an alpha-helix; and (ii) the contrast agent provides an image of a hepatic tumor having a size less than about 0.25 microns.

8. The method of claim 6, wherein the contrast agent comprises a polypeptide having an amino acid sequence having at least 90% similarity to the sequence SEQ ID NO: 22.

9. The method of claim 6, wherein the contrast agent comprises a polypeptide having an amino acid sequence having at least 95% similarity to the sequence SEQ ID NO: 22.

10. The method of claim 9, wherein the polypeptide has the amino acid residues 1-112 of SEQ ID NO: 22.

11. A method for DCE-MR imaging using a contrast agent, wherein the contrast agent comprises,
(i) a polypeptide having an amino acid sequence with at least 85% similarity to sequence SEQ ID NO: 22 and having at least one of a first paramagnetic metal ion chelation site comprising negatively charged amino acid side-group oxygen atoms at at least four of positions 52, 54, 56, 60 and 63 of SEQ ID NO: 22 and a second paramagnetic metal ion chelation site comprising negatively-charged amino acid side-group oxygen atoms at at least four of positions 91, 93, 95, 99 and 102 of SEQ ID NO: 22, wherein in each paramagnetic metal ion chelation site said amino acid side-group oxygen atoms are positioned to chelate a paramagnetic metal ion;
(ii) at least one polyethylene glycol molecule attached to the polypeptide; and
(iii) a paramagnetic metal ion chelated to at least one of the first and the second paramagnetic metal ion chelation sites of the polypeptide, said paramagnetic metal ion is selected from the group consisting of $Gd^{3+}$, $Eu^{3+}$, $Tm^{3+}$, $Yb^{3+}$, $Lu^{3+}$, $Mn^{2+}$, and $Fe^{3+}$;
and wherein:
  (a) in each paramagnetic metal ion chelation site the negatively-charged amino acid side-group oxygen atoms interacting with the metal ion are between about 2 angstrom units and about 5 angstrom units from the metal ion;
  (b) the metal ion electrostatically interacts with at least one water molecule and at a distance of less than about 10 angstrom units therefrom;
  (c) the metal ion or ions are chelated to a beta-fold region of the polypeptide or at least one loop and an alpha-helix; and
  (d) the polypeptide includes a target-specific amino acid sequence specific for a cell-specific target of a hepatic tumor, a renal tumor, or a cardiovascular-specific target,
and a pharmaceutically acceptable carrier,
wherein the method comprises the steps of:
  a) determining a T1 map of a human or non-human animal tissue;
  b) collecting a first series of MRI images at identical time intervals and with a basal signal;
  c) administering the contrast agent to a blood vessel of the human or non-human animal;
  d) collecting a second series of MRI images at identical time intervals and with a basal signal; and
  e) determining the permeability and blood volume of the tissue using the MRI images collected in steps (a) and (d).

12. The method of claim 11, wherein the contrast agent has the amino acid residues 1-112 of SEQ ID NO: 22.

* * * * *